United States Patent
Shioda et al.

(10) Patent No.: US 9,635,857 B2
(45) Date of Patent: *May 2, 2017

(54) TETRAZOLINONE COMPOUND AND USE THEREOF

(71) Applicant: SUMITOMO CHEMICAL COMPANY, LIMITED, Tokyo (JP)

(72) Inventors: Takayuki Shioda, Takarazuka (JP); Yuya Yoshimoto, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/029,015

(22) PCT Filed: Oct. 23, 2014

(86) PCT No.: PCT/JP2014/078839
§ 371 (c)(1),
(2) Date: Apr. 13, 2016

(87) PCT Pub. No.: WO2015/060461
PCT Pub. Date: Apr. 30, 2015

(65) Prior Publication Data
US 2016/0235065 A1    Aug. 18, 2016

(30) Foreign Application Priority Data

Oct. 25, 2013  (JP) .................................. 2013-221910

(51) Int. Cl.
| | |
|---|---|
| *A01N 43/713* | (2006.01) |
| *C07D 257/04* | (2006.01) |
| *C07D 403/12* | (2006.01) |
| *C07D 401/12* | (2006.01) |
| *A01N 43/76* | (2006.01) |
| *A01N 43/78* | (2006.01) |
| *C07D 413/12* | (2006.01) |
| *C07D 417/12* | (2006.01) |
| *C07D 401/14* | (2006.01) |

(52) U.S. Cl.
CPC ........... *A01N 43/713* (2013.01); *A01N 43/76* (2013.01); *A01N 43/78* (2013.01); *C07D 257/04* (2013.01); *C07D 401/12* (2013.01); *C07D 401/14* (2013.01); *C07D 403/12* (2013.01); *C07D 413/12* (2013.01); *C07D 417/12* (2013.01)

(58) Field of Classification Search
CPC ... A01N 43/713; C07D 257/04; C07D 403/12
USPC ...................................................... 514/241
See application file for complete search history.

(56) References Cited

U.S. PATENT DOCUMENTS

| | | | |
|---|---|---|---|
| 6,583,090 B1 | 6/2003 | Gewehr et al. | |
| 7,056,941 B1 | 6/2006 | Müller et al. | |
| 2016/0081339 A1* | 3/2016 | Yoshimoto | ........... C07D 403/12 |
| | | | 514/236.2 |
| 2016/0159755 A1* | 6/2016 | Shioda | ................. C07D 403/12 |
| | | | 514/274 |

FOREIGN PATENT DOCUMENTS

| | | |
|---|---|---|
| JP | 9-208565 A | 8/1997 |
| JP | 2001-510840 A | 8/2001 |
| JP | 2002-506060 A | 2/2002 |
| JP | 2014-141451 A | 8/2014 |
| WO | WO 96/36229 A1 | 11/1996 |
| WO | WO 9636229 A1 * | 11/1996 ............. A01N 43/56 |
| WO | WO 2013/092224 A1 | 6/2013 |
| WO | WO 2013/162072 A1 | 10/2013 |
| WO | WO 2013/162077 A1 | 10/2013 |
| WO | WO 2014/051161 A1 | 4/2014 |
| WO | WO 2014/051165 A1 | 4/2014 |
| WO | WO 2014/104384 A1 | 7/2014 |
| WO | WO 2014/175465 A1 | 10/2014 |

OTHER PUBLICATIONS

International Search Report for PCT/JP2014/078839 mailed on Jan. 6, 2015.
English translation of the Written Opinion of the International Searching Authority, dated Jan. 6, 2015, for International Application PCT/JP2014/078839.

* cited by examiner

*Primary Examiner* — Kamal Saeed
*Assistant Examiner* — Janet L Coppins
(74) *Attorney, Agent, or Firm* — Birch, Stewart, Kolasch & Birch, LLP

(57) ABSTRACT

A tetrazolinone compound represented by formula (1):

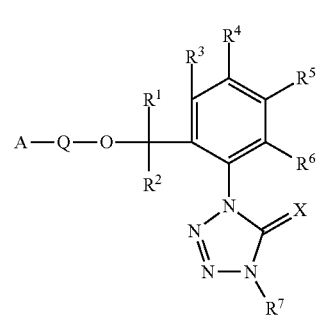

wherein $R^1$ and $R^2$ each represents a hydrogen atom, a halogen atom, or a C1-C3 alkyl group; $R^3$ represents a C1-C3 alkyl group optionally having one or more halogen atoms; $R^4$, $R^5$, and $R^6$ each represents a hydrogen atom or a halogen atom; $R^7$ represents a C1-C3 alkyl group; Q represents a divalent group selected from Group $P^4$; and A represents a C7-C18 aralkyloxy group optionally having one or more atoms or groups selected from Group $P^3$, has excellent control activity against pests.

10 Claims, No Drawings

TETRAZOLINONE COMPOUND AND USE THEREOF

TECHNICAL FIELD

The present invention relates to a tetrazolinone compound and use thereof.

BACKGROUND ART

Heretofore, various chemicals have been developed so as to control pests and provided in practice use, but in some cases, these chemicals may not exert enough activity.

Meanwhile, there have been known, as compounds having a tetrazolinone ring, compounds represented by formula (A):

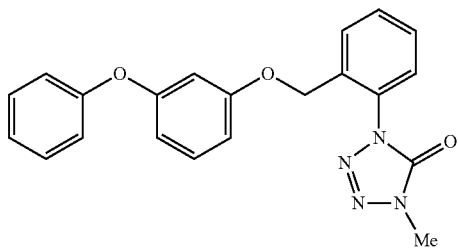

(see WO 96/036229 A).

DISCLOSURE OF THE INVENTION

The present invention provides compounds having excellent control activity against pests.

The present inventors have intensively studied so as to find compounds having excellent control activity against pests, and found that a tetrazolinone compound represented by the following formula (1) has excellent control activity against pests, thus completing the present invention.

The present invention includes the followings [1] to [11].

[1] A tetrazolinone compound represented by formula (1):

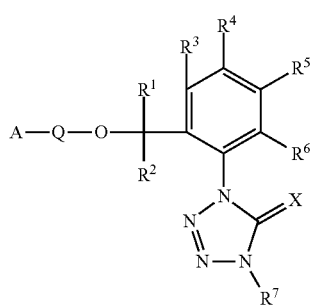

wherein $R^1$ and $R^2$ each independently represents a hydrogen atom, a halogen atom, or a C1-C3 alkyl group;

$R^3$ represents a C1-C6 alkyl group optionally having one or more halogen atoms, a C1-C6 alkoxy group optionally having one or more halogen atoms, a C3-C6 cycloalkyl group optionally having one or more halogen atoms, a halogen atom, a C2-C6 alkenyl group optionally having one or more halogen atoms, a cyano group, a C1-C6 alkylthio group optionally having one or more halogen atoms, a C2-C6 alkynyl group optionally having one or more halogen atoms, a nitro group, an aminocarbonyl group optionally having one or more C1-C6 alkyl groups, a C3-C6 cycloalkyloxy group optionally having one or more halogen atoms, a C3-C6 cycloalkylthio group optionally having one or more halogen atoms, a C3-C6 alkenyloxy group optionally having one or more halogen atoms, a C3-C6 alkynyloxy group optionally having one or more halogen atoms, a C3-C6 alkenylthio group optionally having one or more halogen atoms, a C3-C6 alkynylthio group optionally having one or more halogen atoms, a C2-C6 alkoxycarbonyl group, a hydroxy group, a sulfanyl group, a C1-C8 alkylamino group optionally having one or more halogen atoms, a pentafluorosulfanyl group, a C3-C9 trialkylsilyl group, a C1-C6 alkylsulfonyl group optionally having one or more halogen atoms, a C1-C6 alkylsulfinyl group optionally having one or more halogen atoms, a C2-C6 alkylcarbonyl group, a C2-C5 alkoxyalkyl group, or a C2-C5 alkylthioalkyl group;

$R^4$, $R^5$ and, $R^6$ each independently represents a hydrogen atom, a halogen atom, a C1-C3 alkyl group optionally having one or more halogen atoms, or a C1-C3 alkoxy group optionally having one or more halogen atoms;

$R^7$ represents a C1-C3 alkyl group optionally having one or more halogen atoms;

Q represents a divalent group selected from Group $P^4$,

A represents a C6-C16 aryloxy group optionally having one or more atoms or groups selected from Group $P^2$, a C6-C16 arylthio group optionally having one or more atoms or groups selected from the Group $P^2$, $R^{15}O$—N=C($R^{16}$)—, $R^{13}R^{14}N$—N=C($R^{16}$)—, $R^{13}R^{14}N$—CH=N—, a C7-C18 aralkyl group optionally having one or more atoms or groups selected from Group $P^2$, a C7-C18 aralkyloxy group optionally having one or more atoms or groups selected from Group $P^2$, a C7-C16 aryloxyalkyl group optionally having one or more atoms or groups selected from Group $P^2$, a C7-C16 arylcarbonyl group optionally having one or more atoms or groups selected from Group $P^2$, an anilino group optionally having one or more atoms or groups selected from Group $P^2$, a C2-C9 heteroaryloxy group optionally having one or more atoms or groups selected from Group $P^2$, wherein the heteroaryl moiety in the heteroaryloxy group represents a 5-membered ring, a 6-membered ring, a fused ring of a 5-membered ring and a 5-membered ring, a fused ring of a 5-membered ring and a 6-membered ring, or a fused ring of a 6-membered ring and a 6-membered ring, a C3-C6 cycloalkyloxy group, or a C4-C10 cycloalkylalkoxy group;

$R^{13}$ and $R^{14}$ are the same or different and represent a C1-C3 alkyl group optionally having one or more halogen atoms;

$R^{15}$ represents a C1-C6 alkyl group optionally having one or more halogen atoms, a C2-C6 alkenyl group optionally having one or more halogen atoms, a C2-C6 alkynyl group optionally having one or more halogen atoms, a C3-C6 cycloalkyl group optionally having one or more halogen atoms, a C7-C18 aralkyl group optionally having one or more atoms or groups selected from Group $P^1$, or a phenyl group optionally having one or more atoms or groups selected from Group $P^1$;

$R^{16}$ represents a C1-C6 alkyl group optionally having one or more halogen atoms, a hydrogen atom, a C3-C6 cycloalkyl group optionally having one or more halogen atoms, or a phenyl group optionally having one or more halogen atoms;

X represents an oxygen atom or a sulfur atom:

Group $P^1$: Group consisting of a halogen atom, a cyano group, a C1-C4 alkyl group optionally having one or more halogen atoms, a C3-C6 cycloalkyl group optionally having one or more halogen atoms, a C1-C4 alkoxy group optionally having one or more halogen atoms, and a C1-C4 alkylthio group optionally having one or more halogen atoms;

Group $P^2$: Group consisting of a C1-C6 alkyl group optionally having one or more halogen atoms, a halogen atom, a cyano group, a hydroxy group, a C3-C6 cycloalkyl group optionally having one or more halogen atoms, a C1-C6 alkoxy group optionally having one or more halogen atoms, a C1-C6 alkylthio group optionally having one or more halogen atoms, a C2-C6 alkenyl group optionally having one or more halogen atoms, a C2-C6 alkynyl group optionally having one or more halogen atoms, a C1-C8 alkylamino group optionally having one or more halogen atoms, a C1-C6 alkylsulfinyl group optionally having one or more halogen atoms, a C1-C6 alkylsulfonyl group optionally having one or more halogen atoms, a pentafluorosulfanyl group, a C2-C6 alkoxycarbonyl group, a C2-C6 alkylcarbonyl group, a C2-C6 alkylcarbonyloxy group, a C2-C6 alkylcarbonylamino group, an aminocarbonyl group optionally having one or more C1-C6 alkyl groups, and a C3-C9 trialkylsilyl group; and Group $P^4$: Group consisting of a group Q1 and a group Q2:

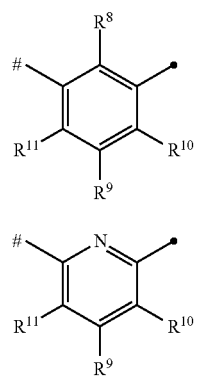

wherein $R^8$, $R^9$, $R^{10}$ and $R^{11}$ are the same or different and represent a hydrogen atom, a halogen atom, or a C1-C4 alkyl group optionally having one or more halogen atoms, the symbol # represents a binding site for A, and the symbol ● represents a binding site for an oxygen atom.

[2] The tetrazolinone compound according to [1], wherein $R^1$, $R^2$, $R^4$, $R^5$, and $R^6$ are hydrogen atoms;
$R^3$ is a C1-C4 alkyl group optionally having one or more halogen atoms, a halogen atom, a C1-C4 alkoxy group optionally having one or more halogen atoms, or a C3-C5 cycloalkyl group optionally having one or more halogen atoms; and
Q is the following group Q1:

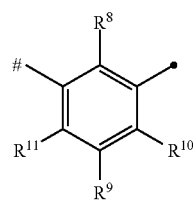

wherein $R^8$, $R^9$, $R^{10}$, $R^{11}$, the symbol #, and the symbol ● are the same as defined above.

[3] The tetrazolinone compound according to [1] or [2], wherein A is the following group S1':

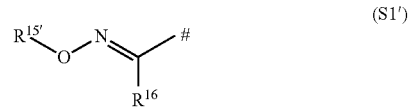

wherein $R^{15'}$ represents a C1-C6 alkyl group optionally having one or more halogen atoms, a C2-C6 alkenyl group optionally having one or more halogen atoms, a C2-C6 alkynyl group optionally having one or more halogen atoms, a benzyl group optionally having one or more atoms or groups selected from Group $P^3$, or a phenyl group optionally having one or more atoms or groups selected from Group $P^3$, $R^{16}$ represents a C1-C6 alkyl group optionally having one or more halogen atoms, a hydrogen atom, a C3-C6 cycloalkyl group optionally having one or more halogen atoms, or a phenyl group optionally having one or more halogen atoms, and $R^{16}$ and # are the same as defined above: Group $P^3$: Group consisting of a halogen atom, a cyano group, a C1-C3 alkyl group optionally having one or more halogen atoms, a C1-C3 alkoxy group optionally having one or more halogen atoms, a C3-C4 cycloalkyl group optionally having one or more halogen atoms, and a C1-C3 alkylthio group optionally having one or more halogen atoms.

[4] The tetrazolinone compound according to [1] or [2], wherein A is a C7-C18 aralkyloxy group optionally having one or more atoms or groups selected from Group $P^3$.

[5] The tetrazolinone compound according to [1] or [2], wherein $R^8$, $R^9$, and $R^{11}$ are hydrogen atoms, and $R^{10}$ is a C1-C4 alkyl group optionally having one or more halogen atoms.

[6] The tetrazolinone compound according to [1], wherein $R^1$, $R^2$, $R^4$, $R^5$, and $R^6$ are hydrogen atoms;
$R^3$ is a C1-C4 alkyl group optionally having one or more halogen atoms, a halogen atom, a C1-C4 alkoxy group optionally having one or more halogen atoms, or a C3-C5 cycloalkyl group optionally having one or more halogen atoms; and
Q is the following group Q2':

wherein the symbol # represents a binding site for A, and the symbol ● represents a binding site for an oxygen atom.

[7] The tetrazolinone compound according to [1], [2], [5], or [6], wherein A is a group S1":

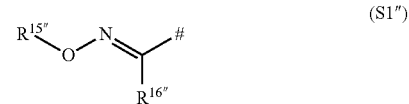

wherein $R^{15''}$ represents a C1-C6 alkyl group optionally having one or more halogen atoms, a C2-C6 alkenyl group optionally having one or more halogen atoms, a C2-C6 alkynyl group optionally having one or more halogen atoms, a benzyl group optionally having one or more halogen atoms selected from Group P⁵, or a phenyl group optionally having one or more halogen atoms, R¹⁶'' represents a C1-C6 alkyl group optionally having one or more halogen atoms, or a phenyl group optionally having one or more halogen atoms, and # is the same as defined above: Group P⁵: Group consisting of a C1-C3 alkyl group optionally having one or more halogen atoms.

[8] The tetrazolinone compound according to [1], [2], [5], or [6], wherein A is a C7-C18 aralkyloxy group optionally having one or more atoms or groups selected from Group P¹, and Group P¹ is Group consisting of a C1-C3 alkyl group optionally having one or more halogen atoms, a halogen atom, and a C1-C3 alkoxy group optionally having one or more halogen atoms.

[9] A pest control agent comprising the tetrazolinone compound according to any one of [1] to [8].

[10] A method for controlling pests, which comprises treating plants or soil with an effective amount of the tetrazolinone compound according to any one of [1] to [8].

[11] Use of the tetrazolinone compound according to any one of [1] to [8] for controlling pests.

According to the present invention, pests can be controlled.

MODE FOR CARRYING OUT THE INVENTION

A compound of the present invention is a tetrazolinone compound represented by formula (1) (hereinafter referred to as the present compound):

Formula (1)

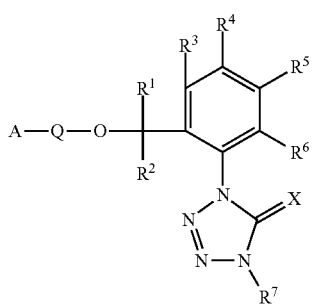

(1)

wherein R¹, R², R³, R⁴, R⁵, R⁶, R⁷, Q, A, and X are the same as defined above.

Substituents as used herein will be mentioned below.

Examples of the halogen atom include a fluorine atom, a chlorine atom, a bromine atom, and an iodine atom.

Examples of the C1-C3 alkyl group include a methyl group, an ethyl group, a propyl group, and an isopropyl group.

The C1-C3 alkyl group optionally having one or more halogen atoms represents a group in which one or more hydrogen atoms of a C1-C3 alkyl group are optionally substituted with a halogen atom, and examples thereof include a methyl group, an ethyl group, a propyl group, an isopropyl group, a chloromethyl group, a dichloromethyl group, a fluoromethyl group, a difluoromethyl group, a trifluoromethyl group, a 2,2,2-trifluoroethyl group, a pentafluoroethyl group, and a 3,3,3-trifluoropropyl group.

Examples of the C1-C6 alkyl group include a methyl group, an ethyl group, an isopropyl group, a butyl group, a tert-butyl group, and a hexyl group.

The C1-C6 alkyl group optionally having one or more halogen atoms represents a group in which one or more hydrogen atoms of a C1-C6 alkyl group are optionally substituted with a halogen atom, and examples thereof include a methyl group, an ethyl group, a propyl group, an isopropyl group, a butyl group, an isobutyl group, a sec-butyl group, a tert-butyl group, a pentyl group, a hexyl group, a chloromethyl group, a difluoromethyl group, a trifluoromethyl group, a 2,2,2-trifluoroethyl group, a pentafluoroethyl group, and a 3,3,3-trifluoropropyl group.

Examples of the C1-C4 alkyl group include a methyl group, an ethyl group, an isopropyl group, and a tert-butyl group.

The C1-C4 alkyl group optionally having one or more halogen atoms represents a group in which one or more hydrogen atoms of a C1-C4 alkyl group are optionally substituted with a halogen atom, and examples thereof include a methyl group, an ethyl group, a propyl group, an isopropyl group, a butyl group, an isobutyl group, a sec-butyl group, a tert-butyl group, a chloromethyl group, a difluoromethyl group, a trifluoromethyl group, a 2,2,2-trifluoroethyl group, a pentafluoroethyl group, a 3,3,3-trifluoropropyl group, and a 4,4,4-trifluorobutyl group.

Examples of the C2-C6 alkenyl group include a vinyl group, a 1-propenyl group, an isopropenyl group, a 2-butenyl group, a 1-methyl-2-propenyl group, a 1,3-butadienyl group, and a 1-hexenyl group.

The C2-C6 alkenyl group optionally having one or more halogen atoms represents a group in which one or more hydrogen atoms of a C2-C6 alkenyl group are optionally substituted with a halogen atom, and examples thereof include a vinyl group, a 1-propenyl group, an isopropenyl group, a 2-propenyl group, a 1-butenyl group, a 1-methyl-1-propenyl group, a 2-butenyl group, a 1-methyl-2-propenyl group, a 3-butenyl group, a 2-methyl-1-propenyl group, a 2-methyl-2-propenyl group, a 1,3-butadienyl group, a 1-pentenyl group, a 1-ethyl-2-propenyl group, a 2-pentenyl group, a 1-methyl-1-butenyl group, a 3-pentenyl group, a 1-methyl-2-butenyl group, a 4-pentenyl group, a 1-methyl-3-butenyl group, a 1-hexenyl group, a 5-hexenyl group, a 1-trifluoromethylvinyl group, and a 3,3,3-trifluoro-2-methyl-1-propenyl group.

Examples of the C2-C6 alkynyl group include an ethynyl group, a propargyl group, a 3-butynyl group, a 3-methyl-1-butyn-3-yl group, a 4-pentynyl group, and a 5-hexynyl group.

The C2-C6 alkynyl group optionally having one or more halogen atoms represents a group in which one or more hydrogen atoms of a C2-C6 alkynyl group are optionally substituted with a halogen atom, and examples thereof include an ethynyl group, a propargyl group, a 3-butyn-2-yl group, a 2-methyl-3-butyn-2-yl group, a 2-butynyl group, a 3-butynyl group, a 2-pentynyl group, a 3-pentynyl group, a 4-pentynyl group, a 1-hexynyl group, a 5-hexynyl group, a fluoroethynyl group, a 3-chloro-2-propynyl group, a 3-bromo-2-propynyl group, a 3-iodo-2-propynyl group, a 3-chloro-1-propynyl group, a 5-chloro-4-pentynyl group, a 3,3,3-trifluoro-1-propynyl group, and a 3-fluoro-2-propynyl group.

Examples of the C3-C6 cycloalkyl group include a cyclopropyl group, a cyclobutyl group, a cyclopentyl group, and a cyclohexyl group.

The C3-C6 cycloalkyl group optionally having one or more halogen atoms represents a group in which one or more hydrogen atoms of a C3-C6 cycloalkyl group are optionally substituted with a halogen atom, and examples thereof include a cyclopropyl group, a cyclobutyl group, a cyclopentyl group, a cyclohexyl group, a 2-fluorocyclopropyl group, a 2,2-difluorocyclopropyl group, a 2-chloro-2-fluorocyclopropyl group, a 2,2-dichlorocyclopropyl group, a 2,2-dibromocyclopropyl group, a 2,2,3,3-tetrafluorocyclobutyl group, a 2-chlorocyclohexyl group, a 4,4-difluorocyclohexyl group, and a 4-chlorocyclohexyl group.

Examples of the C3-C4 cycloalkyl group include a cyclopropyl group and a cyclobutyl group.

The C3-C4 cycloalkyl group optionally having one or more halogen atoms represents a group in which one or more hydrogen atoms of a C3-C4 cycloalkyl group are optionally substituted with a halogen atom, and examples thereof include a cyclopropyl group, a cyclobutyl group, a 2-fluorocyclopropyl group, a 2,2-difluorocyclopropyl group, a 2,2-dichlorocyclopropyl group, and a 2,2-dibromocyclopropyl group.

Examples of the C1-C3 alkoxy group include a methoxy group, an ethoxy group, a propoxy group, and an isopropoxy group.

Examples of the C1-C6 alkoxy group include a methoxy group, an ethoxy group, an isopropoxy group, a butoxy group, a tert-butoxy group, a neopentyloxy group, and a hexyloxy group.

Examples of the C1-C6 alkoxy group optionally having one or more halogen atoms represents a group in which one or more hydrogen atoms of a C1-C6 alkoxy group are optionally substituted with a halogen atom, and examples thereof include a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a 1-methylbutoxy group, a 1-ethylpropoxy group, a 2-methylbutoxy group, a hexyloxy group, a trifluoromethoxy group, a difluoromethoxy group, a pentafluoroethoxy group, a 2,2,2-trifluoroethoxy group, and a heptafluoropropoxy group.

Examples of the C1-C4 alkoxy group include a methoxy group, an ethoxy group, a propoxy group, and a tert-butoxy group.

The C1-C4 alkoxy group optionally having one or more halogen atoms represents a group in which one or more hydrogen atoms of a C1-C4 alkoxy group are optionally substituted with a halogen atom, and examples thereof include a methoxy group, an ethoxy group, a propoxy group, an isopropoxy group, a butoxy group, an isobutoxy group, a sec-butoxy group, a tert-butoxy group, a trifluoromethoxy group, a difluoromethoxy group, a pentafluoroethoxy group, and a 3,3,3-trifluoropropoxy group.

Examples of the C1-C6 alkylthio group include a methylthio group, an ethylthio group, an isopropylthio group, a tert-butylthio group, and a hexylthio group.

The C1-C6 alkylthio group optionally having one or more halogen atoms represents a group in which at least one hydrogen atom of a C1-C6 alkylthio group is optionally substituted with a halogen atom, and examples thereof include a methylthio group, an ethylthio group, a propylthio group, an isopropylthio group, a butylthio group, a sec-butylthio group, a tert-butylthio group, a pentylthio group, an isopentylthio group, a neopentylthio group, a hexylthio group, an isohexylthio group, a sec-hexylthio group, a fluoromethylthio group, a difluoromethylthio group, a trifluoromethylthio group, a pentafluoroethylthio group, a 2,2,2-trifluoroethylthio group and a 3,3,3-trifluoropropylthio group.

Examples of the C1-C4 alkylthio group include a methylthio group, an ethylthio group, an isopropylthio group, and a tert-butylthio group.

The C1-C4 alkylthio group optionally having one or more halogen atoms represents a group in which one or more hydrogen atoms of a C1-C4 alkylthio group are optionally substituted with a halogen atom, and examples thereof include a methylthio group, an ethylthio group, a propylthio group, an isopropylthio group, a butylthio group, an isobutylthio group, a tert-butylthio group, a fluoromethylthio group, a difluoromethylthio group, a trifluoromethylthio group, a pentafluoroethylthio group, and a 2,2,2-trifluoroethylthio group.

Examples of the C1-C3 alkylthio group include a methylthio group, an ethylthio group, a propylthio group, and an isopropylthio group.

The C1-C3 alkylthio group optionally having one or more halogen atoms represents a group in which one or more hydrogen atoms of a C1-C3 alkylthio group are optionally substituted with a halogen atom, and examples thereof include a methylthio group, an ethylthio group, a propylthio group, an isopropylthio group, a fluoromethylthio group, a difluoromethylthio group, a trifluoromethylthio group, a pentafluoroethylthio group, and a 2,2,2-trifluoroethylthio group.

Examples of the C3-C6 cycloalkyloxy group include a cyclopropyloxy group, a cyclopentyloxy group, and a cyclohexyloxy group.

The C3-C6 cycloalkyloxy group optionally having one or more halogen atoms represents a group in which one or more hydrogen atoms of a C3-C6 cycloalkyloxy group are optionally substituted with a halogen atom, and examples thereof include a cyclopropyloxy group, a cyclobutyloxy group, a cyclopentyloxy group, a cyclohexyloxy group, a 2-fluorocyclopropyloxy group, a 2,2-difluorocyclopropyloxy group, a 2-chloro-2-fluorocyclopropyloxy group, a 2,2-dichlorocyclopropyloxy group, a 2,2-dibromocyclopropyloxy group, a 1-(trifluoromethyl)cyclopropyloxy group, a 2,2,3,3-tetrafluorocyclobutyloxy group, a 2-chlorocyclohexyloxy group, a 4,4-difluorocyclohexyloxy group, and a 4-chlorocyclohexyloxy group.

Examples of the C3-C6 cycloalkylthio group include a cyclopropylthio group, a cyclopentylthio group, and a cyclohexylthio group.

The C3-C6 cycloalkylthio group optionally having one or more halogen atoms represents a group in which one or more hydrogen atoms of a C3-C6 cycloalkylthio group are optionally substituted with a halogen atom, and examples thereof include a cyclopropylthio group, a 2,2-difluorocyclopropylthio group, a cyclobutylthio group, a cyclopentylthio group, and a cyclohexylthio group.

The C4-C10 cycloalkylalkoxy group represents a group in which the total number of carbon atoms of the cycloalkyl moiety and the alkoxy moiety is within a range of 4 to 10, and examples thereof include a cyclopropylmethoxy group, a 1-cyclopropylethoxy group, a 3-cyclopropylpropyloxy group, a cyclopentylmethoxy group, a 2-cyclopentylethoxy group, a cyclohexylmethoxy group, a 2-cyclohexylethoxy group, and a cycloheptylmethoxy group.

Examples of the C3-C6 alkenyloxy group include a 2-propenyloxy group, a 3-butenyloxy group, a 1-methyl-3-butenyloxy group, and a 5-hexenyloxy group.

The C3-C6 alkenyloxy group optionally having one or more halogen atoms represents a group in which one or more hydrogen atoms of a C3-C6 alkenyloxy group are optionally substituted with a halogen atom, and examples thereof include a 2-propenyloxy group, a 2-butenyloxy group, a 1-methyl-2-propenyloxy group, a 3-butenyloxy group, a 2-methyl-2-propenyloxy group, a 2-pentenyloxy group, a 3-pentenyloxy group, a 4-pentenyloxy group, a 1-methyl-3- butenyloxy group, a 4,4,4-trifluoro-2-butenyloxy group, and a 5-bromo-4,5,5-trifluoro-4-trifluoromethyl-2-pentenyloxy group.

Examples of the C3-C6 alkynyloxy group include a propargyloxy group, a 3-butyn-2-yloxy group, and a 5-hexenyloxy group.

The C3-C6 alkynyloxy group optionally having one or more halogen atoms represents a group in which one or more hydrogen atoms of a C3-C6 alkynyloxy group are optionally substituted with a halogen atom, and examples thereof include a propargyloxy group, a 1-butyn-3-yloxy group, a 2-methyl-3-butyn-2-yloxy group, a 2-butynyloxy group, a 3-butynyloxy group, a 2-pentynyloxy group, a 3-pentynyloxy group, a 4-pentynyloxy group, a 5-hexynyloxy group, a 3-chloro-2-propynyloxy group, a 3-bromo-2-propynyloxy group, and a 3-iodo-2-propynyloxy group.

Examples of the C3-C6 alkenylthio group include a 2-propenylthio group, a 2-butenylthio group, a 1,2-dimethyl-2-propenylthio group, and a 5-hexenylthio group.

The C3-C6 alkenylthio group optionally having one or more halogen atoms represents a group in which one or more hydrogen atoms of a C3-C6 alkenylthio group are optionally substituted with a halogen atom, and examples thereof include a 2-propenylthio group, a 2-butenylthio group, a 1-methyl-2-propenylthio group, a 3-butenylthio group, a 2-methyl-2-propenylthio group, a 2-pentenylthio group, a 3-pentenylthio group, a 4-pentenylthio group, a 1-methyl-3-butenylthio group, a 4,4,4-trifluoro-2-butenylthio group, and a 5-bromo-4,5,5-trifluoro-4-trifluoromethyl-2-pentenylthio group.

Examples of the C3-C6 alkynylthio group include a propargylthio group, a 3-methyl-1-butyn-3-ylthio group, and a 5-hexynylthio group.

The C3-C6 alkynylthio group optionally having one or more halogen atoms represents a group in which one or more hydrogen atoms of a C3-C6 alkynylthio group are optionally substituted with a halogen atom, and examples thereof include a propargylthio group, a 3-butyn-2-ylthio group, a 2-methyl-3-butyn-2-ylthio group, a 2-butynylthio group, a 3-butynylthio group, a 2-pentynylthio group, a 3-pentynylthio group, a 4-pentynylthio group, a 5-hexynylthio group, a 3-chloro-2-propynylthio group, a 3-bromo-2-propynylthio group, and a 3-iodo-2-propynylthio group.

The C2-C6 alkoxycarbonyl group represents a group in which a C1-C5 alkoxy group and a carbonyl group are bound to each other, and examples thereof include a methoxycarbonyl group, an ethoxycarbonyl group, a propoxycarbonyl group, an isopropoxycarbonyl group, a butoxycarbonyl group, a tert-butoxycarbonyl group, a neopentyloxycarbonyl group, and a 2-methylbutoxycarbonyl group.

The aminocarbonyl group optionally having one or more C1-C6 alkyl groups represents an aminocarbonyl group in which one or two hydrogen atoms on nitrogen are optionally substituted with the same or different C1-C6 alkyl group(s), and examples thereof include an aminocarbonyl group, a methylaminocarbonyl group, an ethylaminocarbonyl group, a butylaminocarbonyl group, a dimethylaminocarbonyl group, a diethylaminocarbonyl group, a dipropylaminocarbonyl group, a diisopropylaminocarbonyl group, a hexylaminocarbonyl group, and an N-methyl-N-ethylaminocarbonyl group.

The phenyl group optionally having one or more atoms or groups selected from Group $P^1$ represents a phenyl group in which hydrogen atoms of a phenyl group are optionally substituted with one or more atoms or groups selected from Group $P^1$ and, when the number of atoms or groups selected from Group $P^1$ is 2 or more, those atoms or groups may be the same or different to each other. Examples of the phenyl group optionally having one or more atoms or groups selected from Group $P^1$ include a phenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 4-methylphenyl group, a 4-trifluoromethylphenyl group, a 4-methoxyphenyl group, a 4-methylthiophenyl group, a 2-cyanophenyl group, a 3-cyanophenyl group, a 4-cyanophenyl group, a 2,4-difluorophenyl group, a 2,5-difluorophenyl group, a 2,6-difluorophenyl group, a 3,5-difluorophenyl group, a 2,4-dichlorophenyl group, a 2,5-dichlorophenyl group, a 2,6-dichlorophenyl group, a 3,5-dichlorophenyl group, a 2,4,6-trifluorophenyl group, a pentafluorophenyl group, a 2-chloro-4-fluorophenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 2-fluoro-4-methylphenyl group, a 2-cyclopropylphenyl group, a 2-ethylphenyl group, a 2-butylphenyl group, a 3-cyclopropylphenyl group, a 4-cyclopropylphenyl group, a 2-methylthiophenyl group, a 3-methylthiophenyl group, and a 4-methylthiophenyl group.

The phenyl group optionally having one or more atoms or groups selected from Group $P^3$ represents a phenyl group in which hydrogen atoms of a phenyl group are optionally substituted with one or more atoms or groups selected from Group $P^3$ and, when the number of atoms or groups selected from Group $P^3$ is 2 or more, those atoms or groups may be the same or different to each other. Examples of the phenyl group optionally having one or more atoms or groups selected from Group $P^3$ include a phenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 4-methylphenyl group, a 4-trifluoromethylphenyl group, a 4-methoxyphenyl group, a 4-methylthiophenyl group, a 2-cyanophenyl group, a 3-cyanophenyl group, a 4-cyanophenyl group, a 2,4-difluorophenyl group, a 2,5-difluorophenyl group, a 2,6-difluorophenyl group, a 3,5-difluorophenyl group, a 2,4-dichlorophenyl group, a 2,5-dichlorophenyl group, a 2,6-dichlorophenyl group, a 3,5-dichlorophenyl group, a 2,4,6-trifluorophenyl group, a pentafluorophenyl group, a 2-chloro-4-fluorophenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 2-fluoro-4-methylphenyl group, a 2-cyclopropylphenyl group, a 2-ethylphenyl group, a 3-cyclopropylphenyl group, a 4-cyclopropylphenyl group, a 2-methylthiophenyl group, a 3-methylthiophenyl group, and a 4-methylthiophenyl group.

The benzyl group optionally having one or more atoms or groups selected from Group $P^3$ represents a group in which hydrogen atoms of the phenyl moiety are optionally substituted with one or more atoms or groups selected from Group $P^3$ and, when the number of atoms or groups selected from Group $P^3$ is 2 or more, those atoms or groups may be the same or different to each other. Examples of the benzyl group optionally having one or more atoms or groups selected from Group $P^3$ include a benzyl group, a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group, a 4-bromobenzyl group, a 2-iodobenzyl group, a 4-methylbenzyl group, a 4-trifluoromethylbenzyl group, a 4-methoxybenzyl group, a 4-methylthiobenzyl group, a 2-cyanobenzyl group, a 3-cyanobenzyl group, a 4-cyanobenzyl group, a 2,4-difluorobenzyl group, a 2,5-difluorobenzyl group, a 2,6-difluorobenzyl group, a 3,5-difluorobenzyl group, a 2,4,6-trifluorobenzyl group, a 2,3,4,5,6-pentafluorobenzyl group, a 2-chloro-4-fluorobenzyl group, a 3,4,5-trifluorobenzyl group, a 2,3-dimethylbenzyl group, a 2,4-dimethylbenzyl group, a 2,5-dimethylbenzyl group, a 2,6-dimethylbenzyl group, a 3,4-dimethylbenzyl group, a 3,5-dimethylbenzyl group, a 2-fluoro-4-methylbenzyl group, a 2-cyclopropylbenzyl group, a 2-ethylbenzyl group, a 2-propylbenzyl group, a 3-cyclopropylbenzyl group, a 4-cyclopropylbenzyl group, a 2-methylthiobenzyl group, a 3-methylthiobenzyl group, and a 4-methylthiobenzyl group.

The phenyl group optionally having one or more halogen atoms represents a phenyl group in which hydrogen atoms of a phenyl group are optionally substituted with one or more halogen atoms and, when substituted with two or more halogen atoms, those atoms may be the same or different to each other. Examples of the phenyl group optionally having one or more halogen atoms include a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2,4-difluorophenyl group, a 2,5-difluorophenyl group, a 2,6-difluorophenyl group, a 3,5-difluorophenyl group, a 2,4-dichlorophenyl group, a 2,5-dichlorophenyl group, a 2,6-dichlorophenyl group, a 3,5-dichlorophenyl group, a 2,4,6-trifluorophenyl group, a pentafluorophenyl group, a 2-chloro-4-fluorophenyl group, and a 3,4,5-trifluorophenyl group.

Examples of the C6-C16 aryloxy group include a phenoxy group, a naphthyloxy group, and an anthryloxy group.

The C6-C16 aryloxy group optionally having one or more atoms or groups selected from Group $P^2$ represents a C6-C16 aryloxy group in which hydrogen atoms of a C6-C16 aryloxy group are optionally substituted with one or more atoms or groups selected from Group $P^2$ and, when the number of atoms and groups selected from Group $P^2$ is 2 or more, those atoms and groups may be the same or different to each other. Examples of the C6-C16 aryloxy group optionally having one or more atoms or groups selected from Group $P^2$ include a phenoxy group, a 1-naphthyloxy group, a 2-naphthyloxy group, a 1-acenaphthyloxy group, a 1-phenanthryloxy group, a 9-anthryloxy group, a 1-pyrenyloxy group, a 2-fluorophenoxy group, a 3-fluorophenoxy group, a 4-fluorophenoxy group, a 2-chlorophenoxy group, a 3-chlorophenoxy group, a 4-chlorophenoxy group, a 2-bromophenoxy group, a 3-bromophenoxy group, a 4-bromophenoxy group, a 2-iodophenoxy group, a 3-iodophenoxy group, a 4-iodophenoxy group, a 2,4-difluorophenoxy group, a 2,5-dichlorophenoxy group, a 2,4,6-trifluorophenoxy group, a pentafluorophenoxy group, a 2-fluoro-1-naphthyloxy group, a 3-chloro-1-naphthyloxy group, a 2-methylphenoxy group, a 3-methylphenoxy group, a 4-methylphenoxy group, a 2-methoxyphenoxy group, a 3-methoxyphenoxy group, a 4-methoxyphenoxy group, a 2-methylthiophenoxy group, a 3-methylthiophenoxy group, a 4-methylthiophenoxy group, a 2-cyanophenoxy group, a 3-cyanophenoxy group, and a 4-cyanophenoxy group.

Examples of the C6-C16 arylthio group include a phenylthio group, a naphthylthio group, and an anthrylthio group.

The C6-C16 arylthio group optionally having one or more atoms or groups selected from Group $P^2$ represents a C6-C16 arylthio group in which hydrogen atoms of a C6-C16 arylthio group are optionally substituted with one or more atoms or groups selected from Group $P^2$ and, when the number of atoms and groups selected from Group $P^2$ is 2 or more, those atoms and groups may be the same or different to each other. Examples of the C6-C16 arylthio group optionally having one or more atoms or groups selected from Group $P^2$ include a phenylthio group, a 1-naphthylthio group, a 2-naphthylthio group, a 1-acenaphthylthio group, a 1-phenanthrylthio group, a 9-anthrylthio group, a 1-pyrenylthio group, a 2-fluorophenylthio group, a 3-fluorophenylthio group, a 4-fluorophenylthio group, a 2-chlorophenylthio group, a 3-chlorophenylthio group, a 4-chlorophenylthio group, a 2-bromophenylthio group, a 3-bromophenylthio group, a 4-bromophenylthio group, a 2-iodophenylthio group, a 3-iodophenylthio group, a 4-iodophenylthio group, a 2,4-difluorophenylthio group, a 2,5-dichlorophenylthio group, a 2-chloro-4-fluorophenylthio group, a 3-chloro-4-fluorophenylthio group, a 2-methylphenylthio group, a 3-methylphenylthio group, a 4-methylphenylthio group, a 2-methoxyphenylthio group, a 3-methoxyphenylthio group, a 4-methoxyphenylthio group, a 2-methylthiophenylthio group, a 3-methylthiophenylthio group, a 4-methylthiophenylthio group, a 2-cyanophenylthio group, a 3-cyanophenylthio group, a 4-cyanophenylthio group, a 3-fluoro-1-naphthylthio group, and a 4-chloro-1-naphthylthio group.

The C7-C18 aralkyl group represents a group in which the total number of carbon atoms of the alkyl moiety and the aryl moiety is within a range of 7 to 18, and examples thereof include a benzyl group, a 2-phenylethyl group, a 11-phenylundecyl group, and a 1-anthrylmethyl group.

The C7-C18 aralkyl group optionally having one or more atoms or groups selected from Group $P^2$ represents a C7-C18 aralkyl group in which hydrogen atoms of the alkyl moiety and the aryl moiety of a C7-C18 aralkyl group are optionally substituted with one or more atoms or groups selected from Group $P^2$ and, when the number of atoms and groups selected from Group $P^2$ is 2 or more, those atoms and groups may be the same or different to each other. Examples of the C7-C18 aralkyl group optionally having one or more atoms or groups selected from Group $P^2$ include a benzyl group, a 2-phenylethyl group, a 3-phenylpropyl group, a 4-phenylbutyl group, a 12-phenyldodecyl group, a 1-methoxy-2-phenylethyl group, a 1-naphthylmethyl group, a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group, a 4-bromobenzyl group, a 2-iodobenzyl group, a 3-iodobenzyl group, a 4-iodobenzyl group, a 2-methylbenzyl group, a 3-methylbenzyl group, a 4-methylbenzyl group, a 2-methoxybenzyl group, a 3-methoxybenzyl group, a 4-methoxybenzyl group, a 2-cyanobenzyl group, a 3-cyanobenzyl group, a 4-cyanobenzyl group, a 2,4-difluorobenzyl group, a 2,5-dichlorobenzyl group, a 2,4,6-trifluorobenzyl group, a pentafluorobenzyl group, a 2-(4-bromophenyl)ethyl group, a 3-(4-iodophenyl)propyl group, a 4-(4-fluorophenyl)butyl group, and a methoxy(phenyl)methyl group.

The C7-C18 aralkyl group optionally having one or more atoms or groups selected from Group $P^1$ represents a C7-C18 aralkyl group in which hydrogen atoms of the alkyl moiety and the aryl moiety of a C7-C18 aralkyl group are optionally substituted with one or more atoms or groups selected from Group $P^1$ and, when the number of atoms and groups selected from Group $P^1$ is 2 or more, those atoms and groups may be the same or different to each other. Examples of the C7-C18 aralkyl group optionally having one or more atoms or groups selected from Group $P^1$ include a benzyl group, a 2-phenylethyl group, a 3-phenylpropyl group, a 4-phenylbutyl group, a 12-phenyldodecyl group, a 1-methoxy-2-phenylethyl group, a 1-naphthylmethyl group, a 2-(1-naphthyl)ethyl group, a 3-(1-naphthyl)propyl group, a 4-(1-naphthyl)butyl group, a 2-naphthylmethyl group, a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group, a 4-bromobenzyl group, a 2-iodobenzyl group, a 3-iodobenzyl group, a 4-iodobenzyl group, a 2-methylbenzyl group, a 3-methylbenzyl group, a 4-methylbenzyl group, a 2-methoxybenzyl group, a 3-methoxybenzyl group, a 4-methoxybenzyl group, a 2-cyanobenzyl group, a 3-cyanobenzyl group, a 4-cyanobenzyl group, a 2,4-difluorobenzyl group, a 2,5-dichlorobenzyl group, a 2,4,6-trifluorobenzyl group, a 2,3,4-trichlorobenzyl group, a pentafluorobenzyl group, a 2-bromo-3-fluorobenzyl group, a 2-chloro-4-fluorobenzyl group, a 2-(4-bromophenyl)ethyl group, a 3-(4-iodophenyl)propyl group, a 4-(4-fluorophenyl)butyl group, and a 1-methoxy-1-phenylmethyl group.

The C7-C18 aralkyl group optionally having one or more atoms or groups selected from Group $P^3$ represents a C7-C18 aralkyl group in which hydrogen atoms of the alkyl moiety and the aryl moiety of a C7-C18 aralkyl group are optionally substituted with one or more atoms or groups selected from Group $P^3$ and, when the number of atoms and groups selected from Group $P^3$ is 2 or more, those atoms and groups may be the same or different to each other. Examples of the C7-C18 aralkyl group optionally having one or more atoms or groups selected from Group $P^3$ include a benzyl group, a 2-phenylethyl group, a 3-phenylpropyl group, a 4-phenylbutyl group, a 12-phenyldodecyl group, a 1-methoxy-2-phenylethyl group, a 1-naphthylmethyl group, a 2-(1-naphthyl)ethyl group, a 3-(1-naphthyl)propyl group, a 4-(1-naphthyl)butyl group, a 2-naphthylmethyl group, a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group, a 4-bromobenzyl group, a 2-iodobenzyl group, a 3-iodobenzyl group, a 4-iodobenzyl group, a 2-methylbenzyl group, a 3-methylbenzyl group, a 4-methylbenzyl group, a 2-methoxybenzyl group, a 3-methoxybenzyl group, a 4-methoxybenzyl group, a 2-cyanobenzyl group, a 3-cyanobenzyl group, a 4-cyanobenzyl group, a 2,4-difluorobenzyl group, a 2,5-dichlorobenzyl group, a 2,4,6-trifluorobenzyl group, a 2,3,4-trichlorobenzyl group, a pentafluorobenzyl group, a 2-bromo-3-fluorobenzyl group, a 2-chloro-4-fluorobenzyl group, a 2-(4-bromophenyl)ethyl group, a 3-(4-iodophenyl)propyl group, a 4-(4-fluorophenyl)butyl group, and a 1-methoxy-1-phenylmethyl group.

The C7-C18 aralkyloxy group represents a group in which the total number of carbon atoms of the aryl moiety and the alkoxy moiety is within a range of 7 to 18, and examples thereof include a benzyloxy group, a 2-phenylethoxy group, a 11-phenylundecyloxy group, and a 1-anthrylmethoxy group.

The C7-C18 aralkyloxy group optionally having one or more atoms or groups selected from Group $P^2$ represents a C7-C18 aralkyloxy group in which hydrogen atoms of the alkoxy moiety and the aryl moiety are optionally substituted with one or more atoms or groups selected from Group $P^2$ and, when the number of atoms and groups selected from Group $P^2$ is 2 or more, those atoms and groups may be the same or different to each other. Examples of the C7-C18 aralkyloxy group optionally having one or more atoms or groups selected from Group $P^2$ include a benzyloxy group, a 2-phenylethoxy group, a 3-phenylpropoxy group, a 4-phenylbutoxy group, a 12-phenyldodecyloxy group, a naphthylmethoxy group, a naphthylethoxy group, a 4-fluorobenzyloxy group, a 2-chlorobenzyloxy group, a 3-bromobenzyloxy group, a 4-iodobenzyloxy group, a 2-methylbenzyloxy group, a 3-methylbenzyloxy group, a 4-methylbenzyloxy group, a 2-methoxybenzyloxy group, a 3-methoxybenzyloxy group, a 4-methoxybenzyloxy group, a 2-cyanobenzyloxy group, a 3-cyanobenzyloxy group, a 4-cyanobenzyloxy group, a 2,4-difluorobenzyloxy group, a 2,5-dichlorobenzyloxy group, a 3,4,5-trifluorobenzyloxy group, a 2,3,4-trichlorobenzyloxy group, a pentafluorobenzyloxy group, a 6-chloro-2-fluorobenzyloxy group, a 2-(4-fluorophenyl)ethoxyethoxy group, a 2-(3-chlorophenyl)ethoxy group, a 2-(2-bromophenyl)ethoxy group, and a 1,1-difluoro-1-phenylmethoxy group.

The C7-C16 aryloxyalkyl group represents a group in which the total number of carbon atoms of the aryloxy moiety and the alkyl moiety is within a range of 7 to 16, and examples thereof include a phenoxymethyl group, a 1-naphthyloxymethyl group, and a naphthyloxyethyl group.

The C7-C16 aryloxyalkyl group optionally having one or more atoms or groups selected from Group $P^2$ represents a C7-C16 aryloxyalkyl group in which hydrogen atoms of the aryloxy moiety and the alkyl moiety are optionally substituted with one or more atoms or groups selected from Group $P^2$ and, when the number of atoms and groups selected from Group $P^2$ is 2 or more, those atoms and groups may be the same or different to each other. Examples of the C7-C16 aryloxyalkyl group optionally having one or more atoms or groups selected from Group $P^2$ include a phenoxymethyl group, a 1-naphthyloxymethyl group, a 2-naphthyloxymethyl group, a (3-fluorophenoxy)methyl group, a (4-fluorophenoxy)methyl group, a (2-chlorophenoxy)methyl group, a (3-chlorophenoxy)methyl group, a (4-chlorophenoxy)methyl group, a phenoxyethyl group, a (2-cyanophenoxy)methyl group, a (2-methoxyphenoxy)methyl group, a (2-trifluoromethylphenoxy)methyl group, a (2-cyano-4-methylphenoxy)methyl group, and a naphthyloxyethyl group.

The anilino group optionally having one or more atoms or groups selected from Group $P^2$ represents an anilino group in which hydrogen atoms on phenyl and/or hydrogen atoms on nitrogen are optionally substituted with one or more atoms or groups selected from Group $P^2$ and, when the number of atoms and groups selected from Group $P^2$ is 2 or more, those atoms and groups may be the same or different to each other. Examples of the anilino group optionally having one or more atoms or groups selected from Group $P^2$ include an anilino group, an N-methylanilino group, an N-ethyl-anilino group, an N-methyl-2-fluoroanilino group, an N-methyl-3-fluoroanilino group, an N-methyl-4-fluoroanilino group, an N-methyl-4-chloroanilino group, an N,4-dimethylanilino group, and an N-methyl-4-cyanoanilino group.

The heteroaryl moiety in a C2-C9 heteroaryloxy group is a 5-membered ring, a 6-membered ring, a fused ring of a 5-membered ring and a 5-membered ring, a fused ring of a 5-membered ring and a 6-membered ring, or a fused ring of a 6-membered ring and a 6-membered ring, and examples of the C2-C9 heteroaryloxy group include a 2-pyrazolyloxy group, a 2-pyridyloxy group, a 2-benzoxazolyloxy group, a 1H-imidazo[1,2-b]pyrazol-6-yloxy group, and a 2-quinolyloxy group.

The C2-C9 heteroaryloxy group optionally having one or more atoms or groups selected from Group $P^2$, wherein heteroaryl moiety is a 5-membered ring, a 6-membered ring, a fused ring of a 5-membered ring and a 5-membered ring, a fused ring of a 5-membered ring and a 6-membered ring, or a fused ring of a 6-membered ring and a 6-membered ring represents a group in which hydrogen atoms of a C2-C9 heteroaryloxy group are optionally substituted with one or more atoms or groups selected from Group $P^2$ and, when the number of atoms and groups selected from Group $P^2$ is 2 or more, those atoms and groups may be the same or different to each other. Examples of the C2-C9 heteroaryloxy group optionally having one or more atoms or groups selected from Group $P^2$ include a 2-pyridyloxy group, a 3-pyridyloxy group, a 4-pyridyloxy group, a 2-pyrimidinyloxy group, a 3-methyl-2-pyridyloxy group, a 4-methyl-2-pyridyloxy group, a 5-methyl-2-pyridyloxy group, a 6-methyl-2-pyridyloxy group, a 6-cyano-2-pyridyloxy group, a 3-pyridazinyloxy group, a 2-pyrazinyloxy group, a 2-thiazolyloxy group, a 2-oxazolyloxy group, a 2-benzthiazolyloxy group, a 2-benzoxazolyloxy group, a 2-quinolyloxy group, a 2-pyrazolyloxy group, a 3-furyloxy group and a 3-thienyloxy group.

The C3-C9 trialkylsilyl group represents a group in which three hydrogen atoms on a silyl group are substituted with the same or different alkyl group(s), and examples thereof include a trimethylsilyl group, a tert-butyldimethylsilyl group, a triethylsilyl group, an isopropyldimethylsilyl group, and a triisopropylsilyl group.

Examples of the C1-C6 alkylsulfonyl group include a methylsulfonyl group, an ethylsulfonyl group, an isopropylsulfonyl group, a butylsulfonyl group, and a hexylsulfonyl group.

The C1-C6 alkylsulfonyl group optionally having one or more halogen atoms represents a group in which one or more hydrogen atoms of a C1-C6 alkylsulfonyl group are optionally substituted with a halogen atom and, when substituted with two or more halogen atoms, those atoms may be the same or different to each other. Examples of the C1-C6 alkylsulfonyl group optionally having one or more halogen atoms include a methylsulfonyl group, an ethylsulfonyl group, a propylsulfonyl group, an isopropylsulfonyl group, a butylsulfonyl group, an isobutylsulfonyl group, a sec-butylsulfonyl group, a hexylsulfonyl group, a trifluoromethylsulfonyl group, and a perbromohexylsulfonyl group.

Examples of the C1-C6 alkylsulfinyl group include a methylsulfinyl group, an ethylsulfinyl group, an isopropylsulfinyl group, a butylsulfinyl group, and a hexylsulfinyl group.

The C1-C6 alkylsulfinyl group optionally having one or more halogen atoms represents a group in which one or more hydrogen atoms of a C1-C6 alkylsulfinyl group are optionally substituted with a halogen atom and, when substituted with two or more halogen atoms, those atoms may be the same or different to each other. Examples of the C1-C6 alkylsulfinyl group optionally having one or more halogen atoms include a methylsulfinyl group, an ethylsulfinyl group, a propylsulfinyl group, an isopropylsulfinyl group, a butylsulfinyl group, an isobutylsulfinyl group, a sec-butylsulfinyl group, a pentylsulfinyl group, a hexylsulfinyl group, a trifluoromethylsulfinyl group, and a perfluorohexylsulfinyl group.

The C1-C8 alkylamino group optionally having one or more halogen atoms represents an amino group in which one and/or two hydrogen atom(s) on nitrogen are substituted with the same or different alkyl group(s), and examples thereof include a methylamino group, an ethylamino group, a propylamino group, an isopropylamino group, a butylamino group, a dimethylamino group, a diethylamino group, a dipropylamino group, a dibutylamino group, an ethyl(methyl)amino group, and a propyl(methyl)amino group.

The C2-C5 alkoxyalkyl group represents a group in which the total number of carbon atoms of the alkoxy moiety and the alkyl moiety is within a range of 2 to 5, and examples thereof include a methoxymethyl group, an ethoxymethyl group, a propoxymethyl group, an isopropoxymethyl group, a butoxymethyl group, a 2-methoxyethyl group, a 2-isopropoxyethyl group, a 3-ethoxypropyl group, and a 4-methoxybutyl group.

The C2-C5 alkylthioalkyl group represents a group in which the total number of carbon atoms of the alkylthio moiety and the alkyl moiety is within a range of 2 to 5, and examples thereof include a methylthiomethyl group, an ethylthiomethyl group, a propylthiomethyl group, an isopropylthiomethyl group, a butylthiomethyl group, a 2-methylthioethyl group, a 2-isopropylthioethyl group, a 3-ethylthiopropyl group, and a 4-methylthiobutyl group.

The C2-C6 alkylcarbonyl group represents a group in which a C1-C5 alkyl group and a carbonyl group are bound to each other, and examples thereof include an acetyl group, a propionyl group, a butyryl group, an isobutyryl group, a pivaloyl group, and a pentanoyl group.

The C2-C6 alkylcarbonyloxy group represents a group in which a C1-C5 alkyl group and a carbonyloxy group are bound to each other, and examples thereof include an acetoxy group, a propionyloxy group, a butyryloxy group, an isobutyryloxy group, a pentanoyloxy group, and a hexanoyloxy group.

The C2-C6 alkylcarbonylamino group represents a group in which a C1-C5 alkyl group and a carbonylamino group are bound to each other, and examples thereof include an acetamino group, a propionylamino group, a butyrylamino group, an isobutyrylamino group, a pentanoylamino group, and a hexanoylamino group.

The C7-C16 arylcarbonyl group optionally having one or more atoms or groups selected from Group $P^2$ represents a group in which the total number of carbon atoms of the aryl moiety and the carbonyl moiety is within a range of 7 to 16, and represents a group in which hydrogen atoms of an aryl group are optionally substituted with one or more atoms or groups selected from Group $P^2$ and, when the number of atoms and groups selected from Group $P^2$ is 2 or more, those atoms and groups may be the same or different to each other. Examples of the C7-C16 arylcarbonyl group optionally having one or more atoms or groups selected from Group $P^2$ include a benzoyl group, a 1-naphthylcarbonyl group, a 2-naphthylcarbonyl group, a 2-fluorobenzoyl group, a 3-fluorobenzoyl group, a 4-fluorobenzoyl group, a 2-chlorobenzoyl group, a 3-chlorobenzoyl group, a 4-chlorobenzoyl group, a 2-cyanobenzoyl group, a 3-cyanobenzoyl group, and a 4-cyanobenzoyl group.

Examples of the aspect of the present compound are compounds in which the substituent in formula (1) is shown below:
a compound in which A is a C7-C18 aralkyloxy group optionally having one or more atoms or groups selected from Group $P^3$;
a compound in which $R^1$ is a hydrogen atom;
a compound in which $R^2$ is a hydrogen atom;
a compound in which $R^4$ is a hydrogen atom;
a compound in which $R^5$ is a hydrogen atom;

a compound in which $R^6$ is a hydrogen atom;
a compound in which $R^3$ is a C1-C3 alkyl group optionally having one or more halogen atoms;
a compound in which $R^3$ is a C3-C4 cycloalkyl group;
a compound in which $R^3$ is a halogen atom;
a compound in which $R^3$ is a C1-C3 alkoxy group optionally having one or more halogen atoms;
a compound in which $R^3$ is a C1-C3 alkyl group optionally having one or more halogen atoms, a halogen atom, a C3-C4 cycloalkyl group, or a C1-C3 alkoxy group optionally having one or more halogen atoms;
a compound in which $R^3$ is a methyl group;
a compound in which $R^3$ is an ethyl group;
a compound in which $R^3$ is a cyclopropyl group;
a compound in which $R^3$ is a trifluoromethyl group;
a compound in which $R^3$ is a difluoromethyl group;
a compound in which $R^3$ is a chlorine atom;
a compound in which $R^3$ is a bromine atom;
a compound in which $R^3$ is an iodine atom;
a compound in which $R^3$ is a fluorine atom;
a compound in which $R^3$ is a methoxy group;
a compound in which $R^3$ is an ethoxy group;
a compound in which $R^7$ is a methyl group;
X is an oxygen atom; and
X is a sulfur atom.
[Aspect 1]
A compound of formula (1) in which Q is Q1; A is a group S1:

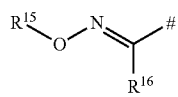

in which $R^{15}$, $R^{16}$, and # are the same as defined above; $R^1$, $R^2$, $R^4$, $R^5$, and $R^6$ are hydrogen atoms; $R^7$ is a C1-C3 alkyl group; and X is an oxygen atom.
A compound in which $R^3$ is a C1-C3 alkyl group optionally having one or more halogen atoms, a halogen atom, a C3-C4 cycloalkyl group, or a C1-C3 alkoxy group optionally having one or more halogen atoms in [Aspect 1].
A compound in which $R^3$ is a C1-C3 alkyl group optionally having one or more halogen atoms in [Aspect 1].
A compound in which $R^3$ is a halogen atom in [Aspect 1].
A compound in which $R^3$ is a C3-C4 cycloalkyl group in [Aspect 1].
A compound in which $R^3$ is a C1-C3 alkoxy group optionally having one or more halogen atoms in [Aspect 1].
[Aspect 2]
A compound of formula (1) in which Q is a group Q1:

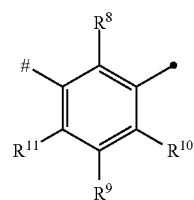

in which $R^8$, $R^9$, $R^{10}$, $R^{11}$, #, and ● are the same as defined above; A is a benzyloxy group (in which the benzyloxy group optionally has one or more atoms or groups selected from the group consisting of a halogen atom and a C1-C6 alkoxy group); $R^1$, $R^2$, $R^4$, $R^5$, and $R^6$ are hydrogen atoms; $R^7$ is a C1-C3 alkyl group; and X is an oxygen atom.
A compound in which $R^3$ is a C1-C3 alkyl group optionally having one or more halogen atoms, a halogen atom, a C3-C4 cycloalkyl group, or a C1-C3 alkoxy group optionally having one or more halogen atoms in [Aspect 2].
A compound in which $R^3$ is a C1-C3 alkyl group optionally having one or more halogen atoms in [Aspect 2].
A compound in which $R^3$ is a halogen atom in [Aspect 2].
A compound in which $R^3$ is a C3-C4 cycloalkyl group in [Aspect 2].
A compound in which $R^3$ is a C1-C3 alkoxy group optionally having one or more halogen atoms in [Aspect 2].
[Aspect 3]
A compound of formula (1) in which $R^1$, $R^2$, $R^4$, $R^5$, and $R^6$ are hydrogen atoms, $R^3$ is a C1-C3 alkyl group optionally having one or more halogen atoms, a C3-C4 cycloalkyl group, or a C1-C3 alkoxy group optionally having one or more halogen atoms, X is an oxygen atom, Q is a group Q1, $R^8$, $R^9$, $R^{10}$, and $R^{11}$ are the same or different and represent a hydrogen atom or a C1-C4 alkyl group, A is a group S1, a phenoxy group, a benzoyl group, an N-methylanilino group, or a benzyloxy group (in which the benzyloxy group optionally has one or more atoms or groups selected from the group consisting of a halogen atom and a C1-C6 alkoxy group), $R^{15}$ is a C1-C6 alkyl group optionally having one or more halogen atoms, a C2-C6 alkenyl group optionally having one or more halogen atoms, a C2-C6 alkynyl group optionally having one or more halogen atoms, a C7-C18 aralkyl group optionally having one or more atoms or groups selected from Group $P^1$, or a phenyl group optionally having one or more atoms or groups selected from Group $P^1$, $R^{16}$ is a C1-C6 alkyl group optionally having one or more halogen atoms, a C3-C6 cycloalkyl group optionally having one or more halogen atoms, or a phenyl group optionally having one or more halogen atoms.
A compound in which $R^3$ is a C1-C3 alkyl group optionally having one or more halogen atoms, Q is a group Q1, $R^8$, $R^9$, and $R^{11}$ are hydrogen atom, $R^{10}$ is a hydrogen atom or a C1-C4 alkyl group, A is a group S1, a phenoxy group, a benzoyl group, an N-methylanilino group, or a benzyloxy group (in which the benzyloxy group optionally has one or more atoms or groups selected from the group consisting of a halogen atom and a C1-C6 alkoxy group), $R^{15}$ is a C1-C6 alkyl group optionally having one or more halogen atoms, a C2-C6 alkenyl group, a C2-C6 alkynyl group, a benzyl group, a phenylethyl group (in which hydrogen atoms of a phenyl group of the phenylethyl group are optionally substituted with a C1-C4 alkyl group optionally having one or more halogen atoms), or a phenyl group, and $R^{16}$ is a C1-C6 alkyl group optionally having one or more halogen atoms, a C3-C6 cycloalkyl group, or a phenyl group in [Aspect 3].
A compound in which $R^3$ is a C1-C3 alkyl group optionally having one or more halogen atoms, Q is a group Q1, $R^8$, $R^9$, and $R^{11}$ are hydrogen atoms, $R^{10}$ is a hydrogen atom or a C1-C4 alkyl group, A is a group S1, $R^{15}$ is a C1-C6 alkyl group optionally having one or more halogen atoms, a C2-C6 alkenyl group, a C2-C6 alkynyl group, a benzyl group, a phenylethyl group (in which hydrogen atoms of a phenyl group of the phenylethyl group are optionally substituted with a C1-C4 alkyl group optionally having one or more halogen atoms), or a phenyl group, and $R^{16}$ is a C1-C6 alkyl group optionally having one or more halogen atoms, a C3-C6 cycloalkyl group, or a phenyl group in [Aspect 3].
A compound in which $R^3$ is a C1-C3 alkyl group optionally having one or more halogen atoms, Q is a group Q1, $R^8$, $R^9$, and $R^{11}$ are hydrogen atoms, $R^{10}$ is a hydrogen atom or a C1-C4 alkyl group, and A is a phenoxy group in [Aspect 3].

A compound in which $R^3$ is a C1-C3 alkyl group optionally having one or more halogen atoms, Q is a group Q1, $R^8$, $R^9$, and $R^{11}$ are hydrogen atoms, $R^{10}$ is a hydrogen atom or a C1-C4 alkyl group, and A is a benzoyl group in [Aspect 3].

A compound in which $R^3$ is a C1-C3 alkyl group optionally having one or more halogen atoms, Q is a group Q1, $R^8$, $R^9$, and $R^{11}$ are hydrogen atoms, $R^{10}$ is a hydrogen atom or a C1-C4 alkyl group, and A is an N-methylanilino group in [Aspect 3].

A compound in which $R^3$ is a C1-C3 alkyl group optionally having one or more halogen atoms, Q is a group Q1, $R^8$, $R^9$, and $R^{11}$ are hydrogen atoms, $R^{10}$ is a hydrogen atom or a C1-C4 alkyl group, and A is a benzyloxy group (in which the benzyloxy group optionally has one or more atoms or groups selected from the group consisting of a halogen atom and a C1-C6 alkoxy group) in [Aspect 3].

A compound in which $R^3$ is a C3-C4 cycloalkyl group, Q is a group Q1, $R^8$, $R^9$, and $R^{11}$ are hydrogen atoms, $R^{10}$ is a hydrogen atom or a C1-C4 alkyl group, A is a group S1, and $R^{15}$ and $R^{16}$ each is a C1-C6 alkyl group optionally having one or more halogen atoms in [Aspect 3].

A compound in which $R^3$ is a C1-C3 alkoxy group optionally having one or more halogen atoms, Q is a group Q1, $R^8$, $R^9$, and $R^{11}$ are hydrogen atoms, $R^{10}$ is a hydrogen atom or a C1-C4 alkyl group, A is a phenoxy group or a group S1, and $R^{15}$ and $R^{16}$ each is a C1-C6 alkyl group optionally having one or more halogen atoms in [Aspect 3].

A compound in which Q is a group Q1, $R^8$, $R^9$, and $R^{11}$ are hydrogen atoms, $R^{10}$ is a hydrogen atom or a C1-C4 alkyl group, A is a group S1, $R^{15}$ is a C1-C6 alkyl group optionally having one or more halogen atoms, a C2-C6 alkenyl group optionally having one or more halogen atoms, a C2-C6 alkynyl group optionally having one or more halogen atoms, a C7-C18 aralkyl group optionally having one or more atoms or groups selected from Group $P^1$, or a phenyl group optionally having one or more atoms or groups selected from Group $P^1$, and $R^{16}$ is a C1-C6 alkyl group optionally having one or more halogen atoms, a C3-C6 cycloalkyl group optionally having one or more halogen atoms, or a phenyl group optionally having one or more halogen atoms in [Aspect 3].

A compound in which Q is a group Q1, $R^8$, $R^9$, and $R^{11}$ are hydrogen atoms, $R^{10}$ is a hydrogen atom or a C1-C4 alkyl group, and A is a phenoxy group in [Aspect 3].

A compound in which Q is a group Q1, $R^8$, $R^9$, and $R^{11}$ are hydrogen atoms, $R^{10}$ is a hydrogen atom or a C1-C4 alkyl group, and A is a benzoyl group in [Aspect 3].

A compound in which Q is a group Q1, $R^8$, $R^9$, and $R^{11}$ are hydrogen atoms, $R^{10}$ is a hydrogen atom or a C1-C4 alkyl group, and A is an N-methylanilino group in [Aspect 3].

A compound in which Q is a group Q1, $R^8$, $R^9$, and $R^{11}$ are hydrogen atoms, $R^{10}$ is a hydrogen atom or a C1-C4 alkyl group, and A is a benzyloxy group (in which the benzyloxy group optionally has one or more atoms or groups selected from the group consisting of a halogen atom and a C1-C6 alkoxy group) in [Aspect 3].

A compound of formula (1), $R^1$, $R^2$, $R^4$, $R^5$ and $R^6$ are hydrogen atoms, $R^3$ is a C1-C3 alkyl group optionally having one or more halogen atoms, X is an oxygen atom, Q is a group Q2, $R^9$, $R^{10}$, and $R^{11}$ are hydrogen atoms, A is a group S1 or a phenoxy group, and $R^{15}$ and $R^{16}$ each is a C1-C6 alkyl group optionally having one or more halogen atoms.

In the present description, the structural formula of the compound may, for the sake of convenience, represent a certain form of an isomer, but the present invention includes all kinds of active isomers arising from the structure of the compound, such as a geometrical isomer, an optical isomer, a stereoisomer, and a tautomeric isomer, and a mixture thereof. Thus, it is not limited to the formula described for the sake of convenience, and can be any single isomer or a mixture thereof. Accordingly, the present compound may have an asymmetric carbon atom in the molecule and may potentially contain an optically active isomer and a racemic isomer, but the present invention is not particularly limited thereto, and includes any cases.

Next, a process for producing the present compound will be described.

The present compound can be produced, for example, by the following Production Processes.

(Production Process A)

The present compound represented by formula (1) (hereinafter referred to as the compound (1)) can be produced by reacting a compound represented by formula (A1) (hereinafter referred to as the compound (A1)) with a compound represented by formula (A2) (hereinafter referred to as the compound (A2)) in the presence of a base:

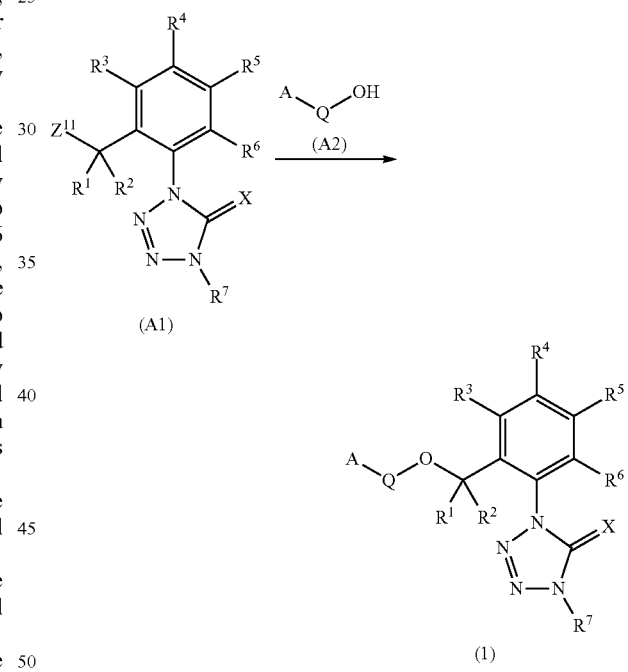

wherein $R^1$, $R^2$, $R^3$, $R^4$, $R^5$, $R^6$, $R^7$, X, A, and Q are the same as defined above, $Z^{11}$ is a leaving group such as a chlorine atom, a bromine atom, an iodine atom, a methanesulfonyloxy group, a trifluoromethanesulfonyloxy group, or a p-toluenesulfonyloxy group.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide;

ketones such as acetone, methyl ethyl ketone, and methyl isobutyl ketone; nitriles such as acetonitrile; water; and mixtures thereof.

Examples of the base to be used in the reaction include organic bases such as 4-dimethylaminopyridine and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (A2) is usually used in the proportion within a range of 1 to 10 mols, and the base is usually used in the proportion within a range of 0.5 to 5 mols, based on 1 mol of the compound (A1).

The reaction temperature of the reaction is usually within a range of −20 to 150° C. The reaction time of the reaction is usually within a range of 0.1 to 24 hours.

In the reaction, if necessary, sodium iodide, tetrabutylammonium iodide, and the like may be added, and these compounds are usually used in the proportion of 0.001 to 1.2 mols based on 1 mol of the compound (A1).

After completion of the reaction, the compound (1) can be isolated by performing post-treatment operations such as extraction of the reaction mixture with an organic solvent, and drying and concentration of the organic layer. The isolated present compound can be further purified by chromatography, recrystallization, and the like.

(Production Process B)

Among the compounds (1), a compound in which A is $A^1$ (hereinafter referred to as the compound (1-1)) can be produced by subjecting a compound represented by formula (B1) (hereinafter referred to as the compound (B1)) with a compound represented by formula (B2) (hereinafter referred to as the compound (B2)) to a coupling reaction in the presence of a base and a catalyst:

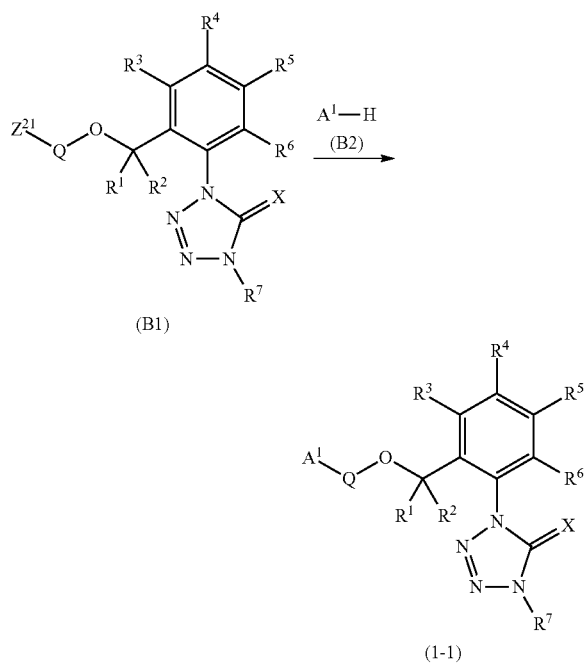

wherein $R^1$, $R^2$, $R^3$, $R^4$, $R^5$, $R^6$, $R^7$, X, and Q are the same as defined above, $A^1$ represents a C6-C16 aryloxy group optionally having one or more atoms or groups selected from Group $P^2$, a C2-C9 heteroaryloxy group optionally having one or more atoms or groups selected from Group $P^2$ (in which the heteroaryl moiety represents a 5-membered ring, a 6-membered ring, a fused ring of a 5-membered ring and a 6-membered ring, or a fused ring of a 6-membered ring and a 6-membered ring), or an anilino group optionally having one or more atoms or groups selected from Group $P^2$, and $Z^{21}$ represents a chlorine atom, a bromine atom, or an iodine atom.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; alcohols such as methanol, ethanol, propanol, and butanol; water; and mixtures thereof.

It is possible to usually use, as the compound (B2) to be used in the reaction, commercially available compounds. Specific examples thereof include phenol, 2-fluorophenol, aniline, N-methylaniline, and the like.

Examples of the catalyst to be used in the reaction include palladium(II) acetate/tricyclohexylphosphine, bis(diphenylphosphinoferrocenyl)palladium(II) dichloride, tris(dibenzylidineacetone)dipalladium/dicyclohexyl(2',4',6'-triisopropylbiphenyl-2-yl)phosphine or palladium(II) acetate/dicyclohexyl(2',4',6'-triisopropylbiphenyl-2-yl)phosphine, and the like.

Examples of the base to be used in the reaction include alkali metal phosphates such as tripotassium phosphate; and alkali metal alkoxides such as sodium methoxide, sodium ethoxide, sodium tert-butoxide, and potassium tert-butoxide.

In the reaction, the compound (B2) is usually used in the proportion within a range of 1 to 10 mols, the base is usually used in the proportion within a range of 1 to 10 mols, and the catalyst is usually used in the proportion within a range of 0.0001 to 1 mols, based on 1 mol of the compound (B1).

The reaction temperature of the reaction is usually within a range of 0 to 150° C. The reaction time of the reaction is usually within a range of 0.1 to 24 hours.

After completion of the reaction, the compound (1-1) can be isolated by performing post-treatment operations such as extraction of the reaction mixture with an organic solvent, and drying and concentration of the organic layer. The isolated present compound can be further purified by chromatography, recrystallization, and the like.

(Production Process C)

Among the compounds (1), a compound in which A is $A^2$ (hereinafter referred to as the compound (1-2)) can be produced by reacting a compound represented by formula (C1) (hereinafter referred to as the compound (C1)) with a compound represented by formula (C2) (hereinafter referred to as the compound (C2)) in the presence of a base:

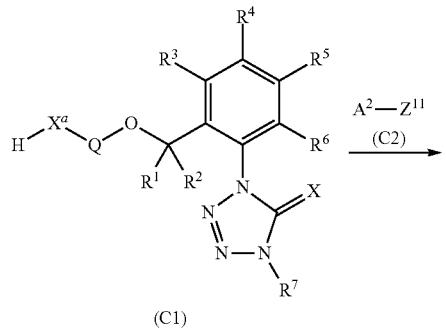

(C1)

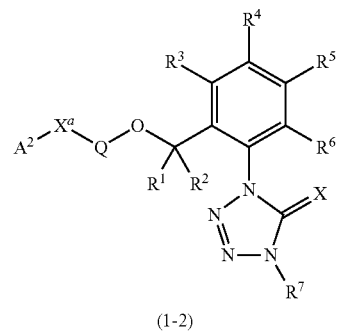

(1-2)

wherein $R^1$, $R^2$, $R^3$, $R^4$, $R^5$, $R^6$, $R^7$, X, $Z^{11}$, and Q are the same as defined above, $X^a$ represents an oxygen atom or a sulfur atom, and $A^2$ represents a C7-C18 aralkyl group optionally having one or more atoms or groups selected from Group $P^2$.

The reaction can be carried out in accordance with the reaction of Production Process A.

(Production Process D)

Among the compounds (1), a compound in which $R^7$ is a hydrogen atom (hereinafter referred to as the compound (1-3)) can be produced by reacting a compound represented by formula (D1) (hereinafter referred to as the compound (D1)) with an azidation agent:

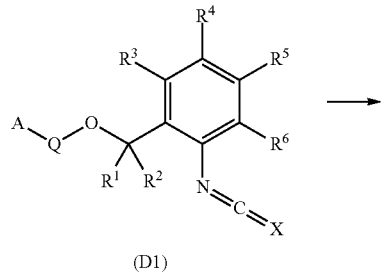

(D1)

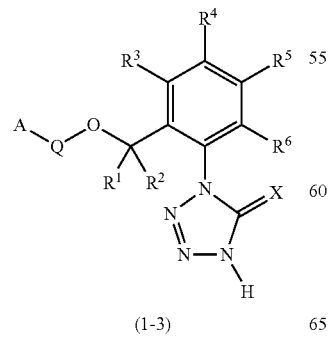

(1-3)

wherein $R^1$, $R^2$, $R^3$, $R^4$, $R^5$, $R^6$, X, A, and Q are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the azidation agent to be used in the reaction include inorganic azides such as sodium azide, barium azide, and lithium azide; and organic azides such as trimethylsilyl azide and diphenylphosphoryl azide.

In the reaction, the azidation agent is usually used in the proportion within a range of 1 to 10 mols based on 1 mol of the compound (D1).

The reaction temperature of the reaction is usually within a range of −20 to 150° C. The reaction time of the reaction is usually within a range of 0.1 to 24 hours.

In the reaction, if necessary, Lewis acid such as aluminum chloride or zinc chloride may be added, and these compounds are usually used in the proportion within a range of 0.05 to 5 mols based on 1 mol of the compound (D1).

After completion of the reaction, the compound (1-3) can be isolated by performing post-treatment operations such as extraction of the reaction mixture with an organic solvent, and drying and concentration of the organic layer. The isolated present compound can be further purified by chromatography, recrystallization, and the like.

(Production Process E)

The compound (1) can be produced by reacting the compound (1-3) with a compound represented by formula (E1) (hereinafter referred to as the compound (E1)) in the presence of a base:

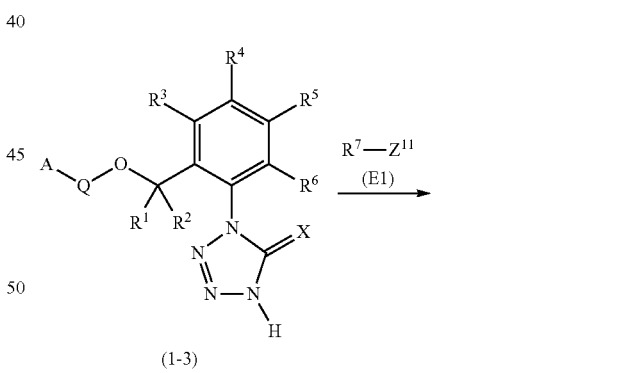

(1-3)

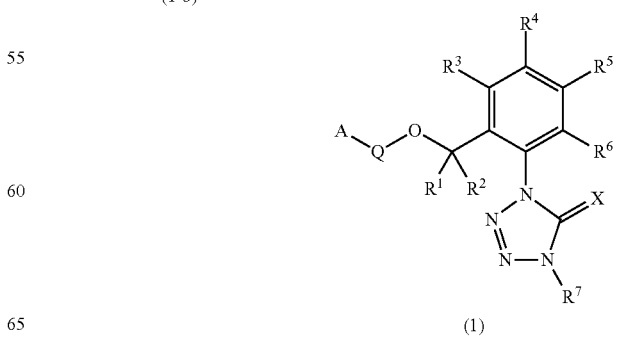

(1)

wherein $R^1$, $R^2$, $R^3$, $R^4$, $R^5$, $R^6$, $R^7$, X, $Z^{11}$, A, and Q are the same as defined above.

The reaction can be carried out in accordance with the reaction of Production Process A.

(Production Process F)

Among the compounds (1), a compound in which X is a sulfur atom (hereinafter referred to as the compound (1-S)) can be produced from a compound in which X is an oxygen atom (hereinafter referred to as the compound (1-O)) among the present compounds represented by formula (1) by a known sulfidation reaction:

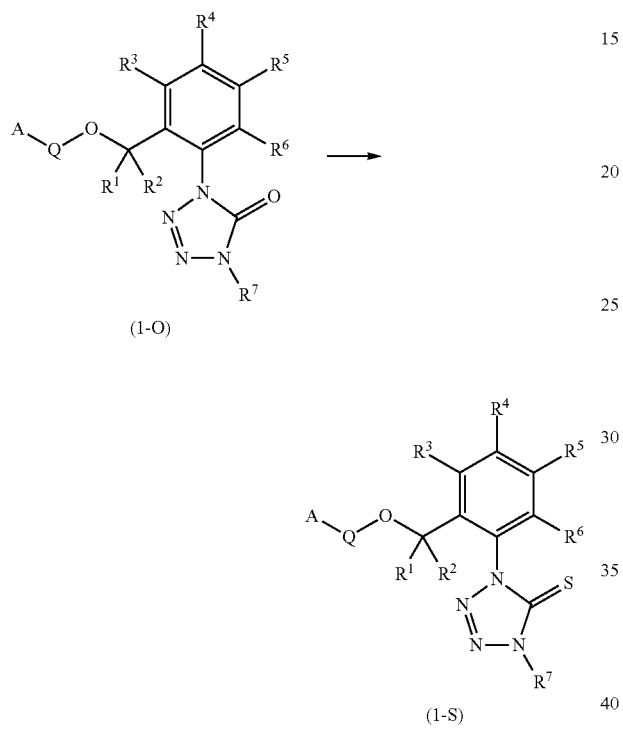

wherein $R^1$, $R^2$, $R^3$, $R^4$, $R^5$, $R^6$, $R^7$, A, and Q are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; nitriles such as acetonitrile; and mixtures thereof.

Examples of the sulfurizing agent to be used in the reaction include phosphorous pentasulfide, and Lawesson's reagent (2,4-Bis(4-methoxyphenyl)-1,3,2,4-dithiadiphosphetane 2,4-disulfide).

In the reaction, the sulfurizing agent is preferably used in the proportion within a range of 0.5 to 1.5 mols based on 1 mol of the compound (1-O).

The reaction temperature of the reaction is usually within a range of −20 to 150° C. The reaction time of the reaction is usually within a range of 0.1 to 24 hours.

In the reaction, if necessary, organic bases such as pyridine and triethylamine; and inorganic bases such as alkali metal hydroxide and alkali metal carbonate may be added, and the amount of the base to be added is within a range of 0.5 to 1.5 mols based on the compound (1-O).

After completion of the reaction, the compound (1-S) can be isolated by performing post-treatment operations such as extraction of the reaction mixture with an organic solvent, and drying and concentration of the organic layer. The isolated present compound can be further purified by chromatography, recrystallization, and the like.

(Production Process G-1)

Among the compounds (1), a compound represented by the following formula (1-4) in which $R^3$ is $R^{71}$ (hereinafter referred to as the compound (1-4)) can be produced by subjecting a compound represented by formula (G1) (hereinafter referred to as the compound (G1)) and a compound represented by formula (G21) (hereinafter referred to as the compound (G21)) to a coupling reaction in the presence of a base and a catalyst:

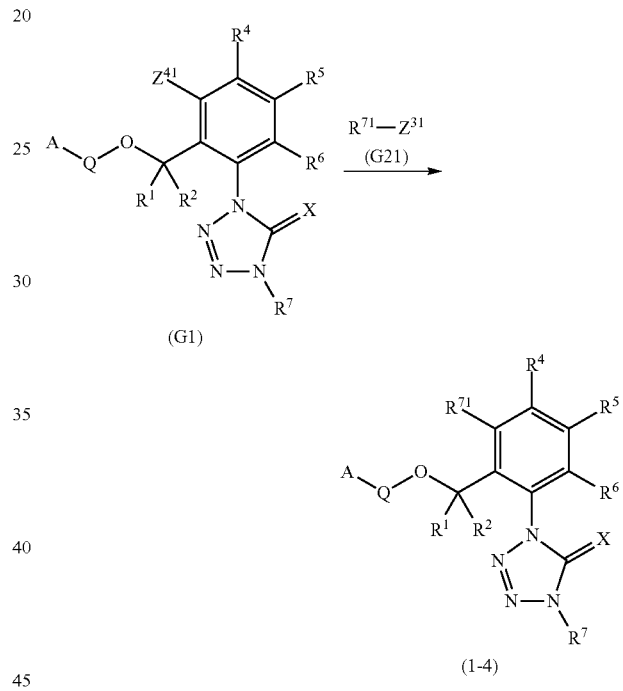

wherein $R^1$, $R^2$, $R^4$, $R^5$, $R^6$, $R^7$, X, A, and Q are the same as defined above, $Z^{31}$ represents $B(OH)_2$, an alkoxyboranyl group, or a trifluoroborate $BF_3^-K^+$, $Z^{41}$ represents a chlorine atom, a bromine atom, an iodine atom, or a trifluoromethanesulfonyloxy group, and $R^{71}$ represents a C1-C6 alkyl group optionally having one or more halogen atoms, a C2-C6 alkenyl group optionally having one or more halogen atoms, a C2-C6 alkynyl group optionally having one or more halogen atoms, or a C3-C6 cycloalkyl group optionally having one or more halogen atoms.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; alcohols such as methanol, ethanol, propanol, and butanol; water; and mixtures thereof.

It is possible to usually use, as the compound (B2) to be used in the reaction, commercially available compounds, or compounds produced by a known method mentioned in N. Miyaura and A. Suzuki, Chem. Rev., 1995, 95, 2457. Specific examples thereof include methylboronic acid, ethylboronic acid, cyclopropylboronic acid, vinylboronic acid, and the like.

Examples of the catalyst to be used in the reaction include palladium(II) acetate/triscyclohexylphosphine, palladium (II) acetate/triphenylphosphine, (diphenylphosphaneferrocenyl)palladium(II)dichloride, bis(triphenylphosphine)palladium(II)dichloride, tris(dibenzylidineacetone) dipalladium/dicyclohexyl(2',4',6'-triisopropylbiphenyl-2-yl) phosphine, and palladium(II) acetate/dicyclohexyl(2',4',6'-triisopropylbiphenyl-2-yl)phosphine.

Examples of the base to be used in the reaction include alkali metal phosphates such as tripotassium phosphate; alkali metal hydroxides such as lithium hydroxide, sodium hydroxide, potassium hydroxide, and cesium hydroxide; alkali metal halides such as sodium fluoride, potassium fluoride, and cesium fluoride; and alkali metal alkoxides such as sodium methoxide, sodium ethoxide, sodium tert-butoxide, and potassium tert-butoxide.

(Production Process G-2)

Among the compounds (1), a compound represented by formula (1-5) in which $R^4$ is $R^{72}$ (hereinafter referred to as the compound (1-5)) can be produced by subjecting a compound represented by formula (G2) (hereinafter referred to as the compound (G2)) and a compound represented by formula (G22) (hereinafter referred to as the compound (G22)) to a coupling reaction in the presence of a base and a catalyst:

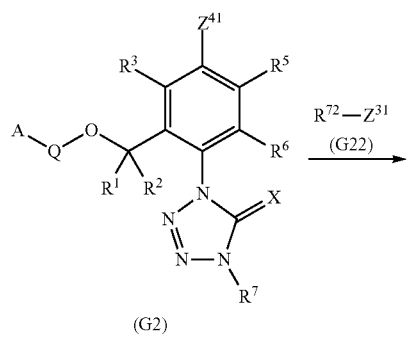

wherein $R^1$, $R^2$, $R^3$, $R^5$, $R^6$, $R^7$, X, A, Q, $Z^{31}$, and $Z^{41}$ are the same as defined above, and $R^{72}$ represents a C1-C3 alkyl group optionally having one or more halogen atoms, or a C1-C3 alkoxy group optionally having one or more halogen atoms.

The reaction can be carried out in accordance with the reaction of Production Process G-1.

Among the compounds (1), a compound represented by formula (1-6) in which $R^5$ is $R^{72}$ (hereinafter referred to as the compound (1-6)) can be produced by subjecting a compound represented by formula (G3) (hereinafter referred to as the compound (G3)) and the compound (G22) to a coupling reaction in the presence of a base and a catalyst:

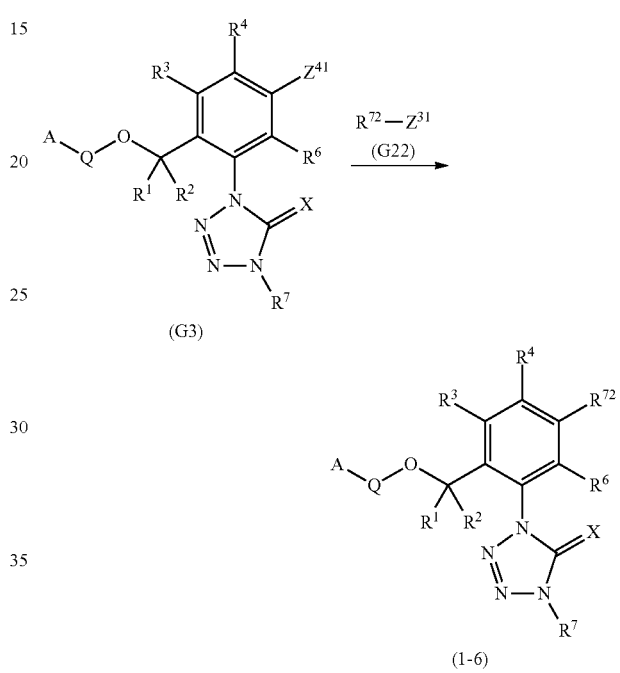

wherein $R^1$, $R^2$, $R^3$, $R^4$, $R^5$, $R^6$, $R^7$, $R^{72}$, X, $Z^{31}$, $Z^{41}$, A, and Q are the same as defined above.

The reaction can be carried out in accordance with the reaction of Production Process G-1.

Among the compounds (1), a compound represented by formula (1-7) in which $R^6$ is $R^{72}$ (hereinafter referred to as the compound (1-7)) can be produced by subjecting a compound represented by formula (G4) (hereinafter referred to as the compound (G4)) and the compound (G22) to a coupling reaction in the presence of a base and a catalyst:

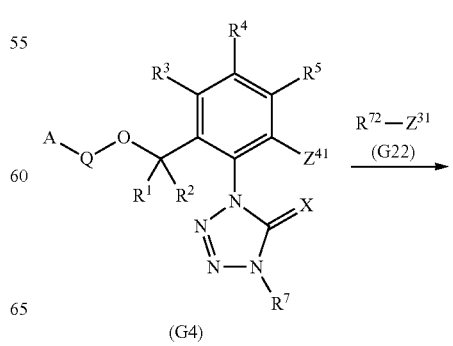

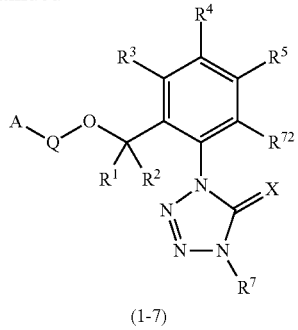

(1-7)

wherein $R^1$, $R^2$, $R^3$, $R^4$, $R^5$, $R^7$, $R^{72}$, X, $Z^{31}$, $Z^{41}$, A, and Q are the same as defined above.

The reaction can be carried out in accordance with the reaction of Production Process G-1.

In accordance with the reaction of Production Process G-1, it is possible to produce a compound in which two or more substituents selected from $R^3$, $R^4$, $R^5$ and $R^6$ are $R^{71}$ or $R^{72}$, among the compounds (1).

It is also possible to produce the compound (1-4), the compound (1-5), the compound (1-6), and the compound (1-7) using other known coupling reactions in place of the coupling reaction of Production Process G.

(Production Process H)

Among the compounds (1), a compound represented by formula (1-8) in which Q is Q1, and $R^8$ is $R^{73}$ (hereinafter referred to as the compound (1-8)) can be produced by subjecting a compound represented by formula (H1) (hereinafter referred to as the compound (H1)) and a compound represented by formula (H21) (hereinafter referred to as the compound (H21)) to a coupling reaction in the presence of a base and a catalyst:

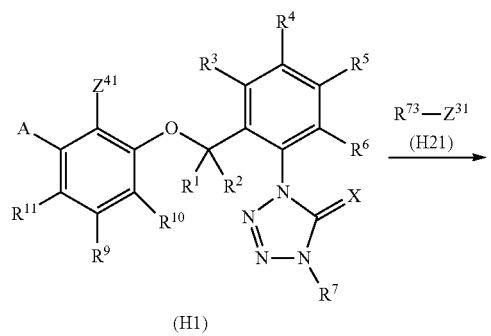

(H1)

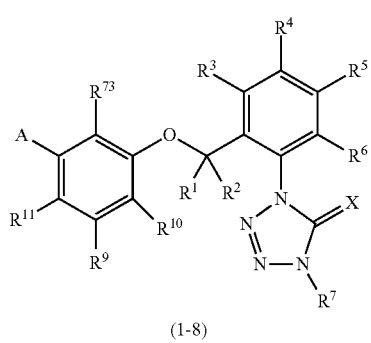

(1-8)

wherein $R^1$, $R^2$, $R^3$, $R^4$, $R^5$, $R^6$, $R^7$, $R^9$, $R^{10}$, X, A, $Z^{31}$, and $Z^{41}$ are the same as defined above, and $R^{73}$ represents a C1-C6 alkyl group optionally having one or more halogen atoms, a C3-C6 cycloalkyl group optionally having one or more halogen atoms, a C2-C6 alkenyl group optionally having one or more halogen atoms, or a C2-C6 alkynyl group optionally having one or more halogen atoms.

The reaction can be carried out in accordance with the reaction of Production Process G-1.

Among the compounds (1), a compound represented by formula (1-9) in which Q is Q1, and $R^9$ is $R^{73}$ (hereinafter referred to as the compound (1-9)) can be produced by subjecting a compound represented by formula (H2) (hereinafter referred to as the compound (H2)) and the compound (H21) to coupling reaction in the presence of a base and a catalyst:

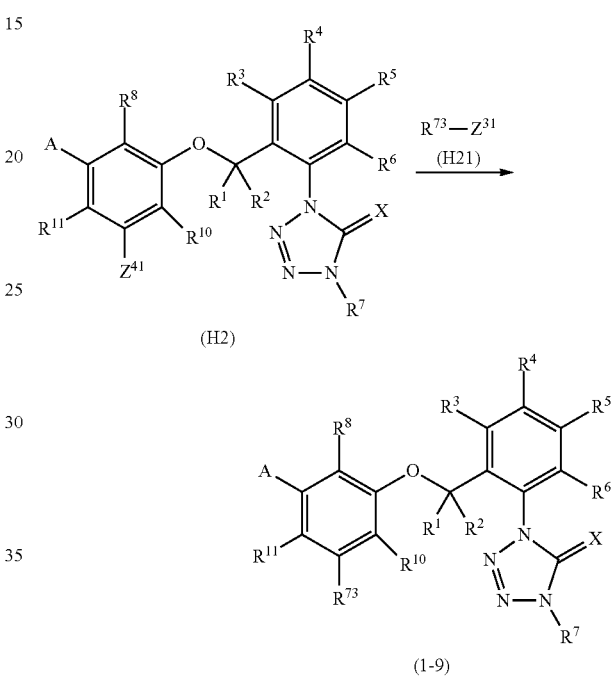

(H2)

(1-9)

wherein $R^1$, $R^2$, $R^3$, $R^4$, $R^5$, $R^6$, $R^7$, $R^8$, $R^{10}$, $R^{11}$, $R^{73}$, X, $Z^{31}$, $Z^{41}$, and A are the same as defined above.

The reaction can be carried out in accordance with the reaction of Production Process G-1.

Among the compounds (1), a compound represented by formula (1-10) in which Q is Q1 and $R^{19}$ is $R^{73}$ (hereinafter referred to as the compound (1-10)) can be produced by subjecting a compound represented by formula (H3) (hereinafter referred to as the compound (H3)) and the compound (H21) to a coupling reaction in the presence of a base and a catalyst:

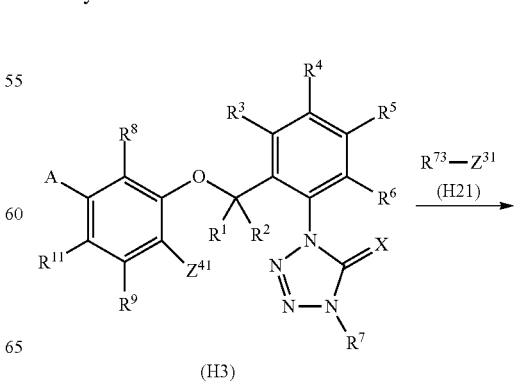

(H3)

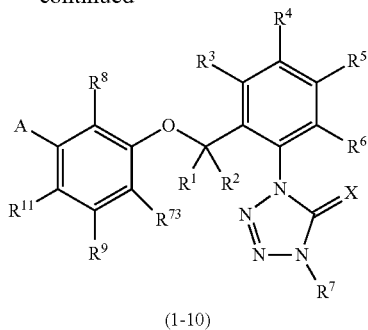

(1-10)

wherein $R^1, R^2, R^3, R^4, R^5, R^6, R^7, R^8, R^9, R^{11}, R^{73}, X, Z^{41}, Z^{31}$, and A are the same as defined above.

The reaction can be carried out in accordance with the reaction of Production Process G-1.

Among the compounds (1), a compound represented by formula (1-11) in which Q is Q1, and $R^{11}$ is $R^{73}$ (hereinafter referred to as the compound (1-11)) can be produced by subjecting a compound represented by formula (H4) (hereinafter referred to as the compound (H4)) and the compound (H21) to a coupling reaction in the presence of a base and a catalyst:

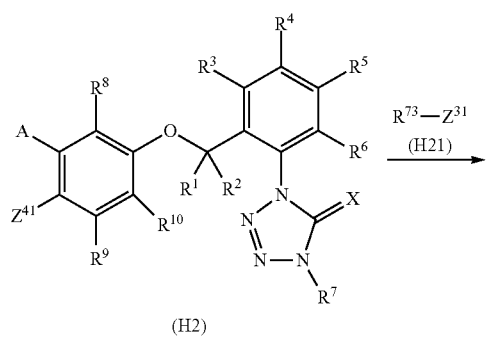

(H2)

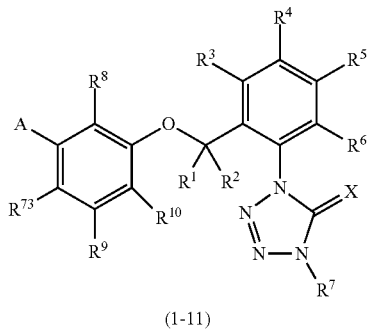

(1-11)

wherein $R^1, R^2, R^3, R^4, R^5, R^6, R^7, R^8, R^9, R^{10}, R^{73}, X, Z^{41}, Z^{31}$, and A are the same as defined above.

The reaction can be carried out in accordance with the reaction of Production Process G-1.

In accordance with the reaction in Production Process G-1, it is possible to produce a compound in which two or more substituents selected from $R^8, R^9, R^{10}$, and $R^{11}$ are $R^{73}$, among the compounds (1).

It is also possible to produce the compound (1-8), the compound (1-9), the compound (1-10), and the compound (1-11) using other known coupling reactions in place of the coupling reaction of Production Process G-1.

(Production Process I)

Among the compounds (1), a compound represented by formula (1-12) in which Q is Q2, and $R^{11}$ is $R^{73}$ (hereinafter referred to as the compound (1-12)) can be produced by subjecting a compound represented by formula (I1) (hereinafter referred to as the compound (I1)) and the compound (H21) to a coupling reaction in the presence of a base and a catalyst:

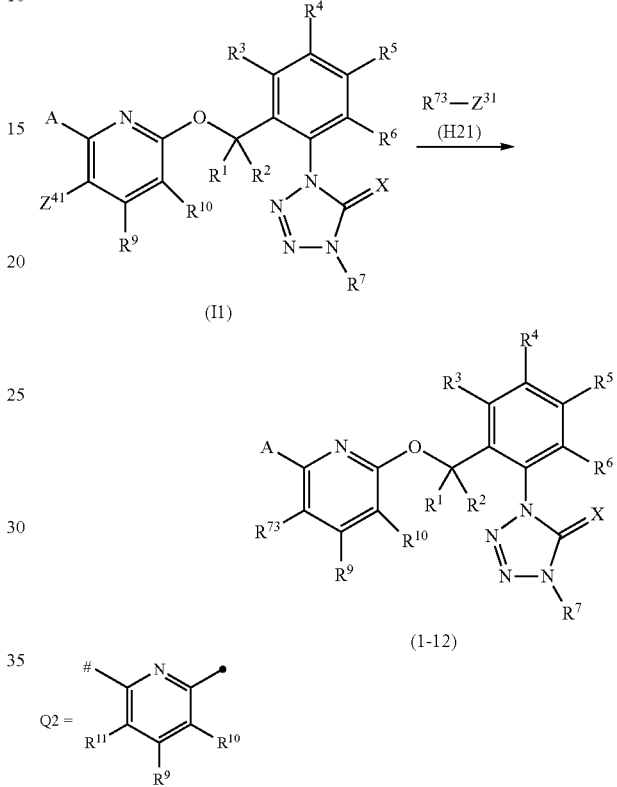

wherein $R^1, R^2, R^3, R^4, R^5, R^6, R^7, R^9, R^{10}, R^{73}, X, Z^{31}, Z^{41}$, and A are the same as defined above.

The reaction can be carried out in accordance with the reaction of Production Process G-1.

Among the compounds (1), a compound represented by formula (1-13) in which Q is Q2 and $R^9$ is $R^{73}$ (hereinafter referred to as the compound (1-13)) can be produced by subjecting a compound represented by formula (I2) (hereinafter referred to as the compound (I2)) and the compound (H21) to a coupling reaction in the presence of a base and a catalyst:

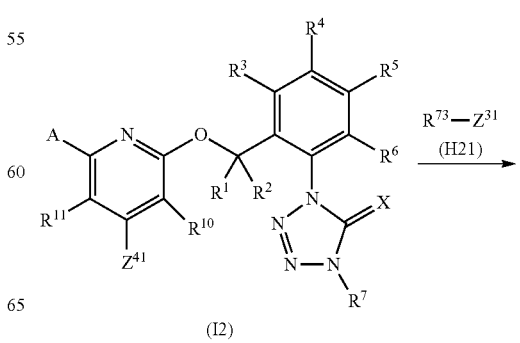

-continued

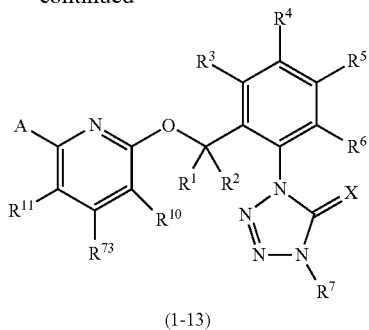

(1-13)

wherein $R^1$, $R^2$, $R^3$, $R^4$, $R^5$, $R^6$, $R^7$, $R^{10}$, $R^{11}$, $R^{73}$, X, $Z^{31}$, $Z^{41}$, and A are the same as defined above.

The reaction can be carried out in accordance with the reaction of Production Process G-1.

Among the compounds (1), a compound represented by formula (1-14) in which Q is Q2 and $R^{10}$ is $R^{73}$ (hereinafter referred to as the compound (1-14)) can be produced by subjecting a compound represented by formula (I3) (hereinafter referred to as the compound (I3)) and the compound (H21) to a coupling reaction in the presence of a base and a catalyst:

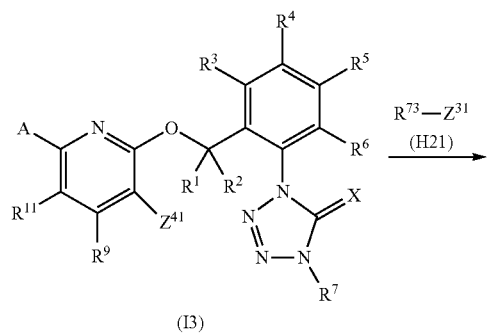

(I3)

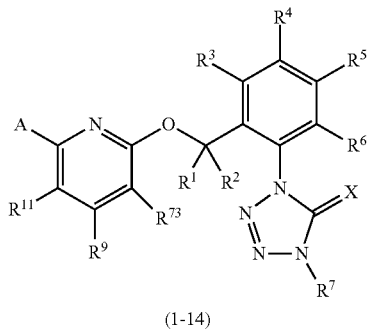

(1-14)

wherein $R^1$, $R^2$, $R^3$, $R^4$, $R^5$, $R^6$, $R^7$, $R^9$, $R^{11}$, $R^{73}$, X, $Z^{31}$, $Z^{41}$, and the symbol A are the same as defined above.

The reaction can be carried out in accordance with the reaction of Production Process G-1.

In accordance with the reaction of Production Process G-1, it is possible to produce a compound in which two or more substituents selected from $R^9$, $R^{10}$, and $R^{11}$ are $R^{73}$, among the compounds (1).

It is also possible to produce the compound (1-12), the compound (1-13), and the compound (1-14) using other known coupling reactions in place of the coupling reaction of Production Process G-1.

(Production Process J)

A compound represented by formula (1-15) (hereinafter referred to as the compound (1-15)) can be produced by reacting a compound represented by formula (J1) (hereinafter referred to as the compound (J1)) with $R^{15}O-NH_2$ or a salt thereof (hereinafter referred to as the compound (J2)):

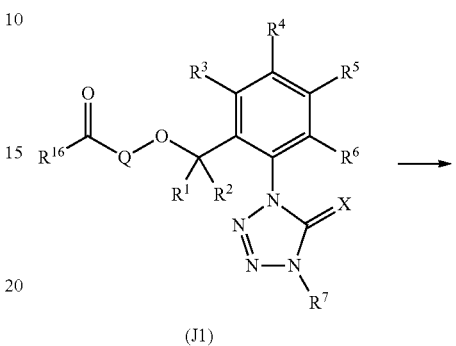

(J1)

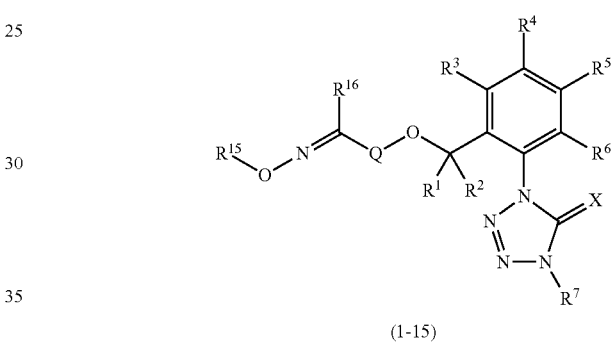

(1-15)

wherein $R^1$, $R^2$, $R^3$, $R^4$, $R^5$, $R^6$, $R^7$, $R^{15}$, $R^{16}$, and Q are the same as defined above.

Examples of the solvent to be used in the reaction include alcohols such as methanol, ethanol, propanol, and butanol; water; hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; sulfoxides such as dimethyl sulfoxide; nitriles such as acetonitrile; and mixtures thereof. Examples of the salt of the compound (J2) usable in the reaction include a hydrochloride, a sulfate, and a carbonate.

In the reaction, the compound (J2) is usually used in the proportion within a range of 1 to 10 mols based on 1 mol of the compound (J1).

In the reaction, if necessary, additives may be added, and examples thereof include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal acetates such as sodium acetate and potassium acetate; and quaternary ammonium salts such as tetrabutylammonium hydroxide. These additives are usually used in the proportion within a range of 0.5 to 10 mols based on 1 mol of the compound (J1).

The reaction temperature of the reaction is usually within a range of 20 to 150° C. The reaction time of the reaction is usually within a range of 0.1 to 72 hours.

After completion of the reaction, the compound (1-15) can be isolated by performing post-treatment operations such as extraction of the reaction mixture with an organic solvent, and drying and concentration of the organic layer. The isolated compound may be further purified by operations such as distillation, chromatography, and recrystallization.

The process for synthesizing an intermediate compound for production will be mentioned in detail below.

(Reference Production Process A)

A compound represented by formula (XA3) (hereinafter referred to as the compound (XA3)) can be produced by reacting a compound represented by formula (XA1) (hereinafter referred to as the compound (XA1)) or a compound represented by formula (XA2) (hereinafter referred to as the compound (XA2)) with an azidation agent:

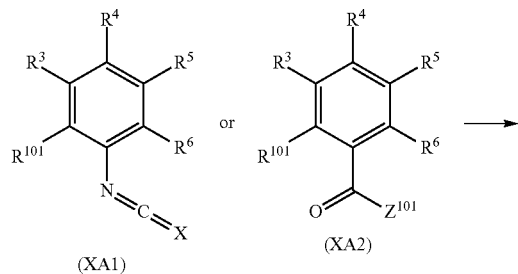

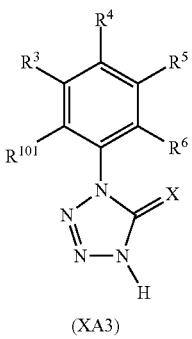

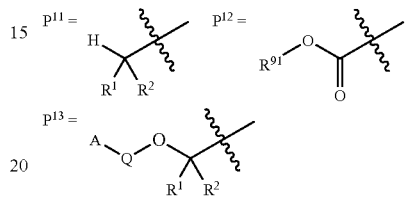

wherein $R^1$, $R^2$, $R^3$, $R^4$, $R^5$, $R^6$, X, A, and Q are the same as defined above, $R^{101}$ represents $P^{11}$, $P^{12}$, or $P^{13}$, $R^{91}$ represents a C1-C12 alkyl group, $Z^{101}$ represents a chlorine atom or a bromine atom, and the wavy line represents a binding site.

The reaction can be carried out in accordance with the reaction of Production Process D.

(Reference Production Process B)

The compound (XA1) can be produced by reacting a compound represented by formula (XB1) (hereinafter referred to as the compound (XB1)) with an isocyanating agent:

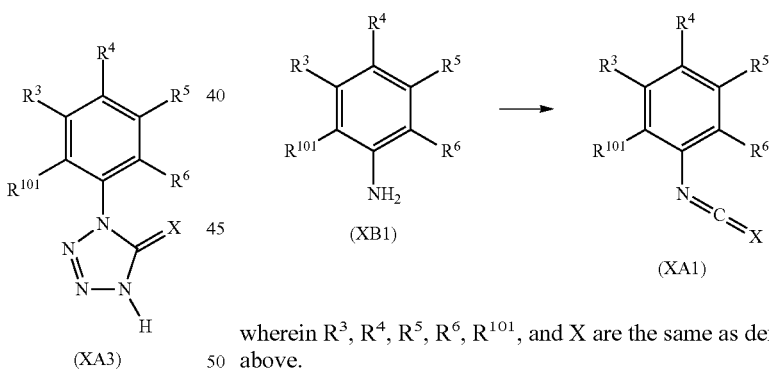

wherein $R^3$, $R^4$, $R^5$, $R^6$, $R^{101}$, and X are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

It is possible to use, as the isocyanating agent to be used in the reaction, for example, phosgene, diphosgene, triphosgene, thiophosgene, N,N-carbodiimidazole, and N,N-thiocarbodiimidazole.

In the reaction, the isocyanating agent is usually used in the proportion within a range of 0.34 to 10 mols based on 1 mol of the compound (XB1).

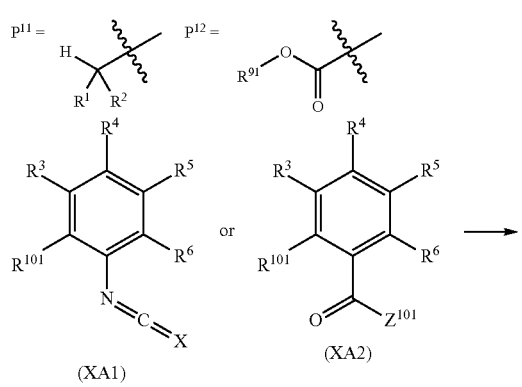

The reaction temperature of the reaction is usually within a range of −20 to 150° C. The reaction time of the reaction is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate may be added, and these compounds are usually used in the proportion within a range of 0.05 to 5 mols based on 1 mol of the compound (XB1).

After completion of the reaction, the compound (XA1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process C)

The compound (XA2) can be produced by reacting compound represented by formula (XC1) (hereinafter referred to as the compound (XC1)) with a halogenating agent:

is usually in the proportion within a range of 0.001 to 1 mols based on 1 mol of the compound (XC1).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually used in the proportion within a range of 0.05 to 5 mols based on 1 mol of the compound (XC1).

After completion of the reaction, the compound (XA2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process D)

The compound (XA1) can be produced by reacting the compound (XB1) with a carbamating agent to obtain a compound represented by formula (XD1) (hereinafter referred to as the compound (XD1)), and then reacting the compound (XD1) with an isocyanating agent:

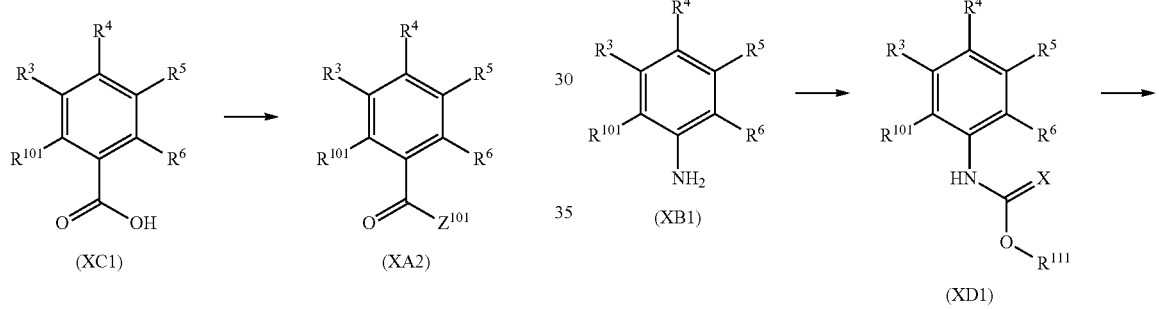

wherein $R^3$, $R^4$, $R^5$, $R^6$, $R^{101}$, and $Z^{101}$ are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the halogenating agent to be used in the reaction include phosphorus oxychloride, phosphorus trichloride, phosphorus pentachloride, thionyl chloride, phosphorus oxybromide, phosphorus tribromide, phosphorus pentabromide, phosphorus triiodide, oxalyl dichloride, oxalyl dibromide, triphosgene, diphosgene, phosgene, and sulfuryl chloride.

In the reaction, the halogenating agent is usually used in the proportion within a range of 1 to 10 mols based on 1 mol of the compound (XC1).

The reaction temperature of the reaction is usually within a range of −20 to 150° C. The reaction time of the reaction is usually within a range of 0.1 to 24 hours.

In the reaction, the catalyst may be added, and dimethylformamide is used. The amount of the catalyst to be used wherein $R^3$, $R^4$, $R^5$, $R^6$, $R^{101}$, and X are the same as defined above, and $R^{111}$ represents a C1-C12 alkyl group or a phenyl group.

The process for producing the compound (XD1) from the compound (XB1) will be described below.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the carbamating agent to be used in the reaction include phenyl chlorocarbonate, methyl chlorocarbonate, ethyl chlorocarbonate, n-propyl chlorocarbonate, isopropyl chlorocarbonate, n-butyl chlorocarbonate, tert-butyl chlorocarbonate, di-tert-butyl dicarbonate, dimethyl dicarbonate, diethyl dicarbonate, 0-phenyl chlorothioformate, O-methyl chlorothioformate, O-ethyl chlorothioformate, and the like.

In the reaction, the carbamating agent is usually used in the proportion within a range of 1 to 10 mols based on 1 mol of the compound (XB1).

The reaction temperature of the reaction is usually within a range of −20 to 150° C. The reaction time of the reaction is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually used in the proportion within a range of 0.05 to 5 mols based on 1 mol of the compound (XB1).

After completion of the reaction, the compound (XD1) can be isolated by performing post-treatment operations such as extraction of the reaction mixture with an organic solvent, and drying and concentration of the organic layer. The isolated compound may be further purified by operations such as distillation, chromatography, and recrystallization.

The process for producing the compound (XA1) from the compound (XD1) will be described below.

The reaction is usually performed in a solvent.

Examples of the solvent to be used in the reaction include ethers such as tetrahydrofuran, 1,4-dioxane, ethylene glycol dimethyl ether, and methyl tert-butyl ether; aromatic hydrocarbons such as toluene and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

It is possible to use, as the isocyanating agent to be used in the reaction, for example, phosphorus pentachloride, phosphorus oxychloride, diphosphorus pentaoxide, trichlorosilane, dichlorosilane, monochlorosilane, boron trichloride, 2-chloro-1,3,2-benzodioxaborole, diiodosilane, methyltrichlorosilane, dimethyldichlorosilane, and chlorotrimethylsilane.

In the reaction, the isocyanating agent is usually used in the proportion within a range of 1 to 10 mols based on 1 mol of the compound (XD1).

The reaction temperature of the reaction is usually within a range of −20 to 250° C. The reaction time of the reaction is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually used in the proportion within a range of 0.05 to 5 mols based on 1 mol of the compound (XD1).

After completion of the reaction, the compound (XA1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process E)

A compound represented by formula (XE2) (hereinafter referred to as the compound (XE2)) can be produced by reacting a compound represented by formula (XE1) (hereinafter referred to as the compound (XE1)) with hydrogen in the presence of a catalyst:

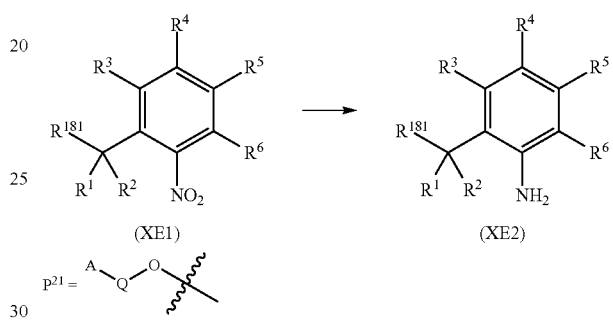

wherein $R^1$, $R^2$, $R^3$, $R^4$, $R^5$, $R^6$, A, and Q are the same as defined above, $R^{181}$ represents a hydrogen atom or $P^{21}$, and the wavy line represents a binding site.

The reaction is usually performed in a solvent.

Examples of the solvent to be used in the reaction include alcohols such as methanol, ethanol, propanol, and butanol; esters such as ethyl acetate and butyl acetate; halogenated hydrocarbons such as chloroform, 1,2-dichloroethane, and chlorobenzene; ethers such as tetrahydrofuran, 1,4-dioxane, ethylene glycol dimethyl ether, methyl tert-butyl ether, and diisopropyl ether; hydrocarbons such as n-hexane, cyclohexane, toluene, and xylene; water; and mixtures thereof.

Examples of the catalyst to be used in the reaction include palladium-supported carbon (Pd/C), platinum-supported carbon (Pt/C), osmium-supported carbon (Os/C), ruthenium-supported carbon (Ru/C), rhodium-supported carbon (Rh/C), Raney (registered trademark) nickel, and the like.

In the reaction, the catalyst is usually used in the proportion within a range of 0.0001 to 1 mols based on 1 mol of the compound (XE1).

The reaction temperature of the reaction is usually within a range of −20 to 150° C. The reaction time of the reaction is usually within a range of 0.1 to 24 hours.

After completion of the reaction, the compound (XE2) can be isolated by performing post-treatment operations such as concentration of the organic layer after filtration of the catalyst. The isolated compound may be further purified by operations such as distillation, chromatography, and recrystallization.

(Reference Production Process F)

The compound (XE2) can be produced by reacting the compound (XE1) with a reducing agent in the presence of an acid:

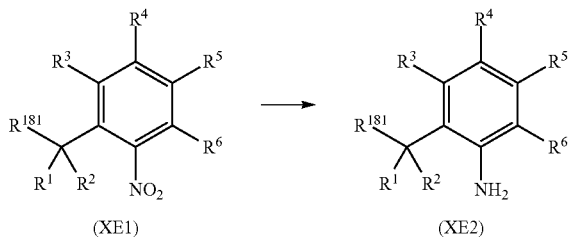

(XE1) → (XE2)

wherein $R^1$, $R^2$, $R^3$, $R^4$, $R^5$, $R^6$, and $R^{181}$ are the same as defined above.

The reaction is usually performed in a solvent.

Examples of the solvent to be used in the reaction include aliphatic carboxylic acids such as acetic acid; alcohols such as methanol and ethanol; water; and mixtures thereof.

Examples of the reducing agent to be used in the reaction include iron, tin, and zinc.

Examples of the acid to be used in the reaction include hydrochloric acid, sulfuric acid, acetic acid, and an aqueous ammonium chloride solution.

In the reaction, the reducing agent is usually used in the proportion within a range of 1 to 30 mols based on 1 mol of the compound (XE1).

In the reaction, the acid is usually used in the proportion within a range of 1 to 30 mols based on 1 mol of the compound (XE1).

The reaction temperature of the reaction is usually within a range of −20 to 150° C. The reaction time of the reaction is usually within a range of 0.1 to 24 hours.

After completion of the reaction, the compound (XE2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process G)

A compound represented by formula (XG2) (hereinafter referred to as the compound (XG2)) can be produced by reacting a compound represented by formula (XG1) (hereinafter referred to as the compound (XG1)) with a compound (E1) in the presence of a base:

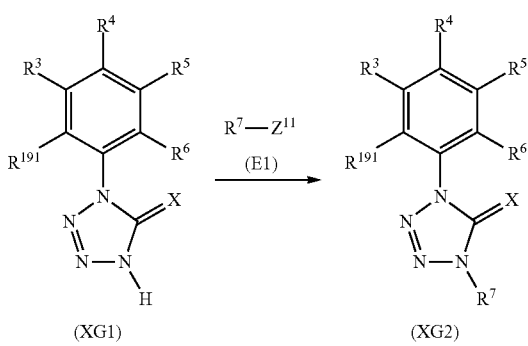

(XG1) → (XG2)

wherein $R^3$, $R^4$, $R^5$, $R^6$, $R^7$, X and $Z^{11}$ are the same as defined above, and $R^{191}$ represents $P^{11}$ or $P^{12}$.

The reaction can be carried out in accordance with the reaction of Production Process E.

(Reference Production Process H)

A compound represented by formula (XH2) (hereinafter referred to as the compound (XH2)) can be produced by reacting a compound represented by formula (XH1) (hereinafter referred to as the compound (XH1)) with a halogenating agent:

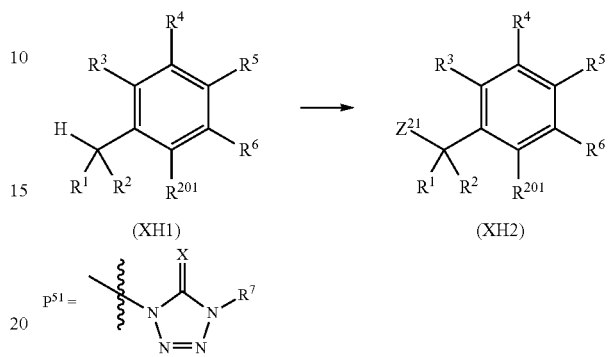

(XH1) → (XH2)

$$P^{51} = \text{(structure)}$$

wherein $R^1$, $R^2$, $R^3$, $R^4$, $R^5$, $R^6$, $R^7$, $Z^{21}$, and X are the same as defined above, and $R^{201}$ represents $P^{51}$ or a nitro group.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the halogenating agent usable in the reaction include a chlorinating agent, a brominating agent, or an iodinating agent, for example, chlorine, bromine, iodine, sulfuryl chloride, N-chlorosuccinimide, N-bromosuccinimide, 1,3-dibromo-5,5-dimethylhydantoin, iodosuccinimide, tert-butyl hypochlorite, N-chloroglutarimide, N-bromoglutarimide, N-chloro-N-cyclohexyl-benzenesulfonimide, and N-bromophthalimide.

In the reaction, a radical initiator can also be used.

Examples of the radical initiator to be used in the reaction include benzoyl peroxide, azobisisobutyronitrile (AIBN), diacyl peroxide, dialkyl peroxydicarbonate, tert-alkylperoxyester, monoperoxycarbonate, di(tert-alkylperoxy)ketal, and ketone peroxide.

In the reaction, the halogenating agent is usually used in the proportion within a range of 1 to 10 mols, and the radical initiator is usually used in the proportion within a range of 0.01 to 5 mols, based on 1 mol of the compound (XH1).

The reaction temperature of the reaction is usually within a range of −20 to 150° C. The reaction time of the reaction is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process I)

A compound represented by formula (XJ2) (hereinafter referred to as the compound (XJ2)) can be produced by reacting the compound (XH2) with a compound represented by formula (XJ1) (hereinafter referred to as the compound (XJ1)):

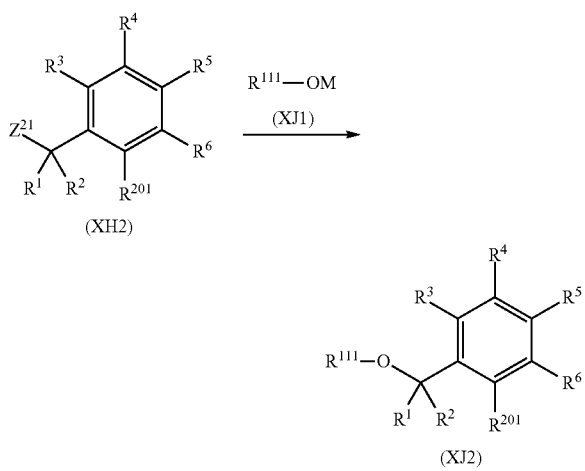

wherein $R^1$, $R^2$, $R^3$, $R^4$, $R^{201}$, $R^{111}$, and $Z^{21}$ are the same as defined above, and M represents sodium, potassium, or lithium.

The reaction is usually performed in a solvent.

Examples of the solvent to be used in the reaction include ethers such as tetrahydrofuran, 1,4-dioxane, ethylene glycol dimethyl ether, methyl tert-butyl ether, and diisopropyl ether; hydrocarbons such as n-hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the compound (XJ1) usable in the reaction include sodium methoxide, sodium ethoxide, sodium tert-butoxide, potassium tert-butoxide, and the like.

In the reaction, the compound (XJ1) is usually used in the proportion within a range of 1 to 10 mols based on 1 mol of the compound (XH2).

The reaction temperature of the reaction is usually within a range of −20 to 150° C. The reaction time of the reaction is usually within a range of 0.1 to 24 hours.

After completion of the reaction, the compound (XJ2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process J)

A compound represented by formula (XK1) (hereinafter referred to as the compound (XK1)) can be produced by reacting the compound (XH2) with water in the presence of a base:

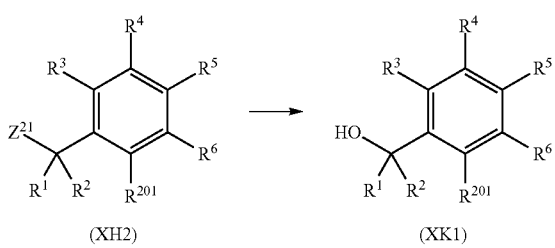

wherein $R^1$, $R^2$, $R^3$, $R^4$, $R^5$, $R^6$, $R^{201}$, and $Z^{21}$ are the same as defined above.

The reaction is usually performed in water, or a solvent containing water.

Examples of the solvent to be used in the reaction include ethers such as diethyl ether, tetrahydrofuran, 1,4-dioxane, ethylene glycol dimethyl ether, anisole, methyl tert-butyl ether, and diisopropyl ether; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the base to be used in the reaction include organic bases such as triethylamine, pyridine, N-methylmorpholine, 4-dimethylaminopyridine, diisopropylethylamine, and diazabicycloundecene; metal organic acid salts such as lithium formate, lithium acetate, sodium formate, sodium acetate, potassium formate, and potassium acetate; metal nitrates such as silver nitrate and sodium nitrate; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; and alkali metal alkoxides such as sodium methoxide, sodium ethoxide, sodium tert-butoxide, and potassium tert-butoxide.

In the reaction, the base is usually in the proportion within a range of 1 to 100 mols, and water is usually in the proportion within a range of 1 mol to large excess, based on 1 mol of the compound (XH2).

The reaction temperature of the reaction is usually within a range of −20 to 150° C. The reaction time of the reaction is usually within a range of 0.1 to 24 hours.

After completion of the reaction, the compound (XK1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process K)

The compound (XH2) can be produced by reacting the compound (XJ2) with a halogenating agent:

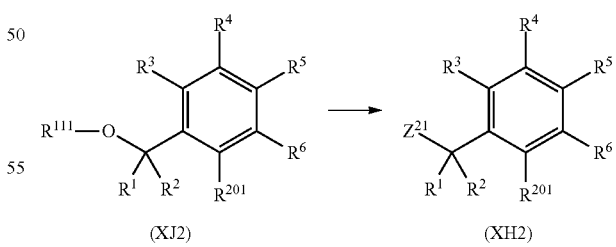

wherein $R^1$, $R^2$, $R^3$, $R^4$, $R^5$, $R^6$, $R^{201}$, $R^{111}$, and $Z^{21}$ are the same as defined above.

The reaction is usually performed in a solvent.

Examples of the solvent to be used in the reaction include hydrocarbons such as n-hexane, cyclohexane, toluene, and xylene; halogenated hydrocarbons such as chloroform, 1,2-dichloroethane, and chlorobenzene; ketones such as acetone, methyl ethyl ketone, and methyl isobutyl ketone; nitriles such as acetonitrile; organic acids such as formic acid, acetic acid, and trifluoroacetic acid; water; and mixtures thereof.

Examples of the halogenating agent to be used in the reaction include hydrochloric acid, hydrogen bromide, hydrobromic acid, and hydroiodic acid.

In the reaction, the halogenating agent is usually used in the proportion of 1 mol or more based on 1 mol of the compound (XJ2).

The reaction temperature of the reaction is usually within a range of −20 to 150° C. The reaction time of the reaction is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process L)

The compound (XH2) can be produced by reacting the compound (XK1) with a halogenating agent:

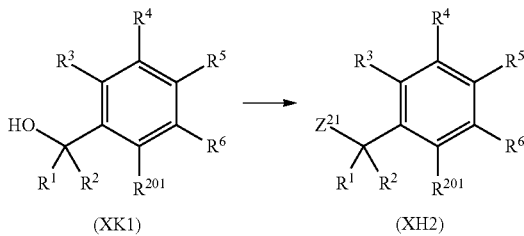

wherein $R^1$, $R^2$, $R^3$, $R^4$, $R^5$, $R^6$, $R^{201}$, and $Z^{21}$ are the same as defined above.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; organic acids such as formic acid, acetic acid, and trifluoroacetic acid; water; and mixtures thereof.

Examples of the halogenating agent to be used in the reaction include bromine, chlorine, sulfuryl chloride, hydrochloric acid, hydrobromic acid, hydroiodic acid, boron tribromide, phosphorus tribromide, trimethylsilyl chloride, trimethylsilyl bromide, trimethylsilyl iodide, thionyl chloride, thionyl bromide, phosphorus oxychloride, phosphorus trichloride, phosphorus pentachloride, thionyl chloride, phosphorus oxybromide, phosphorus pentabromide, phosphorus triiodide, oxalyl dichloride, oxalyl dibromide, combination of acetyl chloride and zinc chloride, combination of N-bromosuccinimide and dimethyl sulfide, combination of lithium chloride, triethylamine, and methanesulfonyl chloride, combination of sodium iodide and a boron trifluoride diethyl ether complex, aluminum chloride or trimethylsilyl chloride, combination of acetyl bromide and a boron trifluoride diethyl ether complex, and the like.

In the reaction, the halogenating agent is usually used in the proportion within a range of 1 to 10 mols based on 1 mol of the compound (XK1).

Zinc chloride, dimethyl sulfide, a boron trifluoride diethyl ether complex, a boron trifluoride diethyl ether complex, lithium chloride, aluminum chloride, and trimethylsilyl chloride are used as additives for acceleration of the reaction, and the amount of any additive to be used is usually in the proportion within a range of 0.01 to 5 mols based on 1 mol of the compound (XK1).

The reaction temperature of the reaction is usually within a range of −20 to 150° C. The reaction time of the reaction is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process M)

A compound represented by formula (XM3) (hereinafter referred to as the compound (XM3)) can be produced by reacting the compound (XK1) with a compound represented by formula (XM2) (hereinafter referred to as the compound (XM2)) in the presence of a base:

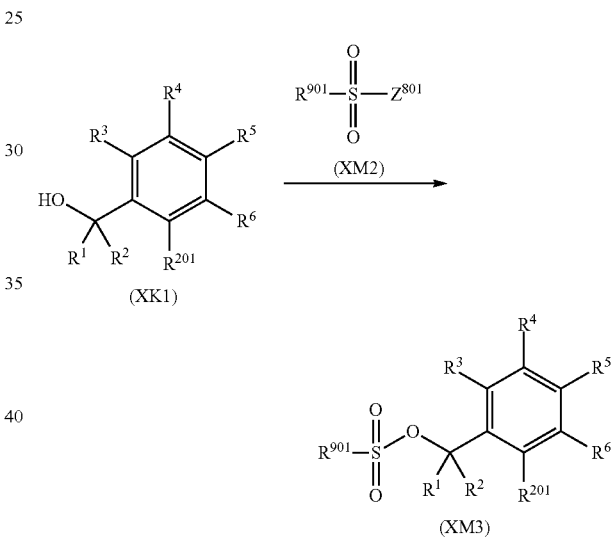

wherein $R^1$, $R^2$, $R^3$, $R^4$, $R^5$, $R^6$, and $R^{201}$ are the same as defined above, $R^{901}$ represents a C1-C6 alkyl group, a C1-C6 haloalkyl group, a C6-C16 aryl group, or a C6-C16 haloaryl group, and $Z^{801}$ represents a fluorine atom, a chlorine atom, a bromine atom, or an iodine atom.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium methoxide, sodium ethoxide, sodium tert-butoxide, and potassium tert-butoxide.

In the reaction, the compound (XM2) is usually used in the proportion within a range of 1 to 10 mols, and the base is usually in the proportion within a range of 1 to 5 mols, based on 1 mol of the compound (XK1).

The reaction temperature of the reaction is usually within a range of −20 to 150° C. The reaction time of the reaction is usually within a range of 0.1 to 24 hours.

In the reaction, if necessary, sodium iodide, tetrabutylammonium iodide, and the like may be added, and these compounds are usually used in the proportion within a range of 0.001 to 1.2 mols based on 1 mol of the compound (XK1).

After completion of the reaction, the compound (XM3) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process N)

A compound represented by formula (XN12) (hereinafter referred to as the compound (XN12)) can be produced by subjecting a compound represented by formula (XN11) (hereinafter referred to as the compound (XN11)) and the compound (G21) to a coupling reaction in the presence of a base and a catalyst:

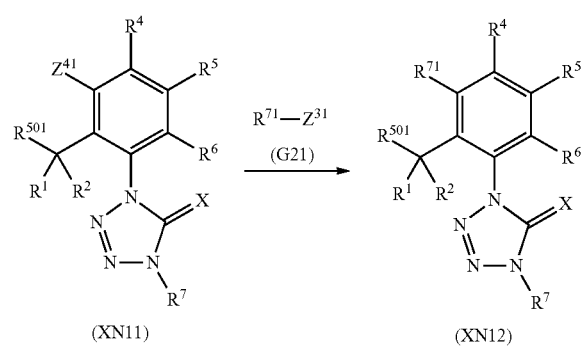

(XN11)          (XN12)

wherein $R^{501}$ represents a hydrogen atom or an $OR^{111}$ group, and $R^{111}$, $R^1$, $R^2$, $R^4$, $R^5$, $R^6$, $R^7$, $R^{71}$, X, $Z^{31}$, and $Z^{41}$ are the same as defined above.

The reaction can be carried out in accordance with the reaction of Production Process G-1.

A compound represented by formula (XN22) (hereinafter referred to as the compound (XN22)) can be produced by subjecting a compound represented by formula (XN21) (hereinafter referred to as the compound (XN21)) and the compound (G22) to a coupling reaction in the presence of a base and a catalyst:

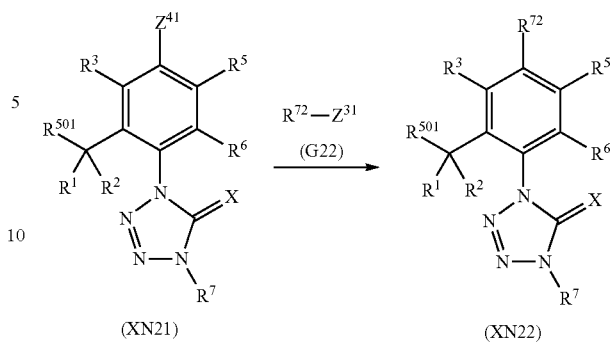

(XN21)          (XN22)

wherein $R^1$, $R^2$, $R^3$, $R^5$, $R^6$, $R^7$, $R^{72}$, $R^{501}$, $Z^{31}$, $Z^{41}$, and X are the same as defined above.

The reaction can be carried out in accordance with the reaction of Production Process G-1.

A compound represented by formula (XN32) (hereinafter referred to as the compound (XN32)) can be produced by subjecting a compound represented by formula (XN31) (hereinafter referred to as the compound (XN31)) and the compound (G22) to a coupling reaction in the presence of a base and a catalyst:

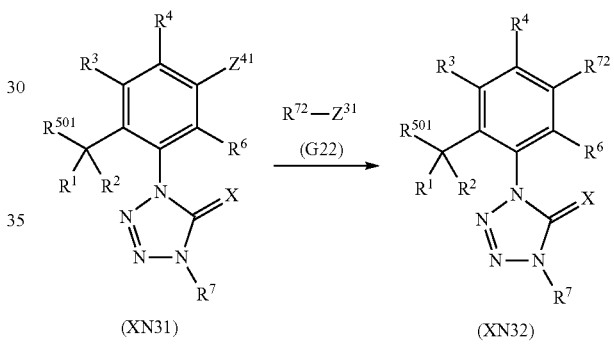

(XN31)          (XN32)

wherein $R^1$, $R^2$, $R^3$, $R^4$, $R^6$, $R^7$, $R^{72}$, $R^{501}$, $Z^{31}$, $Z^{41}$, and X are the same as defined above.

The reaction can be carried out in accordance with the reaction of Production Process G-1.

A compound represented by formula (XN42) (hereinafter referred to as the compound (XN42)) can be produced by subjecting a compound represented by formula (XN41) (hereinafter referred to as the compound (XN41)) and the compound (G22) to a coupling reaction in the presence of a base and a catalyst:

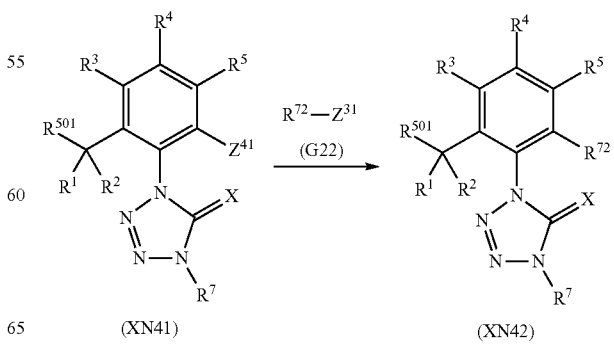

(XN41)          (XN42)

wherein $R^1$, $R^2$, $R^3$, $R^4$, $R^5$, $R^7$, $R^{72}$, $R^{501}$, $Z^{31}$, $Z^{41}$, and X are the same as defined above.

The reaction can be carried out in accordance with the reaction of Production Process G-1.

In accordance with the reaction of Production Process G-1, it is possible to produce a compound in which two or more substituents selected from $R^3$, $R^4$, $R^5$, and $R^6$ are $R^{71}$ and/or $R^{72}$, among the compounds represented by formula (XN50):

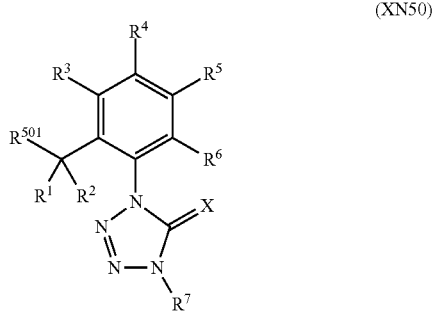

wherein $R^1$, $R^2$, $R^3$, $R^4$, $R^5$, $R^6$, $R^7$, $R^{501}$, and X are the same as defined above.

It is also possible to use other known coupling reactions in place of the coupling reaction mentioned in Production Process G.

(Reference Production Process O)

A compound represented by formula (XW2) (hereinafter referred to as the compound (XW2)) can be produced by reacting a compound represented by formula (XW1) (hereinafter referred to as the compound (XW1)) with a compound represented by formula (XW3) (hereinafter referred to as the compound (XW3)) in the presence of a reaction accelerator:

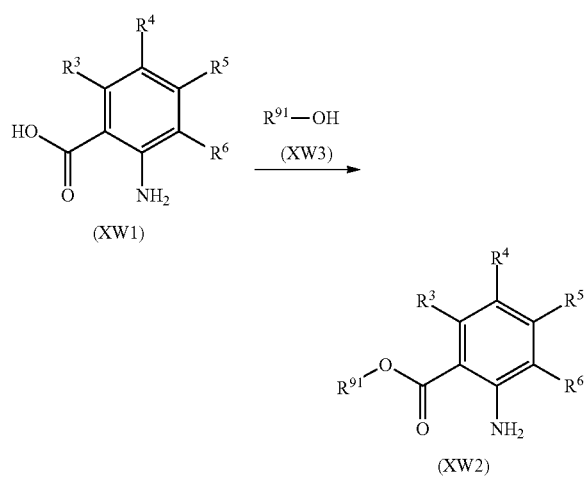

wherein $R^3$, $R^4$, $R^5$, $R^6$, and $R^{91}$ are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof, and the compound (XW3) may be used as the solvent.

Examples of the compound (XW3) usable in the reaction include methyl alcohol, ethyl alcohol, propyl alcohol, isopropyl alcohol, n-butyl alcohol, sec-butyl alcohol, tert-butanol, and n-pentanol.

Examples of the reaction accelerator to be used in the reaction include mineral acids such as hydrochloric acid and sulfuric acid; carbodiimides such as dicyclohexylcarbodiimide, diisopropylcarbodiimide, and N'-(3-dimethylaminopropyl)-N-ethylcarbodiimide; organic acids such as methanesulfonic acid and toluenesulfonic acid; Mitsunobu reaction reagents such as triphenylphosphine/diethyl azodicarboxylate; thionyl chloride, boron trifluoride-ethyl ether complex, and the like.

In the reaction, the reaction accelerator is usually used in the proportion within a range of 0.01 to 10 mols based on 1 mol of the compound (XW1).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually used in the proportion within a range of 0.001 to 5 mols based on 1 mol of the compound (XW1).

In the reaction, an excess amount of the compound (XW3) is used based on the compound (XW1).

The reaction temperature of the reaction is usually within a range of −78 to 100° C. The reaction time of the reaction is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process P)

The compound (XW2) can be produced by reacting the compound (XW1) with a halogenating agent to obtain a compound represented by formula (XV1) (hereinafter referred to as the compound (XV1)), and then reacting the compound (XV1) with the compound (XW3):

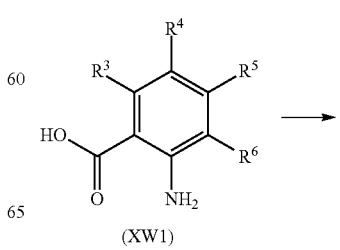

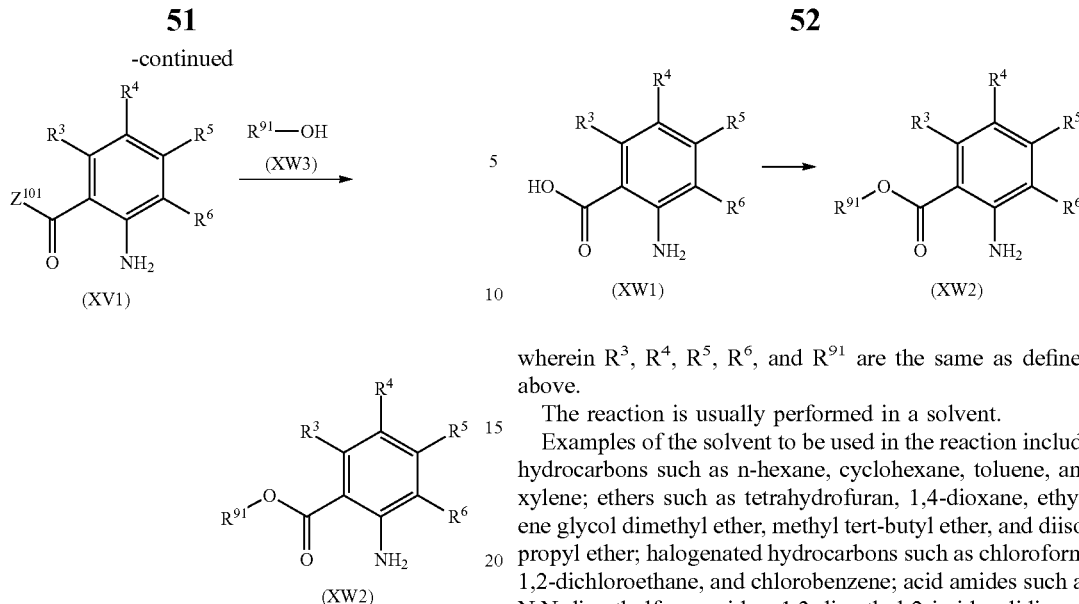

wherein $R^3$, $R^4$, $R^5$, $R^6$, and $R^{91}$ are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the alkylating agent usable in the reaction include halogenated alkyls such as diazomethane, trimethylsilyldiazomethane, chlorodifluoromethane, methyl bromide, and methyl iodide; dialkyl sulfates such as dimethyl sulfate, diethyl sulfate, and di-n-propyl sulfate; and alkyl or arylsulfuric acid esters, such as methyl p-toluenesulfonate, ethyl p-toluenesulfonate, n-propyl p-toluenesulfonate, methyl methanesulfonate, ethyl methanesulfonate, and n-propyl methanesulfonate.

In the reaction, the alkylating agent is usually used in the proportion within a range of 1 to 10 mols based on 1 mol of the compound (XW1).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; quaternary ammonium salt such as tetrabutylammonium hydroxide may be added, and these compounds are usually used in the proportion within a range of 0.001 to 5 mols based on 1 mol of the compound (XW1).

The reaction temperature of the reaction is usually within a range of −78 to 100° C. The reaction time of the reaction is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process R)

A compound represented by formula (XX2) (hereinafter referred to as the compound (XX2)) can be produced by reacting a compound represented by formula (XX1) (hereinafter referred to as the compound (XX1)) with a reducing agent:

wherein $R^3$, $R^4$, $R^5$, $R^6$, $R^{91}$, and $Z^{101}$ are the same as defined above.

The process for producing the compound (XV1) by reacting the compound (XW1) with a halogenating agent can be carried out in accordance with the reaction of Reference Production Process C.

The process for producing the compound (XW2) by reacting the compound (XV1) with the compound (XW3) will be described below.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof; and the compound (XW3) may be used as the solvent.

In the reaction, an excess amount of the compound (XW3) is used based on the compound (XV1).

The reaction temperature of the reaction is usually within a range of −78 to 100° C. The reaction time of the reaction is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process Q)

The compound (XW2) can be produced by reacting the compound (XW1) with an alkylating agent:

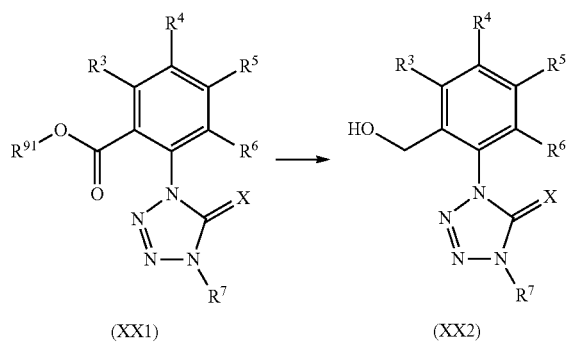

wherein $R^3$, $R^4$, $R^5$, $R^6$, $R^7$, $R^{91}$, and X are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; alcohols such as methanol, ethanol, propanol, and butanol; water; and mixtures thereof.

Examples of the reducing agent usable in the reaction include lithium triethylborohydride, diisobutylaluminum hydride, lithium aminoborohydride, lithium borohydride, sodium borohydride, borane, a borane dimethyl sulfide complex, and a borane tetrahydrofuran complex.

In the reaction, the reducing agent is usually used in the proportion within a range of 1 to 10 mols based on 1 mol of the compound (XX1).

The reaction temperature of the reaction is usually within a range of −78 to 100° C. The reaction time of the reaction is usually within a range of 0.1 to 24 hours.

After completion of the reaction, the compound (XX2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process S)

A compound represented by formula (XZ2) (hereinafter referred to as the compound (XZ2)) can be produced by reacting a compound represented by formula (XZ1) (hereinafter referred to as the compound (XZ1)) with a reducing agent:

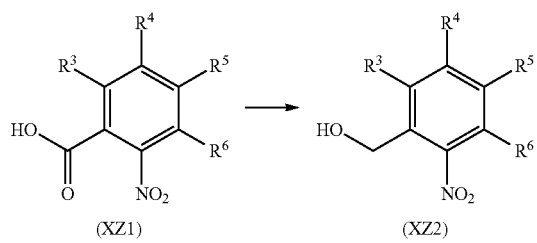

wherein $R^3$, $R^4$, $R^5$, and $R^6$ are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; sulfoxides such as dimethyl sulfoxide; nitriles such as acetonitrile; alcohols such as methanol, ethanol, propanol, and butanol; water; and mixtures thereof.

Examples of the reducing agent usable in the reaction include borane, a borane tetrahydrofuran complex, and a borane dimethyl sulfide complex. It is also possible to use borane generated by mixing borohydride salts such as sodium borohydride and potassium borohydride with acids such as sulfuric acid, hydrochloric acid, methanesulfonic acid, and a boron trifluoride diethyl ether complex.

In the reaction, the reducing agent is usually used in the proportion within a range of 1 to 10 mols based on 1 mol of the compound (XZ1).

The reaction temperature of the reaction is usually within a range of −20 to 100° C. The reaction time of the reaction is usually within a range of 0.1 to 72 hours.

After completion of the reaction, the compound (XZ2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process T)

A compound represented by formula (XS2) (hereinafter referred to as the compound (XS2)) can be produced by reacting a compound represented by formula (XS1) (hereinafter referred to as the compound (XS1)) with the compound (A2) in the presence of a base:

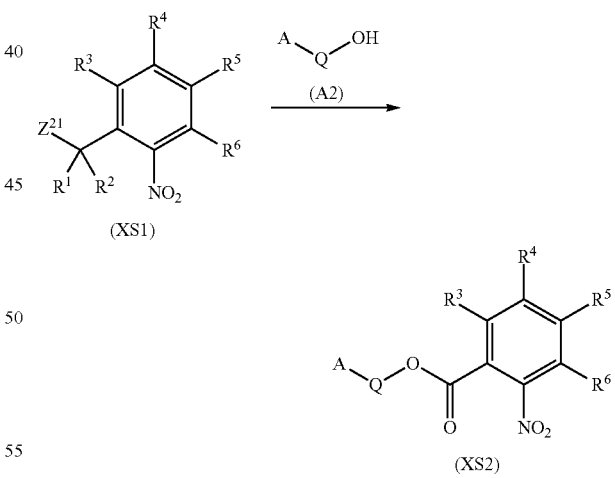

wherein $R^1$, $R^2$, $R^3$, $R^4$, $R^5$, $R^6$, $Z^{21}$, A, and Q are the same as defined above.

The reaction can be carried out in accordance with the reaction of Production Process A.

(Reference Production Process U)

The compound (B1) can be produced by reacting a compound represented by formula (XO1) (hereinafter referred to as the compound (XO1)) with a compound represented by formula (XO2) (hereinafter referred to as the compound (XO2)) in the presence of a base:

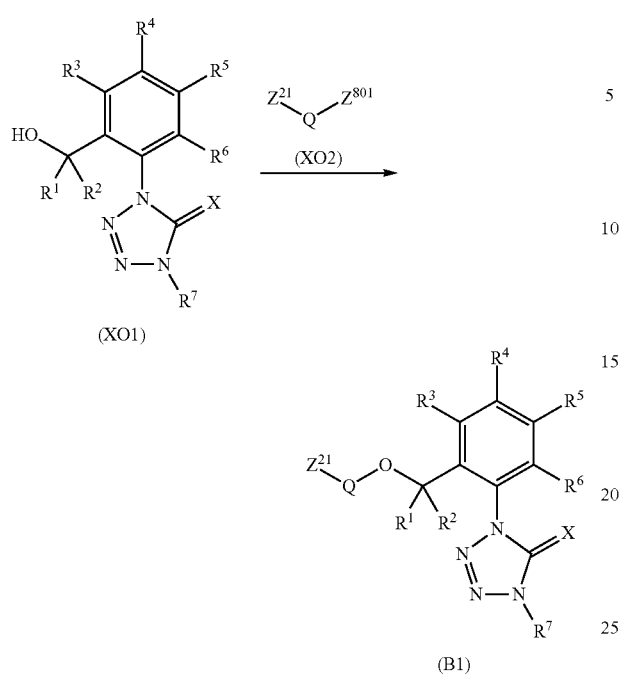

(XO1)

(B1)

wherein $R^1$, $R^2$, $R^3$, $R^4$, $R^5$, $R^6$, $R^7$, $Z^{21}$, $Z^{801}$, Q and X are the same as defined above.

The reaction can be carried out in accordance with the reaction of Production Process A.

(Reference Production Process V)

The compound (B1) can be produced by reacting the compound (A1) with the compound (XU1) in the presence of a base:

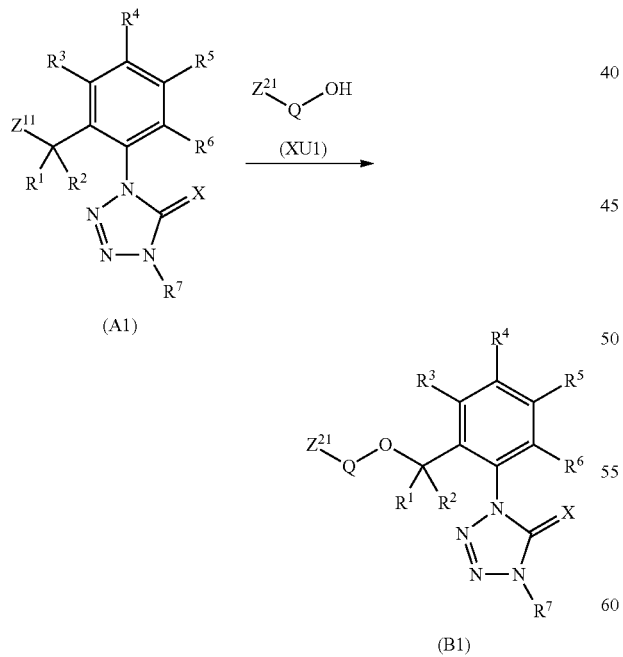

(A1)

(B1)

wherein $R^1$, $R^2$, $R^3$, $R^4$, $R^5$, $R^6$, $R^7$, $Z^{11}$, $Z^{21}$, Q and X are the same as defined above.

The reaction can be carried out in accordance with the reaction of Production Process A.

(Reference Production Process W)

The compound (C1) can be produced by reacting the compound (XO1) with a compound represented by formula (XX1) (hereinafter referred to as the compound (XX1)) in the presence of a base:

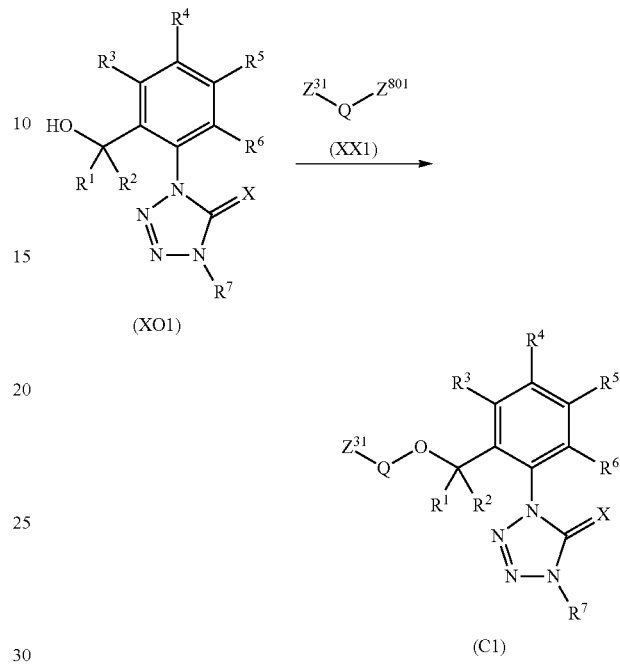

(XO1)

(C1)

wherein $R^1$, $R^2$, $R^3$, $R^4$, $R^5$, $R^6$, $R^7$, $Z^{31}$, Q, and the symbol X are the same as defined above.

The reaction can be carried out in accordance with the reaction of Production Process A.

(Reference Production Process X)

The compound (J1) can be produced by reacting the compound (A1) with a compound represented by formula (XY1) (hereinafter referred to as the compound (XY1)) in the presence of a base:

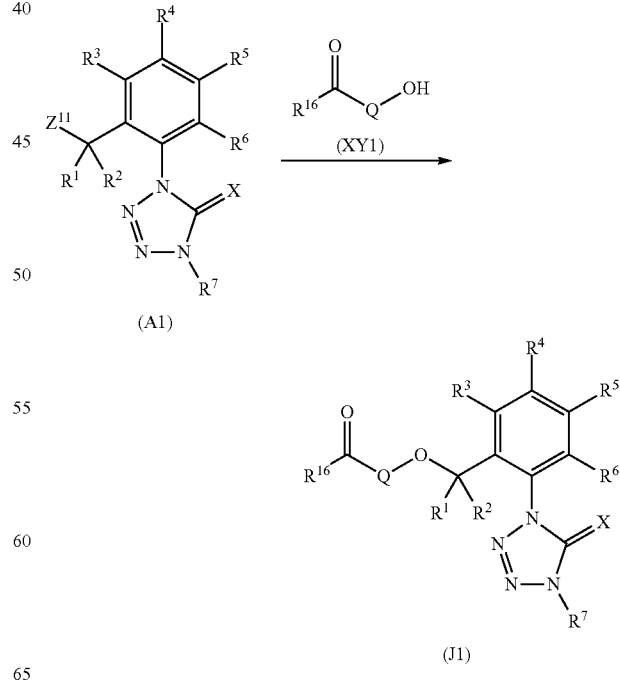

(A1)

(J1)

wherein $R^1$, $R^2$, $R^3$, $R^4$, $R^5$, $R^6$, $R^7$, $R^{16}$, $Z^{11}$, Q and X are the same as defined above.

The reaction can be carried out in accordance with the reaction of Production Process A.

A pest control agent of the present invention includes the present compound and an inert carrier. The pest control agent of the present invention is obtained by mixing the present compound with inert carriers such as solid carriers, liquid carriers, and gaseous carriers, and optionally adding auxiliary agents for formulation, such as surfactants to thereby formulate into emulsifiable concentrates, oil solutions, dusts, granules, wettable powders, flowables, microcapsules, and the like. The present compound is usually contained within a range of 0.01 to 95% by weight.

Examples of the solid carriers used in the formulation include clays (kaolin clay, diatomaceous earth, bentonite, Fubasami clay, and acid clay), synthetic hydrated silicon dioxide, talc, ceramic, other inorganic minerals (sericite, quartz powder, sulfur powder, activated charcoal, calcium carbonate, and hydrated silica), chemical fertilizers (ammonium sulfate, ammonium phosphate, ammonium nitrate, urea, and ammonium chloride) in the form of fine powders or particulates, and synthetic resins (polyester resins such as polypropylene, polyacrylonitrile, methyl polymethacrylate, and polyethylene terephthalate, nylon resins such as nylon-6, nylon-11, and nylon-66, polyamide resin, polyvinyl chloride, polyvinylidene chloride, vinyl chloride-propylene copolymer).

Examples of the liquid carriers include water, alcohols (methanol, ethanol, isopropyl alcohol, butanol, hexanol, benzyl alcohol, ethylene glycol, propylene glycol, and phenoxyethanol), ketones (acetone, methyl ethyl ketone, and cyclohexanone), aromatic hydrocarbons (toluene, xylene, ethylbenzene, dodecylbenzene, phenylxylylethane, methylnaphthalene), aliphatic hydrocarbons (hexane, cyclohexane, kerosene, and light oil), esters (ethyl acetate, butyl acetate, isopropyl myristate, ethyl oleate, diisopropyl adipate, diisobutyl adipate, and propylene glycol monomethyl ether acetate), nitriles (acetonitrile and isobutyronitrile), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, and 3-methoxy-3-methyl-1-butanol), acid amides (N,N-dimethylformamide and N,N-dimethylacetamide), halogenated hydrocarbons (dichloromethane, trichloroethane, and carbon tetrachloride), sulfoxides (dimethyl sulfoxide), propylene carbonate, and vegetable oil (soybean oil and cottonseed oil).

Examples of the gaseous carriers include fluorocarbon, butane gas, liquefied petroleum gas (LPG), dimethyl ether, and carbonic acid gas.

Examples of the surfactants include nonionic surfactants such as polyoxyethylene alkyl ether, polyoxyethylene alkyl aryl ether, and polyethylene glycol fatty acid ester; and anionic surfactants such as alkyl sulfonate, alkylbenzene sulfonate, and alkyl sulfate.

Examples of other auxiliary agents for formulation include stickers, dispersers, colorants and stabilizers, specifically casein, gelatin, saccharides (starch, gum arabic, cellulose derivatives, and alginic acid), lignin derivatives, bentonite, water-soluble synthetic polymers (polyvinyl alcohol, polyvinylpyrrolidone, and polyacrylic acids), PAP (acidic isopropyl phosphate), BHT (2,6-di-tert-butyl-4-methylphenol), and BHA (a mixture of 2-tert-butyl-4-methoxyphenol and 3-tert-butyl-4-methoxyphenol).

Examples of plants, for which the present compound can be used, include the followings.

Crops: corn, rice, wheat, barley, rye, triticale, oat, sorghum, cotton, soybean, peanut, kidney bean, lime bean, adzuki bean, cowpea, mung bean, urd bean, scarlet runner bean, ricebean, moth bean, tepary bean, broad bean, garden pea, chickpea, lentil, lupine, pigeon pea, alfalfa, buckwheat, sugar beet, rapeseed, sunflower, sugar cane, tobacco, and the like;

Vegetables: solanaceous vegetables (for example, eggplant, tomato, pimento, pepper, bell pepper, and potato), cucurbitaceous vegetables (for example, cucumber, pumpkin, zucchini, water melon, melon, and squash), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), umbelliferous vegetables (for example, carrot, parsley, celery, and parsnip), chenopodiaceous vegetables (for example, spinach and Swiss chard), lamiaceous vegetables (for example, *Perilla frutescens*, mint, basil, and lavender), strawberry, sweet potato, *Dioscorea japonica, colocasia*, and the like;

Fruits: pomaceous fruits (for example, apple, pear, Japanese pear, Chinese quince, and quince), stone fruits (for example, peach, plum, nectarine, *Prunus mume*, cherry fruit, apricot, and prune), citrus fruits (for example, Citrus unshiu, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, persimmon, olive, loquat, banana, coffee, date palm, coconuts, and the like;

tea, mulberry, flowering plant, roadside trees (for example, ash, birch, dogwood, *Eucalyptus, Ginkgo biloba*, lilac, maple, *Quercus*, poplar, Judas tree, *Liquidambar formosana*, plane tree, zelkova, Japanese arborvitae, fir tree, hemlock, juniper, *Pinus*, spruce, and yew); flowering plants, foliage plants, zoysia, grasses, and the like.

The above-mentioned plants are not limited as long as cultivars thereof are generally cultivated.

The above-mentioned plants may also be plants bled by hybrid technology.

Namely, plants bled by hybrid technology mean an F1 hybrid obtained by crossbleeding of cultivars of two different lines, and are generally plants having properties of a hybrid vigor (which generally brings an increase in yield potential, improvement in resistance to biotic and abiotic stress factors, and the like) with nature better than those of parents.

Examples of pests, which can be controlled by the present compound, include plant pathogenic bacteria such as filamentous fungi and bacteria, and specific examples include, but are not limited to the followings.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*); Wheat diseases: powdery mildew (*Erysiphe graminis*), fusarium blight (*Fusarium gaminearum, F. avenaceum, F. culmorum, Microdochium nivale*), rust (*Puccinia striiformis, P. graminis, P. recondita*), pink snow mould (*Micronectriella nivale, M. majus*), typhula snow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), tan spot (*Pyrenophora tritici-repentis*), seeding blight caused by *Rhizoctonia* fungus (*Rhizoctonia solani*), and take-all disease (*Gaeumannomyces graminis*); Barley diseases: powdery mildew (*Erysiphe graminis*), fusarium blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia disease (*Ramularia collo-cygni*), and seeding blight caused by *Rhizoctonia* fungus (*Rhizoctonia solani*); Corn diseases: rust (*Puccinia sorghi*), southern rust (*Puccinia polysora*), northern leaf blight (*Setosphaeria turcica*), tropical rust (*Physopella zeae*), southern leaf blight (*Cochliobolus heterostrophus*), anthracnose (*Colletotrichum graminicola*), gray leaf spot (*Cercospora zeae-maydis*), eyespot (*Kabatiella zeae*), and phaeosphaeria leaf spot (*Phaeosphaeria maydis*); Cotton diseases: anthracnose (*Colletotrichum gossypii*), grey mildew (*Ramularia areola*), and alternaria leaf spot (*Alternaria macrospora, A. gossypii*); Coffee diseases: rust (*Hemileia vastatrix*); Rape seed diseases: sclerotinia rot (*Sclerotinia sclerotiorum*), gray leaf spot (*Alternaria brassicae*), and root rot (*Phoma lingam*); Citrus diseases: melanose (*Diaporthe citri*), scab (*Elsinoe fawcetti*), and green mold (*Penicillium digitatum, P. italicum*); Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), bitter rot (*Glomerella cingulata*), brown spot (*Diplocarpon mali*), and ring spot (*Botryosphaeria berengeriana*); Pear diseases: scab (*Venturia nashicola, V. pirina*), black spot (*Alternaria alternata* Japanese pear pathotype), and rust (*Gymnosporangium haraeanum*); Peach diseases: brown rot (*Monilinia fructicola*), scab (*Cladosporium carpophilum*), and Phomopsis rot (*Phomopsis* sp.); Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*); Japanese persimmon diseases: anthracnose (*Gloeosporium kaki*) and leaf spot (*Cercospora kaki, Mycosphaerella nawae*); Diseases of gourd family: anthracnose (*Colletotrichum lagenarium*), powdery mildew (*Sphaerotheca fuliginea*), gummy stem blight (*Didymella bryoniae*), *Corynespora* leaf spot (*Corynespora cassiicola*), fusarium wilt (*Fusarium oxysporum*), downy mildew (*Pseudoperonospora cubensis*), phytophthora rot (*Phytophthora* sp.), and damping-off (*Pythium* sp.); Tomato diseases: early blight (*Alternaria solani*), leaf mold (*Cladosporium fulvum*), leaf mold (*Pseudocercospora fuligena*), and late blight (*Phytophthora infestans*), powdery mildew (*Leveillula taurica*); Eggplant diseases: brown spot (*Phomopsis vexans*) and powdery mildew (*Erysiphe cichoracearum*); Cruciferous vegetables diseases: alternaria leaf spot (*Alternaria japonica*), white spot (*Cercosporella brassicae*), clubroot (*Plasmodiophora brassicae*), and downy mildew (*Peronospora parasitica*); Welsh onion diseases: rust (*Puccinia allii*); Soybean diseases: purple stain (*Cercospora kikuchii*), sphaceloma scad (*Elsinoe glycines*), pod and stem blight (*Diaporthe phaseolorum* var. *sojae*), rust (*Phakopsora pachyrhizi*), target spot (*Corynespora cassiicola*), anthracnose (*Colletotrichum glycines, C. truncatum*), *Rhizoctonia* aerial blight (*Rhizoctonia solani*), septoria brown spot (*Septoria glycines*), and frog eye leaf spot (*Cercospora sojina*); Kidney bean diseases: anthracnose (*Colletotrichum lindemuthianum*); Peanut diseases: leaf spot (*Cercospora personata*), Brown leaf spot (*Cercospora arachidicola*), and southern blight (*Sclerotium rolfsii*); Garden pea diseases: powdery mildew (*Erysiphe pisi*); Potato diseases: early blight (*Alternaria solani*), late blight (*Phytophthora infestans*), and verticillium wilt (*Verticillium albo-atrum, V. dahliae, V. nigrescens*); Strawberry diseases: powdery mildew (*Sphaerotheca humuli*); Tea diseases: net blister blight (*Exobasidium reticulatum*), white scab (*Elsinoe leucospila*), gray blight (*Pestalotiopsis* sp.), and anthracnose (*Colletotrichum theae-sinensis*); Tobacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*); Sugar beet diseases: cercospora leaf spot (*Cercospora beticola*), leaf blight (*Thanatephorus cucumeris*), root rot (*Thanatephorus cucumeris*), and aphanomyces root rot (*Aphanomyces cochlioides*); Rose diseases: black spot (*Diplocarpon rosae*) and powdery mildew (*Sphaerotheca pannosa*); *Chrysanthemum* diseases: leaf blight (*Septoria chrysanthemi-indici*) and white rust (*Puccinia horiana*); Onion diseases: botrytis leaf blight (*Botrytis cinerea, B. byssoidea, B. squamosa*), gray-mold neck rot (*Botrytis allii*), and small sclerotial rot (*Botrytis squamosa*); various crops diseases: gray mold (*Botrytis cinerea*) and sclerotinia rot (*Sclerotinia sclerotiorum*); Japanese radish diseases: alternaria leaf spot (*Alternaria brassicicola*); Turfgrass diseases: dollar spot (*Sclerotinia homoeocarpa*) and brown patch and large patch (*Rhizoctonia solani*); and Banana diseases: Sigatoka disease (*Mycosphaerella fijiensis, Mycosphaerella musicola*).

Seed diseases or diseases in the early growth phase in various crops caused by bacteria from genera of *Aspergillus, Penicillium, Fusarium, Gibberella, Tricoderma, Thielaviopsis, Rhizopus, Mucor, Corticium, Phoma, Rhizoctonia, Diplodia*, and the like.

Viral diseases intermediated by genera of *Polymyxa, Olpidium*, or the like in various crops.

Rice damping-off (*Burkholderia plantarii*); cucumber bacterial blight (*Pseudomonas syringae* pv. *Lachrymans*); eggplant bacterial wilt disease (*Ralstonia solanacearum*), citrus canker (*Xanthomonas citiri*); Chinese cabbage soft rod (*Erwinia carotovora*) and the like.

Examples of pests, against which the present compound has control activity, include pests such as pest insects and pest mites. Specific examples of these pests include, but are not limited, to the followings.

Hemiptera: planthoppers such as small brown planthopper (*Laodelphax striatellus*), brown rice planthopper (*Nilaparvata lugens*), white-backed rice planthopper (*Sogatella furcifera*), and corn planthopper (*Peregrinus maidis*); leafhoppers such as green rice leafhopper (*Nephotettix cincticeps*), Taiwan green rice leafhopper (*Nephotettix virescens*), rice green leafhopper (*Nephotettix nigropictus*), zig-zag rice leafhopper (*Recilia dorsalis*), tea green leafhopper (*Empoasca onukii*), potato leafhopper (*Empoasca fabae*), corn leafhopper (*Dalbulus maidis*), Sugarcane froghopper (*Mahanarva posticata*), Sugarcane root spittlebug (*Mahanarva fimbriolata*), white giant leafhopper (*Cofana spectra*), cross-di-green rice leafhopper (*Nephotettix nigropictus*), and zig-zag rice leafhopper (*Recilia dorsalis*); aphids such as cotton aphid (*Aphis gossypii*), green peach aphid (*Myzus persicae*), cabbage aphid (*Brevicoryne brassicae*), spiraea aphid (*Aphis spiraecola*), tulip aphid (*Macrosiphum euphorbiae*), potato aphid (*Aulacorthum solani*), oat bird-cherry aphid (*Rhopalosiphum padi*), tropical citrus aphid (*Toxoptera citricidus*), mealy plum aphid (*Hyalopterus pruni*), soybean aphid (*Aphis glycines* Matsumura), corn aphid (*Rhopalosiphum maidis*), rice root aphid (*Tetraneura nigriabdominalis*), grape root aphid (*Viteus vitifoliae*), grape phylloxera (*Daktulosphaira vitifoliae*), pecan *phylloxera* (*Phylloxera devastatrix* Pergande), pecan leaf *phylloxera* (*Phylloxera notabilis* pergande), and southern pecan leaf

*phylloxera* (*Phylloxera russellae* Stoetzel); stink bugs such as Japanese black rice bug (*Scotinophara lurida*), Malayan rice black bug (*Scotinophara coarctata*), green stink bug (*Nezara antennata*), white spotted spined bug (*Eysarcoris parvus*), stink bug (*Halyomorpha mista*), southern green stink bug (*Nezara viridula*), Brown stink bug (*Euschistus heros*), Southern green stink bug (*Nezara viridula*), Red banded stink bug (*Piezodorus guildinii*), Burrower brown bug (*Scaptocoris castanea*), *Oebalus pugnax*, and *Dichelops melacanthus*; broad-headed bugs such as bean bug (*Riptortus clavetus*), rice bug (*Leptocorisa chinensis*), rice seed bug (*Leptocorisa acuta*), and *Leptocorisa* genus; plant bugs such as rice leaf bug (*Trigonotylus caelestialium*), sorghum plant bug (*Stenotus rubrovittatus*), tarnished plant bug (*Lygus lineolaris*), and chinchi bug (*Blissus leucopterus leucopterus*); whiteflies such as greenhouse whitefly (*Trialeurodes vaporariorum*), tobacco whitefly (*Bemisia tabaci*), citrus whitefly (*Dialeurodes citri*), and orange spiny whitefly (*Aleurocanthus spiniferus*); scales such as California red scale (*Aonidiella aurantii*), san Jose scale (*Comstockaspis perniciosa*), citrus north scale (*Unaspis citri*), red wax scale (*Ceroplastes rubens*), cottony cushion scale (*Icerya purchasi*), Japanese mealybug (*Planococcus kraunhiae*), comstock mealybug (*Pseudococcus longispinus*), white peach scale (*Pseudaulacaspis pentagona*), and tuttle mealybug (*Brevennia rehi*); psylla such as Asian citrus psyllid (*Diaphorina citri*), pear sucker (*Psylla pyrisuga*), and potato psyllid (*Bactericerca cockerelli*); lace bugs such as pear lace bug (*Stephanitis nashi*); bed bugs such as bed bug (*Cimex lectularius*); and Giant Cicada (*Quesada gigas*).

Lepidoptera: pyralid moths such as rice stem borer (*Chilo suppressalis*), Darkheaded stm borer (*Chilo polychrysus*), yellow rice borer (*Tryporyza incertulas*), tropical borer (*Chilo suppressalis*), white rice borer (*Scirpophaga innotata*), Yellow stem borer (*Scirpophaga incertulas*), Pink borer (*Sesamia inferens*), Rupela albinellam, rice leafroller (*Cnaphalocrocis medinalis*), Marasmia patnalis, Marasmia exigna, cotton leafroller (*Notarcha derogata*), Indian meal moth (*Plodia interpunctella*), oriental corn borer (*Ostrinia furnacalis*), cabbage webworm (*Hellula undalis*), bluegrass webworm (*Pediasia teterrellus*), Rice Caseworm (*Nymphula depunctalis*), Marasmia genus, Hop vine borer (*Hydraecia immanis*), European corn borer (*Ostrinia nubilalis*), Lesser cornstalk borer (*Elasmopalpus lignosellus*), Bean Shoot Borer (*Epinotia aporema*), Sugarcane borer (*Diatraea saccharalis*), and Giant Sugarcane borer (*Telchin licus*); owlet moths such as common cutworm (*Spodoptera litura*), beet armyworm (*Spodoptera exigua*), armyworm (*Pseudaletia separata*), cabbage armyworm (*Mamestra brassicae*), pink borer (*Sesamia inferens*), lawn armyworm (*Spodoptera mauritia*), fall armyworm (*Spodoptera frugiperda*), *Spodoptera exempta*, black cutworm (*Agrotis ipsilon*), beet semilooper (*Plusia nigrisigna*), Soybean looper (*Pseudoplusia includens*), *Thoricoplusia* genus, *Heliothis* genus such as oriental tobacco budworm (*Heliothis virescens*), *Helicoverpa* genus such as corn earworm (*Helicoverpa armigera*), velvetbean caterpillar (*Anticarsia gemmatalis*), and Cotton leafworm (*Alabama argillacea*); white butterflies such as common white (*Pieris rapae*); tortricid moths such as *Adoxophyes* genus, oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxophyes honmai.*), oriental tea tortrix (*Homona magnanima*), apple tortrix (*Archips fuscocupreanus*), and codling moth (*Cydia pomonella*); leafblotch miners such as tea leafroller (*Caloptilia theivora*); fruitworm moths such as peach fruit moth (*Carposina niponensis*) and Citrus fruit borer (*Ecdytolopha aurantiana*); lyonetiid moths such as coffee Leaf miner (*Leucoptera coffeela*) and *Lyonetia* genus; tussock moths such as *Lymantria* genus and *Euproctis* genus; yponomeutid moths such as diamondback (*Plutella xylostella*); gelechild moths such as pink bollworm (*Pectinophora gossypiella*); gelechiid moths such as potato tubeworm (*Phthorimaea operculella*); tiger moths such as fall webworm (*Hyphantria cunea*).

Thysanoptera: *thrips* such as yellow citrus *thrips* (*Frankliniella occidentalis*), melon *thrips* (*Thrips palmi*), yellow tea *thrips* (*Scirtothrips dorsalis*), onion *thrips* (*Thrips tabaci*), flower *thrips* (*Frankliniella intonsa*), western flower *thrips* (*Frankliniella occidentalis*), rice aculeated *thrips* (*Haplothrips aculeatus*), and rice *thrips* (*Stenchaetothrips biformis*).

Diptera: anthomyiid flies such as seedcorn maggot (*Delia platura*), onion maggot (*Delia antiqua*), and sugar beet root maggot (*Tetanops myopaeformis*); leafminers such as rice leafminer (*Agromyza oryzae*), rice leafminer (*Hydrellia griseola*), tomato leafminer (*Liriomyza sativae*), bean leafminer (*Liriomyza trifolii*), and garden pea leafminer (*Chromatomyia horticola*); grass flies such as rice stem maggot (*Chlorops oryzae*); fruit flies such as melon fly (*Dacus cucurbitae*) and Mediterranean fruit fly (*Ceratitis capitata*); shore flies such as oriental rice whorl maggot (*Hydrellia philippina*), and rice whorl maggot (*Hydrellia sasakii*); drosophila; phorid flies such as humpbacked fly (*Megaselia spiracularis*); moth flies such as bath room fly (*Clogmia albipunctata*); Sciarid flies. Gall midges such as Hessian fly (*Mayetiola destructor*) and rice gall midge (*Orseolia oryzae*); Stalk-eyed flies such as Diopsis macrophthalma; craneflies such as Common cranefly (*Tipula oleracea*) and European cranefly (*Tipula paludosa*).

Coleoptera: leaf beetles such as western corn rootworm (*Diabrotica virgifera virgifera*), southern corn rootworm (*Diabrotica undecimpunctata howardi*), northern corn rootworm (*Diabrotica barberi*), Mexican corn rootworm (*Diabrotica virgifera zeae*), banded cucumber beetle (*Diabrotica balteata LeConte*), San Antonio beetle (*Diabrotica speciosa*), Cucurbit Beetle (*Diabrotica speciosa*), bean leaf beetle (*Cerotoma trifurcata*), cereal leaf beetle (*Oulema melanopus*), cucurbit leaf beetle (*Aulacophora femoralis*), yellow striped flea beetle (*Phyllotreta striolata*), colorado potato beetle (*Leptinotarsa decemlineata*), rice leaf beetle (*Oulema oryzae*), grape colaspis (*Colaspis brunnea*), corn flea beetle (*Chaetocnema pulicaria*), potato flea beetle (*Epitrix cucumeris*), rice hispa (*Dicladispa armigera*), Seedcorn beetle (*Stenolophus lecontei*), and Slender seedcorn beetle (*Clivinia impressifrons*); chafers such as cupreous chafer (*Anomala cuprea*), soybean beetle (*Anomala rufocuprea*), Japanese beetle (*Popillia japonica*), European chafer (*Rhizotrogus majalis*), carrot beetle (*Bothynus gibbosus*), Grape Colaspis (*Colaspis brunnea*), southern corn leaf beetle (*Myochrous denticollis*), *Holotrichia* genus, *Phyllophaga* genus, for example June beetle (*Phyllophaga crinita*); rice plant weevils such as maize weevil (*Sitophilus zeamais*), rice plant weevil (*Echinocnemus squameus*), rice water weevil (*Lissorhoptrus oryzophilus*), and hunting billbug (*Sphenophorus venatus*); weevils such as boll weevil (*Anthonomus grandis*), southern corn billbug (*Sphenophorus callosus*), Soybean stalk weevil (*Sternechus subsignatus*) and *Sphenophorus* genus, for example *Sphenophorus levis*; *Epilachna* such as twenty-eight-spotted ladybirds (*Epilachna vigintioctopunctata*); bark beetles such as powder post beetle (*Lyctus brunneus*) and pine shoot beetle (*Tomicus piniperda*); larger grain borers; museum beetles;

longicorn beetles such as white-spotted longicorn beetle (*Anoplophora malasiaca*) and *Migdolus fryanus*; click beetles (*Agriotes* sp., *Aelous* sp., *Anchastus* sp., *Melanotus* sp., *Limonius* sp., *Conoderus* sp., *Ctenicera* sp.) such as sugarcane wireworm (*Melanotus okinawensis*), barley wireworm (*Agriotes ogurae fuscicollis*), and click beetle (*Melanotus legatus*); staphylinids such as rove beetles (*Paederus fuscipes*); and Coffee Barry Borer (*Hypothenemus hampei*).

Orthoptera: crickets such as asiatic locusts (*Locusta migratoria*), African mole cricket (*Gryllotalpa africana*), Moroccan locust (*Dociostaurus maroccanus*), Australian plague locust (*Chortoicetes terminifera*), red locust (*Nomadacris septemfasciata*), brown locust (*Locustana pardalina*), tree locust (*Anacridium melanorhodon*), Italian locust (*Calliptamus italicus*), differential grasshopper (*Melanoplus differentialis*), twostriped grasshopper (*Melanoplus bivittatus*), migratory grasshopper (*Melanoplus sanguinipes*), red-legged grasshopper (*Melanoplus femurrubrum*), clear-winged grasshopper (*Camnula pellucida*), desert locust (*Schistocerca gregaria*), yellow-winged locust (*Gastrimargus musicus*), spur-throated locust (*Austracris guttulosa*), rice grasshopper (*Oxya yezoensis*), Japanese grasshopper (*Oxya japonica*), Bombay locust (*Patanga succincta*), house cricket (*Acheta domesticus*), emma field cricket (*Teleogryllus emma*), and Mormon cricket (*Anabrus simplex*).

Hymenoptera: sawflies such as cabbage sawflies (*Athalia rosae*) and Japanese cabbage sawfly (*Athalia japonica*). Fire ants. Leaf cutting ants such as Brown leaf-cutting ant (*Atta capiguara*).

Nematodes: white-tip nematode (*Aphelenchoides besseyi*), strawberry bud nematode (*Nothotylenchus acris*), southern root-knot nematode (*Meloidogyne incognita*), northern root-knot nematode (*Meloidogyne hapla*), javanese root-knot nematode (*Meloidogyne javanica*), soybean cyst nematode (*Heterodera glycines*), golden nematode (*Globodera rostochiensis*), coffee root-lesion nematode (*Pratylenchus coffeae*), california root-lesion nematode (*Pratylenchus neglectus*), *Meloidogyne javanica*, *Meloidogyne incognita*, *Rotylenchulus reniformis*, and *Pratylenchus brachyurus*.

Blattariae: German cockroach (*Blattella germanica*), smoky-brown cockroach (*Periplaneta fuliginosa*), American cockroach (*Periplaneta americana*), brown cockroach (*Periplaneta brunnea*), and oriental cockroach (*Blatta orientalis*).

Isoptera: Japanese subterranean termite (*Reticulitermes speratus*), formosan subterranean termite (*Coptotermes formosanus*), western drywood termite (*Incisitermes minor*), drywood termite (*Cryptotermes domesticus*), Taiwan termite (*Odontotermes formosanus*), Kosyun termite (*Neotermes koshunensis*), Satsuma termite (*Glyptotermes satsumensis*), Nakajima termite (*Glyptotermes nakajimai*), Katan termite (*Glyptotermes fuscus*), Kodama termite (*Glyptotermes kodamai*), Kushimoto termite (*Glyptotermes kushimensis*), Japanese damp-wood termite (*Hodotermopsis japonica*), Koshu formosan termite (*Coptotermes guangzhoensis*), Amami termite (*Reticulitermes miyatakei*), Kiashi termite (*Reticulitermes flaviceps amamianus*), Kanmon termite (*Reticulitermes* sp.), Takasago termite (*Nasutitermes takasagoensis*), Nitobe termite (*Pericapritermes nitobei*), Musya termite (*Sinocapritermes mushae*), Cornitermes cumulans, and the like.

Acarina: Tetranychidae such as two-spotted spider mite (*Tetranychus urticae*), kanzawa spider mite (*Tetranychus kanzawai*), citrus red mite (*Panonychus citri*), European red mite (*Panonychus ulmi*), *Oligonychus* genus and southern turkey spider mites (*Brevipalpus phoenicis*); Eriophyidae such as pink citrus rust mite (*Aculops pelekassi*), Ryukyu tangerine rust mite (*Phyllocoptruta citri*), tomato russet mite (*Aculops lycopersici*), tea rust mite (*Calacarus carinatus*), tea Roh Naga rust mite (*Acaphylla theavagrans*), fake pear rust mite (*Eriophyes chibaensis*), and apple rust mite (*Aculus schlechtendali*); Tarsonemidae such as tea dust mite (*Polyphagotarsonemus latus*); Tenuipalpidae such as Southern Hime spider mite (*Brevipalpus phoenicis*); Tuckerellidae; Ixodidae such as cattle tick (*Haemaphysalis longicornis*), Yamatochi tick (*Haemaphysalis flava*), Taiwan Kaku tick (*Dermacentor taiwanicus*), American dog Kaku tick (*Dermacentor variabilis*), tick (*Ixodes ovatus*), Schultz tick (*Ixodes persulcatus*), black-legged tick (*Ixodes scapularis*), lone star tick (*Amblyomma americanum*), Oshima tick (*Boophilus microplus*), and brown dog tick (*Rhipicephalus sanguineus*); Acaridae such as common grain mite (*Tyrophagus putrescentiae*) and spinach common grain mite (*Tyrophagus similis*); Pyroglyphidae such as American house dust mite (*Dermatophagoides farinae*) and house dust mite (*Dermatophagoides pteronyssinus*).

Cheyletidae such as cheyletid mite (*Cheyletus eruditus*), Stag Tsumedani (*Cheyletus malaccensis*), Minami Tsumedani (*Cheyletus moorei*), and Inutsumedani (*Cheyletiella yasguri*); Cheyletidae such as ear mite (*Otodectes cynotis*) and itch mite (*Sarcoptes scabiei*); Demodicidae such as dog follicle mite (*Demodex canis*); Listrophoridae; Oribatulidae; Dermanyssidae such as tropical rat mite (*Ornithonyssus bacoti*), northern fowl mite (*Ornithonyssus sylvairum*), and red mite (*Dermanyssus gallinae*); Trombiculidae such as blue chigger (*Leptotrombidium akamushi*); and Araneida such as Japanese foliage spider (*Chiracanthium japonicum*) and red back spider (*Latrodectus hasseltii*).

Chilopoda: house centipede (*Thereuonema hilgendorfi*), Chinese red headed centipede (*Scolopendra subspinipes*) and the like.

Diplopoda: garden millipede (*Oxidus gracilis*), garden millipede (*Nedyopus tambanus*) and the like.

Isopoda: pill bug (*Armadillidium vulgare*) and the like.

Gastropoda: tree slug (*Limax marginatus*), yellow slug (*Limax flavus*) and the like.

Target pest insects and pest mites may also be insects and mites each having reduced chemical sensitivity or enhanced chemical resistance to insecticides and acaricides. When chemical sensitivity is significantly reduced or chemical resistance is significantly enhanced, use of the present composition containing insecticides and acaricides other than target insecticides and acaricides is desirable.

The present compound can also be used to protect plants from plant diseases due to insect-borne virus.

Examples of plant diseases caused by insect-borne viruses, against which the present compound has control activity, include the followings.

Rice waika (Rice waika virus), rice tungro (Rice tungro spherical virus, Rice tungro bacilliform virus), rice grassy stunt (Rice grassy stunt virus), rice ragged stunt (Rice ragged stunt virus), rice stripe (Rice stripe virus), rice black streaked dwarf (Rice black streaked dwarf virus), southern rice black-streaked dwarf (Southern rice black-streaked dwarf virus), rice gall dwarf (Rice gall dwarf virus), rice hoja blanca (Rice hoja blanca virus), rice white leaf (White leaf disease of rice), yellow dwarf (Yellow dwarf virus), red disease (Rice penyakit merah virus), rice yellow stunt (Rice yellow stunt virus), rice transitory yellowing (Rice transitory yellowing virus), rice yellow mottle (Rice Yellow Mottle Virus), rice necrosis mosaic (Rice necrosis mosaic virus), rice dwarf stunt (Rice dwarf stunt virus), northern cereal mosaic (Northern Cereal Mosaic Virus), barley yellow dwarf (Barley Yellow Dwarf Virus), wheat yellow dwarf (Wheat yellow dwarf virus), Oat sterile dwarf (Oat sterile dwarf virus), wheat streak mosaic (Wheat streak mosaic virus), maize dwarf mosaic (Maize dwarf mosaic virus), maize stripe disease (maize stripe tenuivirus), maize chlorotic dwarf (Maize chlorotic dwarf virus), maize chlorotic mottle (maize chlorotic mottle virus), maize rayado fino (maize rayado fino marafivirus), corn stunt (Corn stunt spiroplasma), maize bushy stunt (Maize bushy stunt phytoplasma), sugarcane mosaic (Sugarcane mosaic virus), soybean mild mosaic (Soybean mild mosaic virus), alfalfa mosaic (Alfalfa Mosaic Virus, Bean yellow-spot mosaic virus, Soybean mosaic virus, Bean yellow mosaic virus, Cowpea severe mosaic virus), broad bean wilt (Broad bean wilt virus, Bean common mosaic virus, Peanut stunt virus, Southern bean mosaic virus), soybean dwarf (Soybean dwarf luteovirus, Milk-vetch dwarf luteovirus), bean-pod mottle (Bean-pod mottle virus), brazilian bud blight (Tobacco streak virus), cowpea chlorotic mottle (Cowpea chlorotic mottle), mung bean yellow mosaic (Mung bean yellow mosaic virus), peanut stripe (Peanut stripe mottle), soybean crinkle leaf (Soybean crinkle leaf virus), soybean severe stunt (Soybean severe stunt virus), tomato chlorosis (Tomato chlorosis virus), tomato spotted wilt (Tomato spotted wilt virus), tomato yellow leaf curl (Tomato yellow leaf curl virus), melon yellow spot (Melon yellow spot virus), watermelon mosaic (Watermelon mosaic virus), cucumber mosaic (Cucumber mosaic virus), zucchini yellow mosaic (Zucchini yellow mosaic virus), turnip mosaic (Turnip mosaic virus), cucurbit chlorotic yellows (Cucurbit chlorotic yellows virus), capsicum chlorosis (Capsicum chlorosis virus), beet pseudo yellows (Beet pseudo yellows virus), chrysanthemum stem necrosis (chrysanthemum stem necrosis virus), impatiens necrotic spot (Impatiens necrotic spot virus), iris yellow spot (Iris yellow spot virus), sweet potato internal cork (Sweet potato internal cork virus), sweet potato shukuyo mosaic (Sweet potato shukuyo mosaic virus), and mosaic virus diseases of various plants transmitted by the genus Polymyxa or Olpidium.

The formulation comprising the present compound or salts thereof can be used in the field relating to a treatment of livestock diseases or livestock industry, and can exterminate the living things or parasites which are parasitic on the inside and/or the outside of vertebrates such as human being, cow, sheep, pig, poultry, dog, cat, and fish, so as to maintain public health. Examples of the pests include ticks (*Ixodes* spp.) (for example, *Ixodes scapularis*), *Boophilus* spp. (for example, cattle tick (*Boophilus microplus*)), *Amblyomma* spp., *Hyalomma* spp., *Rhipicephalus* spp. (for example, kennel tick (*Rhipicephalus sanguineus*)), *Haemaphysalis* spp. (for example, *Haemaphysalis longicornis*), *Dermacentor* spp., *Ornithodoros* spp. (for example, *Ornithodoros moubata*), red mite (*Dermanyssus gallinae*), ghost ant (*Ornithonyssus sylviarum*), *Sarcoptes* spp. (for example, *Sarcoptes scabiei*), *Psoroptes* spp., *Chorioptes* spp., *Demodex* spp., *Eutrombicula* spp., *Aedes* spp. (for example, Asian tiger mosquito (*Aedes albopictus*)), *Anopheles* spp., *Culex* spp., *Culicoides* spp., *Musca* spp., *Hypoderma* spp., *Gasterophilus* spp., *Haematobia* spp., *Tabanus* spp., *Simulium* spp., *Triatoma* spp., lice (*Phthiraptera*) (for example, *Damalinia* spp., *Linognathus* spp., *Haematopinus* spp.), *Ctenocephalides* spp. (for example, cat flea (*Ctenocephalides felis*)) *Xenopsylla* spp., Pharaoh's ant (*Monomorium pharaonic*) and nematodes [for example, hairworm (for example, *Nippostrongylus brasiliensis*, *Trichostrongylus axei*, *Trichostrongylus colubriformis*), *Trichinella* spp. (for example, *Trichinella spiralis*), barber pole worm (*Haemonchus contortus*), *Nematodirus* spp. (for example, *Nematodirus battus*), *Ostertagia circumcincta*, *Cooperia* spp., *Hymenolepis nana*, and the like.

EXAMPLES

The present invention will be described in more detail below by way of Production Examples, Formulation Examples, and Test Examples, but the present invention is not limited to these Examples.

First, Production Examples will be described.

Production Example 1

A mixture of 0.28 g of 1-[2-(bromomethyl)-3-methylphenyl]-4-methyl-1,4-dihydrotetrazol-5-one1-[2-(bromomethyl)-3-methylphenyl]-4-methyl-1,4-dihydrotetrazol-5-one mentioned in Reference Production Example 14, 0.19 g of 3-phenoxyphenol, 0.28 g of potassium carbonate, and 4 mL of acetonitrile was stirred with heating under reflux for 4 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.20 g of 1-{2-[(3-phenoxyphenoxy)methyl]-3-methylphenyl}-4-methyl-1,4-dihydrotetrazol-5-one (hereinafter referred to as the present compound 1).

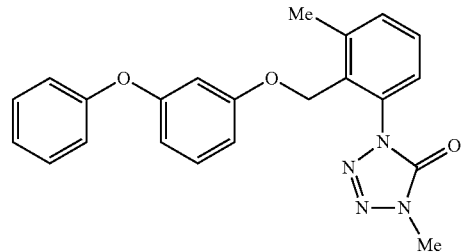 [SMILES: Cc1cccc(-n2nnn(C)c2=O)c1COc1cccc(Oc2ccccc2)c1]

$^1$H-NMR (CDCl3) δ: 7.43-7.31 (4H, m), 7.31-7.25 (1H, m), 7.19 (1H, t, J=8.1 Hz), 7.13-7.09 (1H, m), 7.04-6.98 (2H, m), 6.62-6.53 (3H, m), 4.99 (2H, s), 3.62 (3H, s), 2.47 (3H, s).

In accordance with the reaction of Production Example 1, the present compounds 2 to 9, 26 to 29, 31, 44, and 47 were synthesized using compounds or commercially available compounds mentioned in Reference Production Examples.

The structural formulas and $^1$H-NMR data thereof are shown below.

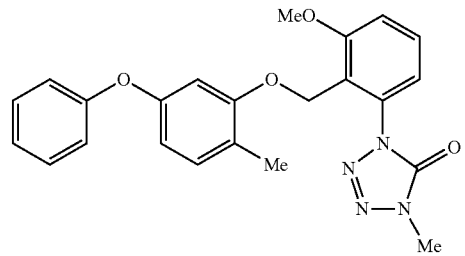

Present Compound 2

-continued
Present Compound 3
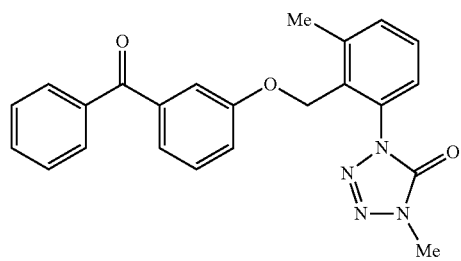
Present Compound 4
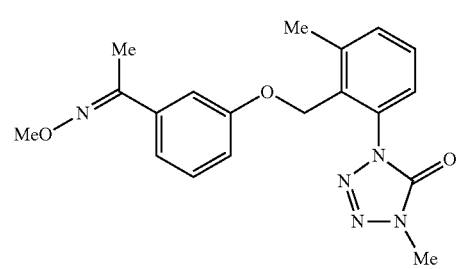
Present Compound 5
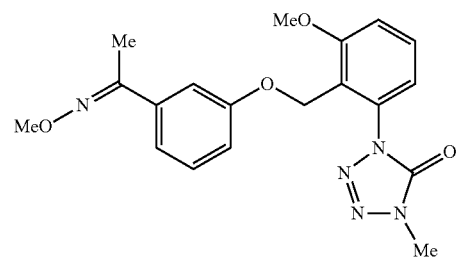
Present Compound 6
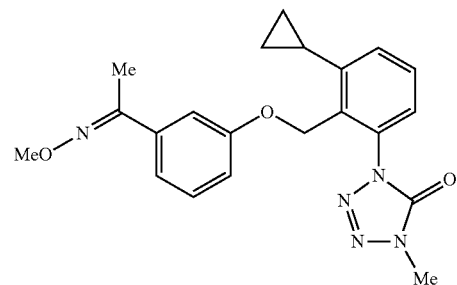
Present Compound 7
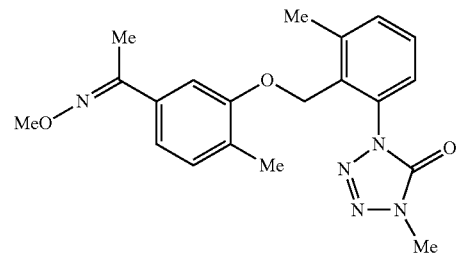
-continued
Present Compound 8
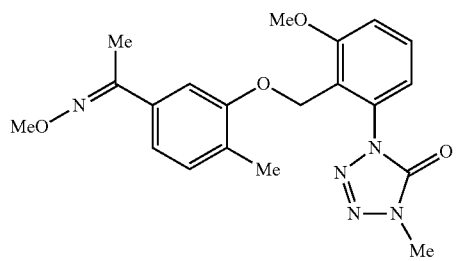
Present Compound 9
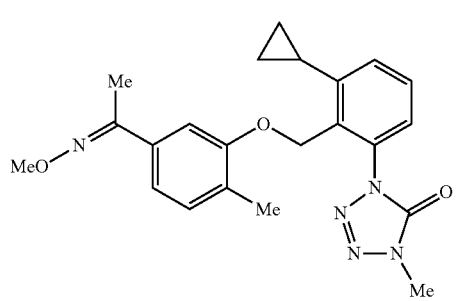
Present Compound 26
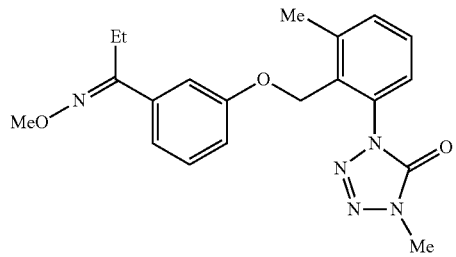
Present Compound 27
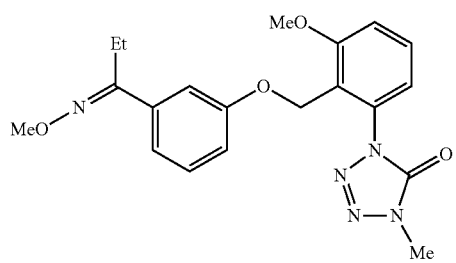
Present Compound 28
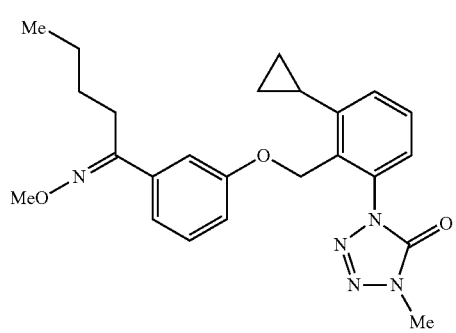

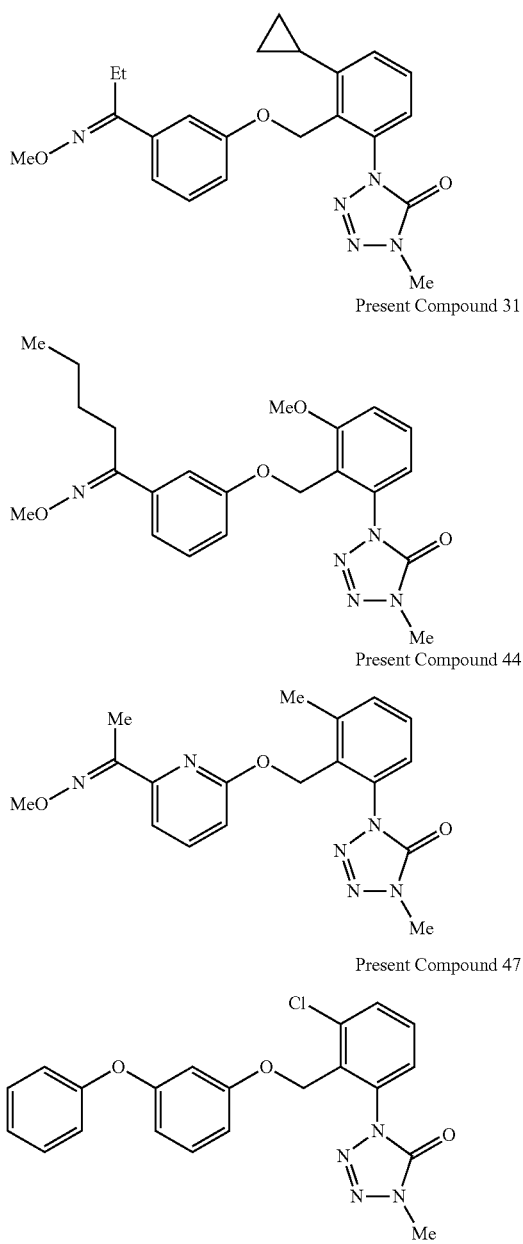

Present Compound 2

¹H-NMR (CDCl3) δ: 7.44 (1H, t, J=8.2 Hz), 7.32-7.26 (2H, m), 7.09-7.05 (2H, m), 7.02-6.97 (2H, m), 6.97-6.93 (2H, m), 6.64 (1H, d, J=2.3 Hz), 6.47 (1H, dd, J=8.0, 2.3 Hz), 5.25 (2H, s), 3.77 (3H, s), 3.64 (3H, s), 1.96 (3H, s).

Present Compound 3

¹H-NMR (CDCl3) δ: 7.81-7.78 (2H, m), 7.62-7.56 (1H, m), 7.50-7.39 (4H, m), 7.38-7.32 (3H, m), 7.29-7.26 (1H, m), 7.10-7.07 (1H, m), 5.08 (2H, s), 3.64 (3H, s), 2.50 (3H, s).

Present Compound 4

¹H-NMR (CDCl3) δ: 7.45-7.37 (2H, m), 7.30-7.16 (4H, m), 6.90-6.84 (1H, m), 5.05 (2H, s), 3.99 (3H, s), 3.62 (3H, s), 2.50 (3H, s), 2.19 (3H, s).

Present Compound 5

¹H-NMR (CDCl3) δ: 7.46 (1H, t, J=8.2 Hz), 7.25-7.16 (2H, m), 7.14-7.04 (3H, m), 6.83-6.80 (1H, m), 5.24 (2H, s), 3.99 (3H, s), 3.92 (3H, s), 3.59 (3H, s), 2.18 (3H, s).

Present Compound 6

¹H-NMR (CDCl3) δ: 7.43 (1H, t, J=7.8 Hz), 7.29-7.17 (5H, m), 6.91-6.86 (1H, m), 5.27 (2H, s), 3.99 (3H, s), 3.60 (3H, s), 2.19 (3H, s), 2.18-2.06 (1H, m), 1.02-0.96 (2H, m), 0.79-0.73 (2H, m).

Present Compound 7

¹H-NMR (CDCl3) δ: 7.44-7.39 (2H, m), 7.27-7.25 (1H, m), 7.18 (1H, d, J=0.7 Hz), 7.10-7.06 (2H, m), 5.07 (2H, s), 4.00 (3H, s), 3.64 (3H, s), 2.51 (3H, s), 2.20 (3H, s), 2.08 (3H, s).

Present Compound 8

¹H-NMR (CDCl3) δ: 7.46 (1H, t, J=8.2 Hz), 7.20 (1H, s), 7.09-7.03 (4H, m), 5.31 (2H, s), 3.99 (3H, s), 3.94 (3H, s), 3.61 (3H, s), 2.18 (3H, s), 1.99 (3H, s).

Present Compound 9

¹H-NMR (CDCl3) δ: 7.43 (1H, t, J=7.9 Hz), 7.28-7.21 (3H, m), 7.11-7.06 (2H, m), 5.30 (2H, s), 4.00 (3H, s), 3.63 (3H, s), 2.21 (3H, s), 2.18-2.12 (1H, m), 2.08 (3H, s), 1.03-0.96 (2H, m), 0.80-0.75 (2H, m).

Present Compound 26

¹H-NMR (CDCl3) δ: 7.45-7.39 (2H, m), 7.30-7.19 (3H, m), 7.18-7.16 (1H, m), 6.89-6.86 (1H, m), 5.04 (2H, s), 3.98 (3H, s), 3.63 (3H, s), 2.71 (2H, q, J=7.6 Hz), 2.50 (3H, s), 1.11 (3H, t, J=7.6 Hz).

Present Compound 27

¹H-NMR (CDCl3) δ: 7.46 (1H, t, J=8.2 Hz), 7.22 (1H, t, J=7.8 Hz), 7.20-7.16 (1H, m), 7.12-7.05 (3H, m), 6.84-6.80 (1H, m), 5.24 (2H, s), 3.97 (3H, s), 3.92 (3H, s), 3.59 (3H, s), 2.69 (2H, q, J=7.6 Hz), 1.10 (3H, t, J=7.6 Hz).

Present Compound 28

¹H-NMR (CDCl3) δ: 7.42 (1H, t, J=7.9 Hz), 7.29-7.16 (5H, m), 6.89-6.86 (1H, m), 5.26 (2H, s), 3.96 (3H, s), 3.60 (3H, s), 2.68 (2H, t, J=7.8 Hz), 2.16-2.06 (1H, m), 1.53-1.42 (2H, m), 1.40-1.33 (2H, m), 1.02-0.95 (2H, m), 0.90 (3H, t, J=7.2 Hz), 0.80-0.72 (2H, m).

Present Compound 29

¹H-NMR (CDCl3) δ: 7.44 (1H, t, J=7.9 Hz), 7.25 (4H, dt, J=19.8, 5.7 Hz), 7.20-7.17 (1H, m), 6.91-6.89 (1H, m), 5.28 (2H, s), 3.99 (3H, s), 3.62 (3H, s), 2.72 (2H, q, J=7.6 Hz), 2.20-2.05 (1H, m), 1.13 (3H, t, J=7.6 Hz), 1.03-0.98 (2H, m), 0.80-0.76 (2H, m).

Present Compound 31

¹H-NMR (CDCl3) δ: 7.48 (1H, t, J=8.2 Hz), 7.23 (1H, t, J=7.8 Hz), 7.18 (1H, d, J=7.8 Hz), 7.11-7.07 (3H, m), 6.86-6.81 (1H, m), 5.25 (2H, s), 3.97 (3H, s), 3.93 (3H, s), 3.61 (3H, s), 2.69 (2H, t, J=7.8 Hz), 1.53-1.43 (2H, m), 1.39-1.33 (2H, m), 0.91 (3H, t, J=7.2 Hz).

Present Compound 44

¹H-NMR (CDCl3) δ: 7.53 (1H, t, J=7.6 Hz), 7.46 (1H, d, J=7.2 Hz), 7.42-7.37 (2H, m), 7.26-7.22 (1H, m), 6.62 (1H, d, J=8.0 Hz), 5.42 (2H, s), 4.01 (3H, s), 3.61 (3H, s), 2.51 (3H, s), 2.25 (3H, s).

Present Compound 47

¹H-NMR (CDCl3) δ: 7.59 (1H, d, J=8.0 Hz), 7.46 (1H, t, J=8.0 Hz), 7.39 (1H, d, J=8.0 Hz), 7.34 (2H, t, J=7.7 Hz), 7.18 (1H, t, J=8.2 Hz), 7.12 (1H, td, J=7.4, 0.8 Hz), 7.01 (2H, dd, J=7.7, 0.8 Hz), 6.60-6.54 (2H, m), 6.49-6.46 (1H, m), 5.27 (2H, s), 3.60 (3H, s).

Production Example 2

To a mixture of 0.15 g of phenol and 5 mL of N,N-dimethylformamide, 0.065 g of sodium hydride was added at 0° C. under ice cooling, followed by stirring for 30 minutes and further the addition of 0.51 g of 1-{2-[(6-bromopyridin-2-yloxy)methyl]-3-methylphenyl}-4-methyl-1,4-dihydrotetrazol-5-one mentioned in Reference Production Example 34. After returning to room temperature, 0.067 g of copper chloride was added, followed by stirring with heating at 120° C. under reflux for 8 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.32 g of 4-methyl-1-(3-methyl-2-{[(6-phenoxypyridin-2-yl)oxy]methyl}phenyl)-1,4-dihydrotetrazol-5-one (hereinafter referred to as the present compound 34).

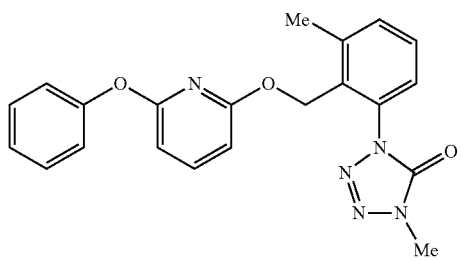 [SMILES: Cc1cccc(-n2nnn(C)c2=O)c1COc1cccc(Oc2ccccc2)n1]

$^1$H-NMR (CDCl3) δ: 7.49 (1H, t, J=7.8 Hz), 7.41-7.30 (4H, m), 7.25-7.17 (2H, m), 7.12 (2H, d, J=7.5 Hz), 6.35 (1H, d, J=8.0 Hz), 6.26 (1H, d, J=7.7 Hz), 5.27 (2H, s), 3.64 (3H, s), 2.40 (3H, s).

In accordance with the reaction of Production Example 2, the present compounds 35 and 36 were synthesized using commercially available compounds.

The structural formulas and $^1$H-NMR data thereof are shown below.

Present Compound 35

$^1$H-NMR (CDCl3) δ: 7.53 (1H, t, J=8.0 Hz), 7.40-7.30 (2H, m), 7.23-7.13 (5H, m), 6.40 (1H, d, J=7.7 Hz), 6.35 (1H, d, J=8.0 Hz), 5.11 (2H, s), 3.65 (3H, s), 2.34 (3H, s).

Present Compound 36

$^1$H-NMR (CDCl3) δ: 7.61 (1H, t, J=7.7 Hz), 7.56 (1H, t, J=7.8 Hz), 7.39-7.30 (2H, m), 7.25-7.20 (1H, m), 6.98 (1H, d, J=7.2 Hz), 6.79 (1H, d, J=8.0 Hz), 6.52 (1H, d, J=7.7 Hz), 6.42 (1H, d, J=8.0 Hz), 5.19 (2H, s), 3.65 (3H, s), 2.50 (3H, s), 2.38 (3H, s).

Production Example 3

A mixture of 0.34 g of 1-{2-[(3-acetylphenoxy)methyl]-3-methylphenyl}-4-methyl-1,4-dihydrotetrazol-5-one mentioned in Reference Production Example 17, 0.15 g of 0-phenylhydroxylamine hydrochloride, 0.05 mL of 35% hydrochloric acid, and 4 mL of ethanol was stirred at room temperature for 2 hours. To the reaction solution, an aqueous saturated sodium hydrogen carbonate solution was added and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.25 g of 1-[2-({3-[1-(phenoxyimino)ethyl]phenoxy}methyl)-3-methylphenyl]-4-methyl-1,4-dihydrotetrazol-5-one (hereinafter referred to as the present compound 10).

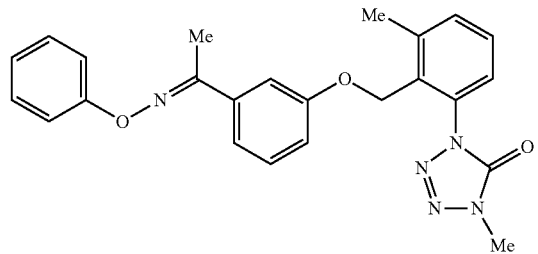 [SMILES: CC(=NOc1ccccc1)c1cccc(OCc2c(C)cccc2-n2nnn(C)c2=O)c1]

$^1$H-NMR (CDCl$_3$) δ: 7.45-7.40 (2H, m), 7.38-7.28 (8H, m), 7.08-7.01 (1H, m), 6.96-6.92 (1H, m), 5.09 (2H, s), 3.62 (3H, s), 2.52 (3H, s), 2.43 (3H, s).

In accordance with Production Example 3, the present compounds 11 to 16, 19 to 25, and 30 were synthesized.

The structural formulas and $^1$H-NMR data thereof are shown below.

Present Compound 35

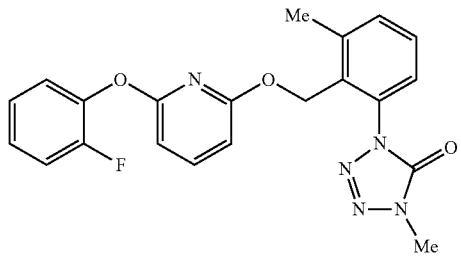

Present Compound 36

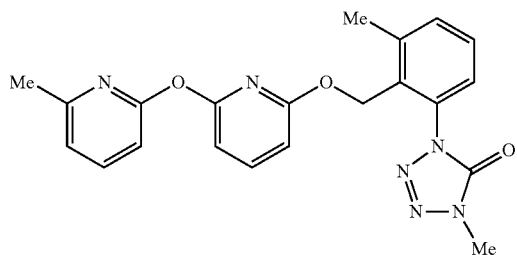

Present Compound 11

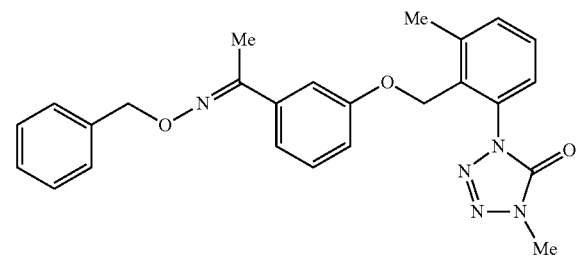

Present Compound 12
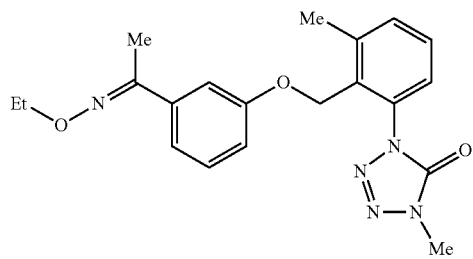
Present Compound 13
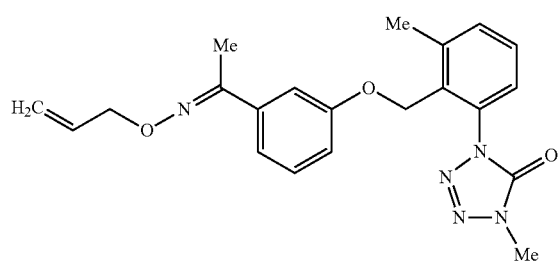
Present Compound 14
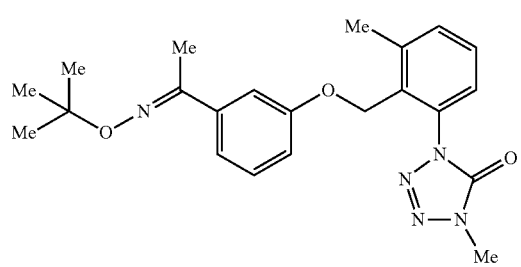
Present Compound 15
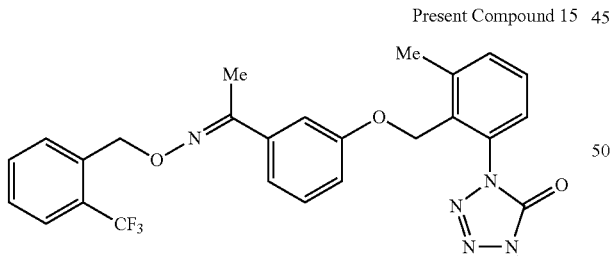
Present Compound 16
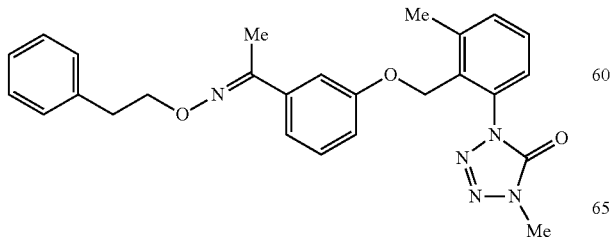
Present Compound 19
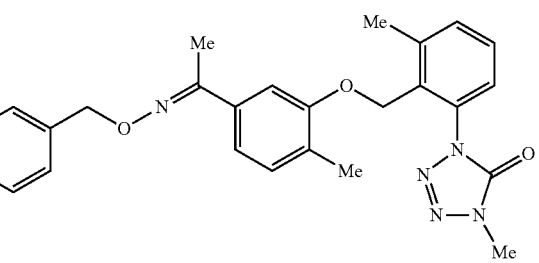
Present Compound 20
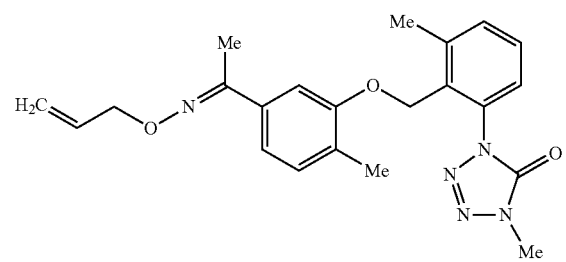
Present Compound 21
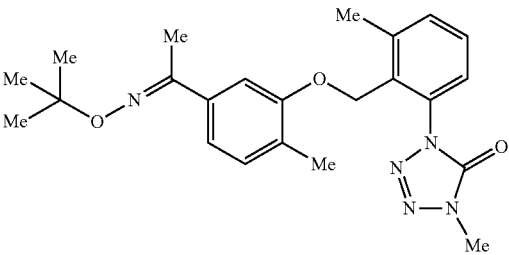
Present Compound 22
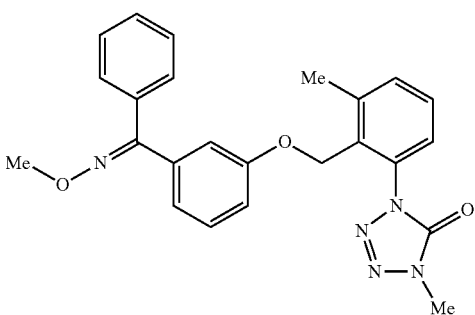
Present Compound 23

Present Compound 24

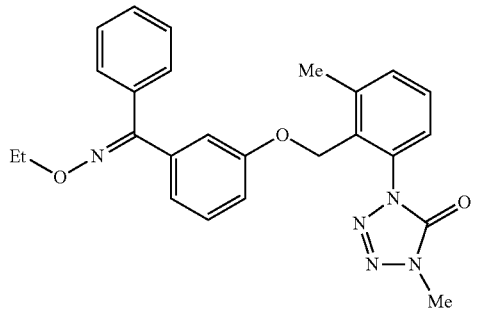

Present Compound 25

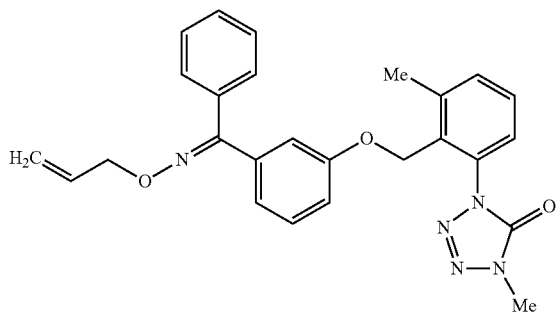

Present Compound 30

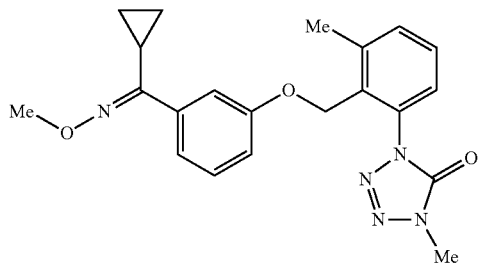

Present Compound 11
¹H-NMR (CDCl₃) δ: 7.43-7.21 (10H, m), 7.17 (1H, d, J=1.6 Hz), 6.88-6.86 (1H, m), 5.24 (2H, s), 5.04 (2H, s), 3.60 (3H, s), 2.49 (3H, s), 2.24 (3H, s).
Present Compound 12
¹H-NMR (CDCl₃) δ: 7.45-7.38 (2H, m), 7.29-7.18 (4H, m), 6.86 (1H, dt, J=7.6, 2.1 Hz), 5.04 (2H, s), 4.24 (2H, q, J=7.0 Hz), 3.62 (3H, s), 2.50 (3H, s), 2.20 (3H, s), 1.33 (3H, t, J=7.0 Hz).
Present Compound 13
¹H-NMR (CDCl₃) δ: 7.44-7.37 (2H, m), 7.28-7.19 (3H, m), 7.19-7.14 (1H, m), 6.88-6.84 (1H, m), 6.13-5.98 (1H, m), 5.38-5.29 (1H, m), 5.27-5.19 (1H, m), 5.04 (2H, s), 4.71-4.68 (2H, m), 3.62 (3H, s), 2.50 (3H, s), 2.23 (3H, s).
Present Compound 14
¹H-NMR (CDCl₃) δ: 7.44-7.38 (2H, m), 7.30-7.19 (4H, m), 6.87-6.82 (1H, m), 5.05 (2H, s), 3.61 (3H, s), 2.50 (3H, s), 2.17 (3H, s), 1.35 (9H, s).
Present Compound 15
¹H-NMR (CDCl₃) δ: 7.68 (1H, s), 7.64-7.56 (2H, m), 7.54-7.38 (3H, m), 7.30-7.22 (3H, m), 7.19-7.16 (1H, m), 6.89 (1H, d, J=7.7 Hz), 5.29 (2H, s), 5.05 (2H, s), 3.61 (3H, s), 2.50 (3H, s), 2.27 (3H, s).
Present Compound 16
¹H-NMR (CDCl₃) δ: 7.45-7.38 (2H, m), 7.31-7.16 (6H, m), 6.98-6.93 (3H, m), 6.90-6.86 (1H, m), 5.04 (2H, s), 4.54 (2H, t, J=4.8 Hz), 4.28 (2H, t, J=4.8 Hz), 3.61 (3H, s), 2.50 (3H, s), 2.21 (3H, s).
Present Compound 19
¹H-NMR (CDCl₃) δ: 7.44-7.39 (2H, m), 7.29-7.25 (1H, m), 7.18 (1H, s), 7.08 (2H, s), 5.08 (2H, s), 4.25 (2H, q, J=7.1 Hz), 3.64 (3H, s), 2.51 (3H, s), 2.21 (3H, s), 2.08 (3H, s), 1.34 (3H, t, J=7.1 Hz).
Present Compound 20
¹H-NMR (CDCl₃) δ: 7.45-7.25 (8H, m), 7.18 (1H, s), 7.09 (2H, s), 5.25 (2H, s), 5.07 (2H, s), 3.62 (3H, s), 2.50 (3H, s), 2.24 (3H, s), 2.08 (3H, s).
Present Compound 21
¹H-NMR (CDCl₃) δ: 7.44-7.39 (2H, m), 7.29-7.25 (1H, m), 7.17 (1H, s), 7.08 (2H, s), 6.16-6.02 (1H, m), 5.41-5.31 (1H, m), 5.29-5.21 (1H, m), 5.07 (2H, s), 4.72 (2H, d, J=5.7 Hz), 3.63 (3H, s), 2.51 (3H, s), 2.23 (3H, s), 2.08 (3H, s).
Present Compound 22
¹H-NMR (CDCl₃) δ: 7.44-7.39 (2H, m), 7.29-7.25 (1H, m), 7.22-7.20 (1H, m), 7.14-7.06 (2H, m), 5.09 (2H, s), 3.63 (3H, s), 2.53 (3H, s), 2.18 (3H, s), 2.07 (3H, s), 1.36 (9H, s).
Present Compound 23
¹H-NMR (CDCl₃) δ: 7.48-7.25 (8H, m), 7.20 (0.5H, t, J=8.0 Hz), 7.10-7.08 (0.5H, m), 7.00-6.96 (1H, m), 6.95-6.83 (2H, m), 5.03-5.01 (2H, m), 3.99-3.96 (3H, m), 3.63 (1.5H, s), 3.61 (1.5H, s), 2.48 (1.5H, s), 2.47 (1.5H, s).
Present Compound 24
¹H-NMR (CDCl₃) δ: 7.49-7.45 (1H, m), 7.44-7.24 (7.5H, m), 7.20 (0.5H, t, J=7.9 Hz), 7.09-7.07 (0.5H, m), 7.00-6.84 (2.5H, m), 5.02-5.00 (2H, m), 4.27-4.20 (2H, m), 3.63 (1.5H, s), 3.60 (1.5H, s), 2.48 (1.5H, s), 2.47 (1.5H, s), 1.33-1.27 (3H, m).
Present Compound 25
¹H-NMR (CDCl₃) δ: 7.48-7.25 (9H, m), 7.20 (0.5H, t, J=7.9 Hz), 7.09-7.06 (0.5H, m), 7.01-6.84 (2H, m), 6.07-5.98 (1H, m), 5.30-5.24 (1H, m), 5.23-5.17 (1H, m), 5.03-5.00 (2H, m), 4.71-4.67 (2H, m), 3.63 (1.5H, s), 3.60 (1.5H, s), 2.48 (1.5H, s), 2.46 (1.5H, s).
Present Compound 30
¹H-NMR (CDCl₃) δ: 7.45-7.38 (2H, m), 7.31-7.20 (2H, m), 7.01-6.95 (1H, m), 6.90-6.84 (2H, m), 5.03 (1H, s), 5.01 (1H, s), 3.98 (1.5H, s), 3.79 (1.5H, s), 3.64 (1.5H, s), 3.62 (1.5H, s), 2.50 (1.5H, s), 2.49 (1.5H, s), 2.28-2.19 (1H, m), 0.93-0.86 (1.5H, m), 0.81-0.76 (1.3H, m), 0.63-0.57 (1.2H, m).

Production Example 4

A mixture of 0.30 g of 1-[2-{3-[1-(hydroxyimino)ethyl]phenoxy}methyl}-3-methylphenyl]-4-methyl-1,4-dihydrotetrazol-5-one mentioned in Reference Production Example 19, 0.12 g of 2-bromopropane, 0.24 g of potassium carbonate, and 3 mL of acetonitrile was stirred with heating under reflux for 4 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.06 g of 1-[2-({3-[1-(1-methylpropoxyimino)ethyl]phenoxy}methyl]-3-methylphenyl]-4-methyl-1,4-dihydrotetrazol-5-one (hereinafter referred to as the present compound 17).

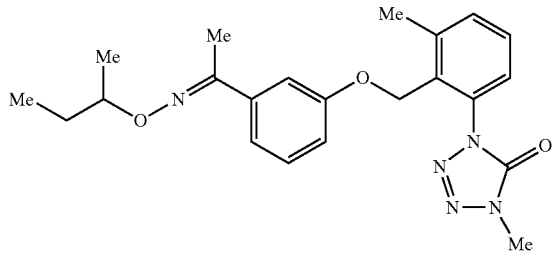 [SMILES: CCC(C)ON=C(C)c1cccc(OCc2c(C)cccc2-n2nnn(C)c2=O)c1]

¹H-NMR (CDCl₃) δ: 7.43-7.38 (2H, m), 7.30-7.21 (3H, m), 7.20-7.16 (1H, m), 6.86-6.83 (1H, m), 5.04 (2H, s), 4.29-4.20 (1H, m), 3.62 (3H, s), 2.50 (3H, s), 2.19 (3H, s), 1.81-1.51 (2H, m), 1.28 (3H, d, J=6.3 Hz), 0.95 (3H, t, J=7.4 Hz).

In accordance with the reaction of Production Example 4, the present compounds 18 and 32 were synthesized using commercially available compounds.

The structural formulas and ¹H-NMR data thereof are shown below.

Present Compound 18

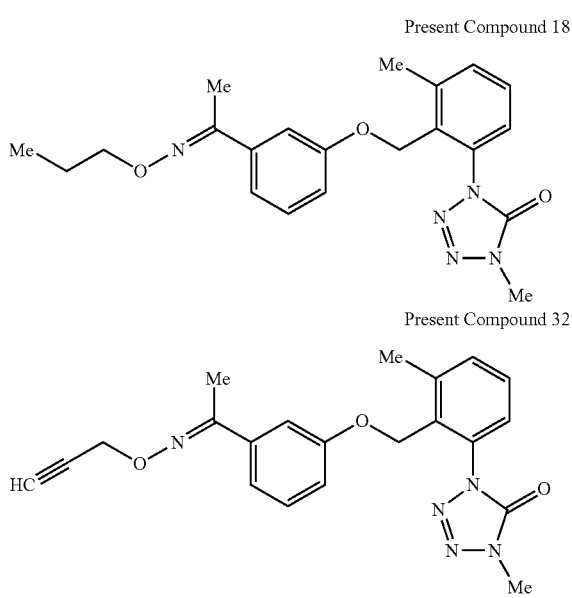 [SMILES: CCCON=C(C)c1cccc(OCc2c(C)cccc2-n2nnn(C)c2=O)c1 ; C#CCON=C(C)c1cccc(OCc2c(C)cccc2-n2nnn(C)c2=O)c1]

Present Compound 32

Present Compound 18
¹H-NMR (CDCl₃) δ: 7.45-7.37 (2H, m), 7.30-7.20 (3H, m), 7.19-7.16 (1H, m), 6.88-6.84 (1H, m), 5.04 (2H, s), 4.15 (2H, t, J=6.6 Hz), 3.62 (3H, s), 2.50 (3H, s), 2.20 (3H, s), 1.79-1.69 (2H, m), 0.98 (3H, t, J=7.4 Hz).
Present Compound 32
¹H-NMR (CDCl3) δ: 7.45-7.39 (2H, m), 7.29-7.26 (1H, m), 7.23-7.06 (4H, m), 5.09 (2H, s), 4.85 (2H, s), 3.64 (3H, s), 2.52 (3H, s), 2.23 (3H, s), 2.11-2.08 (1H, m).

Production Example 5

A mixture of 0.38 g of 1-{2-[(3-bromophenoxy)methyl]-3-methylphenyl}-4-methyl-1,4-dihydrotetrazol-5-one mentioned in Reference Production Example 27, 0.11 g of N-methylaniline, 0.29 g of tert-butoxysodium, 0.12 g of 2-(di-tert-butylphosphino)biphenyl, 0.18 g of a palladium dibenzylidineacetone complex and 4 mL of toluene was stirred with heating under reflux for 4 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.20 g of 1-(2-{[3-(N-methylanilino)phenoxy]methyl}-3-methylphenyl)-4-methyl-1,4-dihydrotetrazol-5-one (hereinafter referred to as the present compound 33).

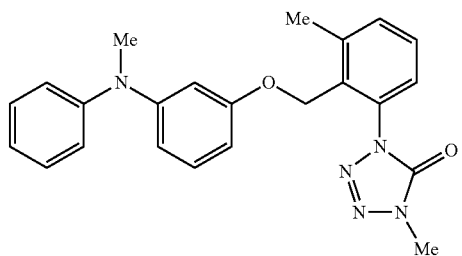 [SMILES: Cc1cccc(-n2nnn(C)c2=O)c1COc1cccc(N(C)c2ccccc2)c1]

¹H-NMR (CDCl₃) δ: 7.45-7.36 (2H, m), 7.31-7.25 (3H, m), 7.12 (1H, t, J=8.1 Hz), 7.09-7.05 (2H, m), 7.01 (1H, t, J=7.3 Hz), 6.59-6.54 (1H, m), 6.49-6.46 (1H, m), 6.46-6.42 (1H, m), 4.98 (2H, s), 3.63 (3H, s), 3.28 (3H, s), 2.47 (3H, s).

Production Example 6

A mixture of 0.30 g of 1-{2-[(3-hydroxyphenoxy)methyl]-3-methylphenyl}-4-methyl-1,4-dihydrotetrazol-5-one mentioned in Reference Production Example 22, 0.17 g of benzyl bromide, 0.16 g of potassium carbonate, and 7 mL of acetonitrile was stirred with heating under reflux for 3 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.20 g of 1-{2-[(3-benzyloxyphenoxy)methyl]-3-methylphenyl}-4-methyl-1,4-dihydrotetrazol-5-one (hereinafter referred to as the present compound 37).

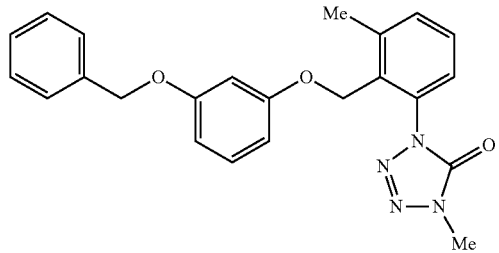 [SMILES: Cc1cccc(-n2nnn(C)c2=O)c1COc1cccc(OCc2ccccc2)c1]

¹H-NMR (CDCl₃) δ: 7.46-7.36 (6H, m), 7.35-7.27 (2H, m), 7.17 (1H, t, J=8.2 Hz), 6.61-6.58 (1H, m), 6.54-6.48 (2H, m), 5.02 (2H, s), 5.00 (2H, s), 3.62 (3H, s), 2.49 (3H, s).

In accordance with Production Example 6, the present compounds 38 to 44 were synthesized.

The structural formulas and $^1$H-NMR data thereof are shown below.

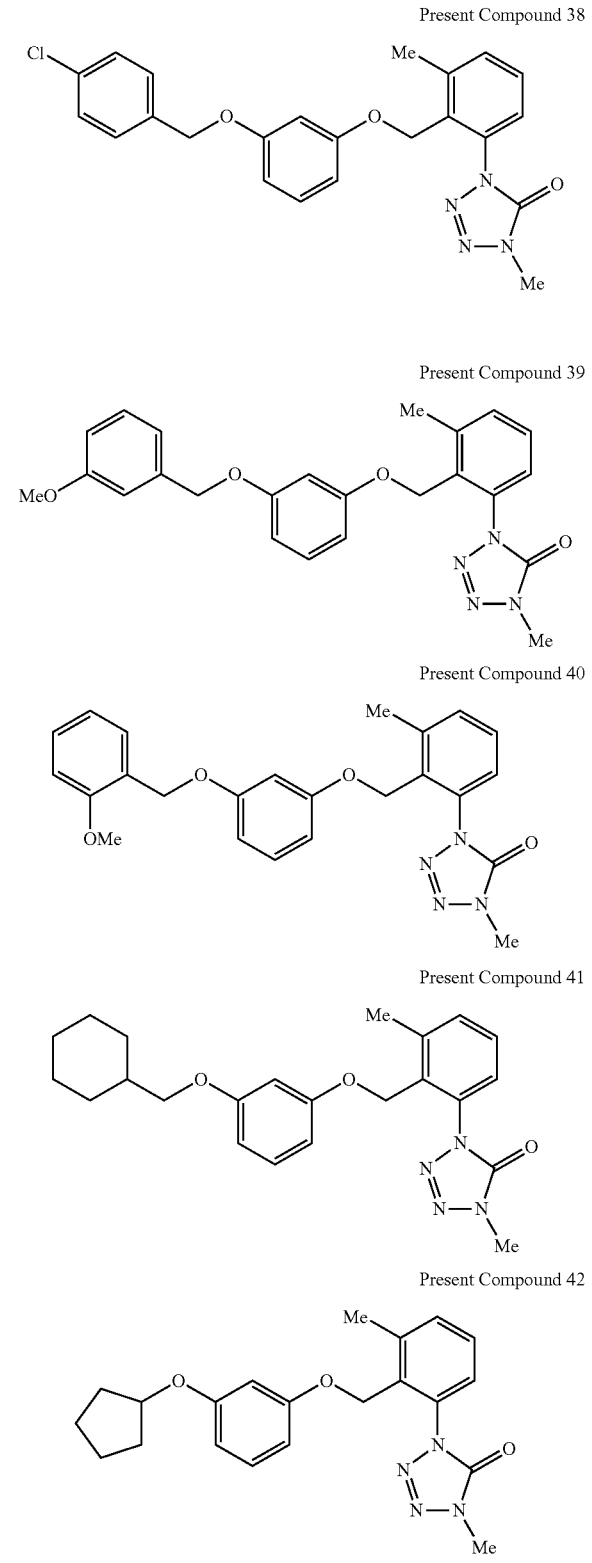

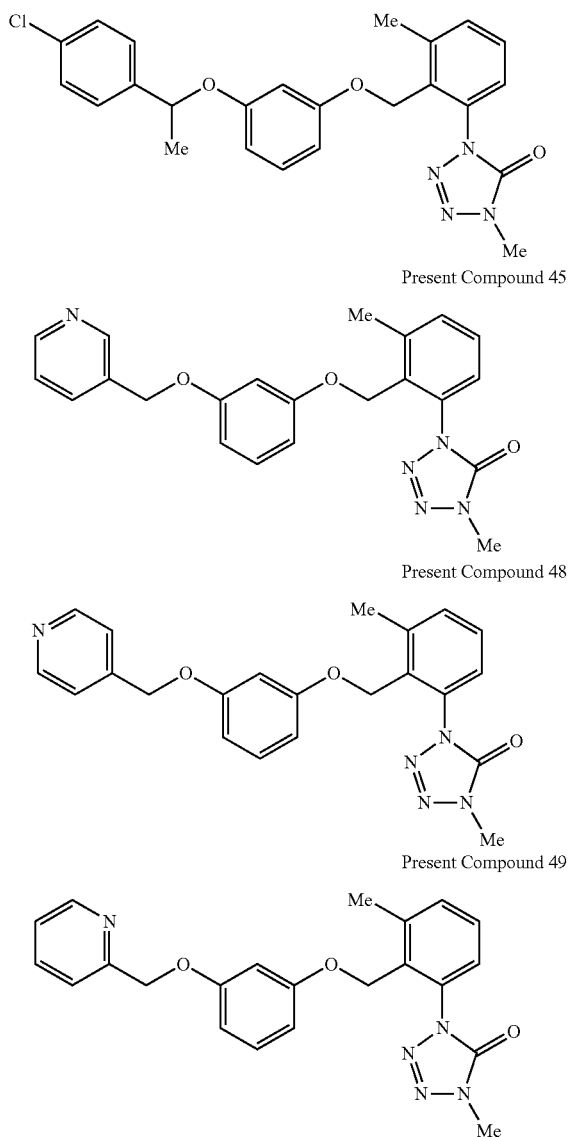

Present Compound 38
$^1$H-NMR (CDCl$_3$) δ: 7.45-7.37 (2H, m), 7.37-7.35 (4H, m), 7.30-7.27 (1H, m), 7.17 (1H, t, J=8.5 Hz), 6.58-6.50 (3H, m), 4.99 (2H, s), 4.99 (2H, s), 3.62 (3H, s), 2.48 (3H, s).

Present Compound 39
$^1$H-NMR (CDCl$_3$) δ: 7.44-7.39 (2H, m), 7.33-7.26 (2H, m), 7.17 (1H, t, J=8.1 Hz), 7.02-6.98 (2H, m), 6.87 (1H, dd, J=8.1, 2.5 Hz), 6.61-6.58 (1H, m), 6.53-6.49 (2H, m), 5.00 (2H, s), 5.00 (2H, s), 3.83 (3H, s), 3.62 (3H, s), 2.49 (3H, s).

Present Compound 40
$^1$H-NMR (CDCl$_3$) δ: 7.46-7.40 (3H, m), 7.32-7.26 (2H, m), 7.16 (1H, t, J=8.2 Hz), 7.01-6.95 (1H, m), 6.91 (1H, d, J=8.2 Hz), 6.64-6.60 (1H, m), 6.56 (1H, t, J=2.4 Hz), 6.51-6.47 (1H, m), 5.07 (2H, s), 4.99 (2H, s), 3.86 (3H, s), 3.61 (3H, s), 2.49 (3H, s).

Present Compound 41
$^1$H-NMR (CDCl$_3$) δ: 7.45-7.37 (2H, m), 7.29-7.26 (1H, m), 7.14 (1H, t, J=8.1 Hz), 6.52-6.42 (3H, m), 4.99 (2H, s), 3.71 (2H, d, J=6.4 Hz), 3.62 (3H, s), 2.49 (3H, s), 1.87-1.74 (6H, m), 1.35-1.15 (3H, m), 1.10-0.97 (2H, m).

Present Compound 42

¹H-NMR (CDCl₃) δ: 7.44-7.38 (2H, m), 7.30-7.25 (1H, m), 7.14 (1H, t, J=8.1 Hz), 6.50-6.41 (3H, m), 4.99 (2H, s), 4.74-4.68 (1H, m), 3.62 (3H, s), 2.49 (3H, s), 1.88-1.76 (6H, m), 1.62-1.59 (2H, m).

Present Compound 43

¹H-NMR (CDCl₃) δ: 7.44-7.30 (6H, m), 7.29-7.22 (1H, m), 7.06 (1H, t, J=8.1 Hz), 6.49-6.39 (3H, m), 5.28 (1H, q, J=6.6 Hz), 4.94 (2H, s), 3.58 (3H, s), 2.44 (3H, s), 1.62 (3H, d, J=6.6 Hz).

Present Compound 45

¹H-NMR (CDCl₃) δ: 8.68 (1H, s), 8.62-8.57 (1H, m), 7.81-7.75 (1H, m), 7.44-7.39 (2H, m), 7.36-7.31 (1H, m), 7.30-7.26 (1H, m), 7.19 (1H, t, J=8.4 Hz), 6.59 (1H, dd, J=8.9, 1.8 Hz), 6.55-6.50 (2H, m), 5.04 (2H, s), 5.01 (2H, s), 3.62 (3H, s), 2.49 (3H, s).

Present Compound 48

¹H-NMR (CDCl₃) δ: 8.62 (2H, d, J=5.7 Hz), 7.45-7.38 (2H, m), 7.37-7.33 (2H, m), 7.30-7.26 (1H, m), 7.18 (1H, t, J=8.2 Hz), 6.58-6.49 (3H, m), 5.05 (2H, s), 5.01 (2H, s), 3.62 (3H, s), 2.48 (3H, s).

Present Compound 49

¹H-NMR (CDCl₃) δ: 8.63-8.58 (1H, m), 7.72 (1H, t, J=7.7 Hz), 7.52 (1H, d, J=7.8 Hz), 7.44-7.37 (2H, m), 7.30-7.21 (2H, m), 7.17 (1H, t, J=8.1 Hz), 6.63-6.57 (1H, m), 6.57-6.54 (1H, m), 6.53-6.48 (1H, m), 5.17 (2H, s), 5.00 (2H, s), 3.63 (3H, s), 2.48 (3H, s).

Production Example 7

A mixture of 0.33 g of 1-[2-{[3-(hydroxymethyl)phenoxy]methyl}-3-methylphenyl]-4-methyl-1,4-dihydrotetrazol-5-one mentioned in Reference Production Example 39, 0.16 g of 2-bromopyridine, 0.34 g of potassium tert-butoxide, and 4 mL of tetrahydrofuran was stirred with heating under reflux for 4 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.04 g of 1-[2-({3-[(2-pyridyloxy)methyl]phenoxy}methyl)-3-methylphenyl]-4-methyl-1,4-dihydrotetrazol-5-one (hereinafter referred to as the present compound 46).

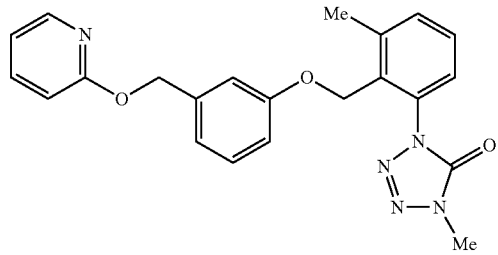 [SMILES: Cc1cccc(-n2nnn(C)c2=O)c1COc1cccc(COc2ccccn2)c1]

¹H-NMR (CDCl₃) δ: 8.21-8.17 (1H, m), 7.63-7.58 (1H, m), 7.45-7.41 (2H, m), 7.31-7.26 (1H, m), 7.07-6.82 (6H, m), 5.35 (2H, s), 5.04 (2H, s), 3.63 (3H, s), 2.50 (3H, s).

With respect to the production of intermediates for the production of the above-mentioned present compounds, Reference Production Examples are shown below.

Reference Production Example 1

Under ice cooling, 21.9 g of anhydrous aluminum chloride was added to 250 mL of N,N-dimethylformamide, followed by stirring for 15 minutes. To this was added 10.7 g of sodium azide and, after stirring for 15 minutes, 25.0 g of 1-chloro-3-isocyanato-2-methylbenzene was added, followed by heating at 80° C. for 5 hours. After cooling, the reaction solution was added in a mixture of 35 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 17.0 g of 1-(2-methyl-3-chlorophenyl)-1,4-dihydrotetrazol-5-one.

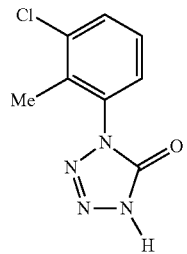

¹H-NMR (CDCl₃) δ(ppm): 2.32 (3H, s), 7.28-7.36 (2H, m), 7.57 (1H, dd, J=6.8, 2.2 Hz), 13.08 (1H, s).

Reference Production Example 2

To a mixture of 10.00 g of 1-(2-methyl-3-chlorophenyl)-1,4-dihydrotetrazol-5-one mentioned in Reference Production Example 1 and 100 mL of N,N-dimethylformamide, under ice cooling, 2.30 g of 60% sodium hydride was added. The temperature of the mixture was raised to room temperature, followed by stirring for 1 hour. To the reaction mixture, 3.2 mL of methyl iodide was added under ice cooling. The temperature of the mixture was raised to room temperature, followed by stirring for 14 hours. To the reaction mixture, water was added and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 1.56 g of 1-(2-methyl-3-chlorophenyl)-4-methyl-1,4-dihydrotetrazol-5-one.

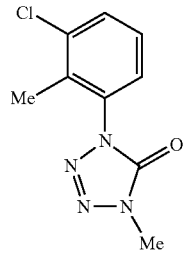

¹H-NMR (CDCl₃) δ(ppm): 2.30 (3H, s), 3.73 (3H, s), 7.27 (1H, d, J=2.7 Hz), 7.28 (1H, d, J=7.1 Hz), 7.52 (1H, dd, J=2.7, 6.8 Hz).

Reference Production Example 3

A mixture of 1.56 g of 1-(2-methyl-3-chlorophenyl)-4-methyl-1,4-dihydrotetrazol-5-one mentioned in Reference Production Example 2, 0.34 g of 1,1'-azobis(cyclohexane-1-carbonitrile), 1.42 g of N-bromosuccinimide, and 30 mL of chlorobenzene was stirred with heating under reflux for 5 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.94 g of 1-[2-(bromomethyl)-3-chlorophenyl]-4-methyl-1,4-dihydrotetrazol-5-one.

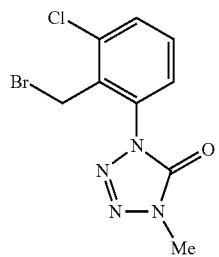

$^1$H-NMR (CDCl$_3$) δ(ppm): 3.76 (3H, s), 4.69 (2H, s), 7.35 (1H, dd, J=1.2, 8.1 Hz), 7.43 (1H, t, J=8.1 Hz), 7.58 (1H, dd, J=1.2, 8.1 Hz).

Reference Production Example 4

A mixture of 15.0 g of 3-amino-1-methoxy-2-methylbenzene, 48.7 g of triphosgene, and 350 ml of toluene was stirred with heating under reflux for 3 hours. The reaction mixture allowed to cool was concentrated under reduced pressure to obtain 17.0 g of 1-methoxy-3-isocyanato-2-methylbenzene.

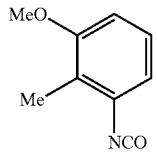

$^1$H-NMR (CDCl$_3$) δ(ppm): 2.19 (3H, s), 3.82 (3H, s), 6.69 (1H, d, J=8.2 Hz), 6.72 (1H, dd, J=0.5, 8.0 Hz), 7.09 (1H, t, J=8.2 Hz).

Reference Production Example 5

Under ice cooling, 16.0 g of anhydrous aluminum chloride was added to 180 mL of N,N-dimethylformamide, followed by stirring for 15 minutes. To this was added 7.8 g of sodium azide and, after stirring for 15 minutes, 17.0 g of 1-methoxy-3-isocyanato-2-methylbenzene mentioned in Reference Production Example 4 was added, followed by heating at 80° C. for 4.5 hours. After cooling, the reaction solution was added in a mixture of 25 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 16.2 g of 1-(2-methyl-3-methoxyphenyl)-1,4-dihydrotetrazol-5-one.

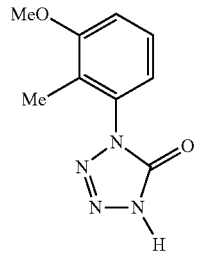

$^1$H-NMR (DMSO-d$_6$) δ(ppm): 1.99 (3H, s), 3.87 (3H, s), 7.01 (1H, d, J=8.1 Hz), 7.17 (1H, d, J=8.1 Hz). 7.36 (1H, t, J=8.3 Hz), 14.63 (1H, s).

Reference Production Example 6

To a mixture of 10.00 g of 1-(2-methyl-3-methoxyphenyl)-1,4-dihydrotetrazol-5-one mentioned in Reference Production Example 5 and 100 mL of N,N-dimethylformamide, 2.47 g of 60% sodium hydride was added under ice cooling. The temperature of the mixture was raised to room temperature, followed by stirring for 1 hour. To the reaction mixture, 3.5 mL of methyl iodide was added under ice cooling. The temperature of the mixture was raised to room temperature, followed by stirring for 14 hours. To the reaction mixture, water was added and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 2.19 g of 1-(2-methyl-3-methoxyphenyl)-4-methyl-1,4-dihydrotetrazol-5-one.

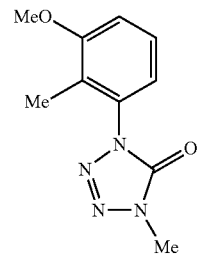

$^1$H-NMR (CDCl$_3$) δ(ppm): 2.11 (3H, s), 3.72 (3H, s), 3.88 (3H, s), 6.95 (1H, d, J=8.2 Hz), 6.98 (1H, d, J=8.5 Hz), 7.29 (1H, t, J=8.2 Hz)

Reference Production Example 7

A mixture of 2.19 g of 1-(2-methyl-3-methoxyphenyl)-4-methyl-1,4-dihydrotetrazol-5-one mentioned in Reference Production Example 6, 0.52 g of 1,1'-azobis(cyclohexane-1-carbonitrile), 2.16 g of N-bromosuccinimide, and 40 mL of chlorobenzene was stirred with heating under reflux for 5 hours. After cooling, water was added to the reaction solution and the mixture was extracted with ethyl acetate. The organic layer was washed with water and a saturated saline solution, dried over anhydrous magnesium sulfate, and then concentrated under reduced pressure.

The residue thus obtained was subjected to silica gel column chromatography to obtain 2.36 g of 1-[2-(bromomethyl)-3-methoxyphenyl]-4-methyl-1,4-dihydrotetrazol-5-one.

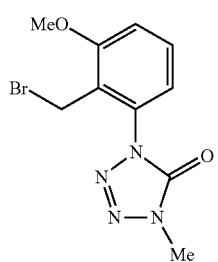

¹H-NMR (CDCl₃) δ(ppm): 3.74 (3H, s), 3.96 (3H, s), 4.93 (2H, s), 7.02 (1H, dd, J=1.0, 8.5 Hz), 7.04 (1H, d, J=9.0 Hz), 7.43 (1H, t, J=8.1 Hz).

Reference Production Example 8

A mixture of 25.0 g of 1-bromo-2-methyl-3-aminobenzene, 60.0 g of triphosgene, and 400 ml of toluene was stirred with heating under reflux for 3 hours. The reaction mixture allowed to cool was concentrated under reduced pressure to obtain 30.3 g of 1-bromo-3-isocyanato-2-methylbenzene.

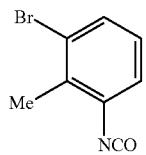

¹H-NMR (CDCl₃) δ(ppm): 2.42 (3H, s), 7.00 (1H, dt, J=0.5, 8.0 Hz), 7.05 (1H, dd, J=1.7, 8.0 Hz), 7.39 (1H, dd, 1.5, 7.7 Hz).

Reference Production Example 9

Under ice cooling, 19.7 g of anhydrous aluminum chloride was added to 220 mL of N,N-dimethylformamide, followed by stirring for 15 minutes. To this was added 9.6 g of sodium azide and, after stirring for 15 minutes, 30.3 g of 1-bromo-3-isocyanato-2-methylbenzene mentioned in Reference Production Example 8 was added, followed by heating at 80° C. for 5 hours. After cooling, the reaction solution was added in a mixture of 33 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 31.4 g of 1-(2-methyl-3-bromophenyl)-1,4-dihydrotetrazol-5-one.

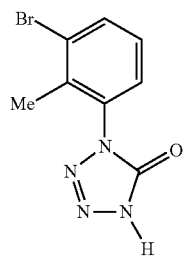

¹H-NMR (DMSO-d₆) δ(ppm): 2.22 (3H, s), 7.34 (1H, t, J=7.2 Hz), 7.49 (1H, dd, J=8.2, 1.1 Hz), 7.82 (1H, dd, J=8.0, 1.0 Hz), 14.72 (1H, s).

Reference Production Example 10

To a mixture of 31.4 g of 1-(2-methyl-3-bromophenyl)-1,4-dihydrotetrazol-5-one mentioned in Reference Production Example 9 and 250 mL of N,N-dimethylformamide, 5.90 g of 60% sodium hydride was added under ice cooling. The temperature of the mixture was raised to room temperature, followed by stirring for 1 hour. To the reaction mixture, 8.4 mL of methyl iodide was added under ice cooling. The temperature of the mixture was raised to room temperature, followed by stirring for 14 hours. To the reaction mixture, water was added and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 8.47 g of 1-(2-methyl-3-bromophenyl)-4-methyl-1,4-dihydrotetrazol-5-one.

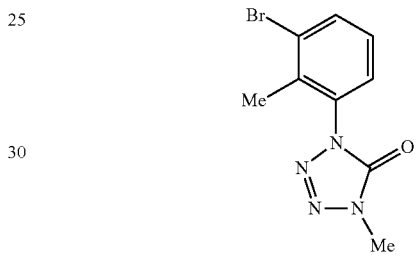

¹H-NMR (CDCl₃) δ(ppm): 2.33 (3H, s), 3.73 (3H, s), 7.21 (1H, dt, J=0.5, 7.8 Hz), 7.30 (1H, dd, J=1.0, 8.0 Hz), 7.71 (1H, dd, J=1.2, 8.3 Hz).

Reference Production Example 11

A mixture of 8.47 g of 1-(2-methyl-3-bromophenyl)-4-methyl-1,4-dihydrotetrazol-5-one mentioned in Reference Production Example 10, 1.54 g of 1,1'-azobis(cyclohexane-1-carbonitrile), 6.44 g of N-bromosuccinimide, and 125 mL of chlorobenzene was stirred with heating under reflux for 5 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 7.52 g of 1-[2-(bromomethyl)-3-bromophenyl]-4-methyl-1,4-dihydrotetrazol-5-one.

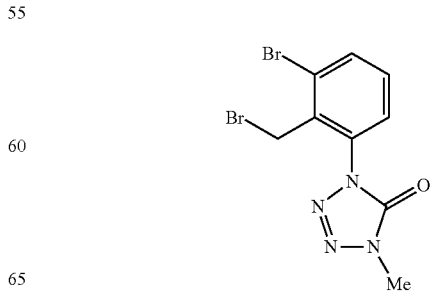

$^1$H-NMR (CDCl$_3$) δ(ppm): 3.76 (3H, s), 4.71 (2H, s), 7.34 (1H, t, J=7.8 Hz), 7.38 (1H, dd, J=8.0, 1.7 Hz), 7.77 (1H, dd, J=7.8, 1.7 Hz).

Reference Production Example 12

A mixture of 45.0 g of 1-[2-(bromomethyl)-3-bromophenyl]-4-methyl-1,4-dihydrotetrazol-5-one mentioned in Reference Production Example 11, 37.4 g of sodium methoxide, and 600 mL of tetrahydrofuran was stirred at room temperature for 3 hours. To the reaction mixture, a saturated sodium bicarbonate solution was added and the mixture was extracted with ethyl acetate. The organic layer was washed with a saturated sodium bicarbonate solution, dried over anhydrous sodium sulfate, and then concentrated under reduced pressure to obtain 36.2 g of 1-[2-(methoxymethyl)-3-bromophenyl]-4-methyl-1,4-dihydrotetrazol-5-one.

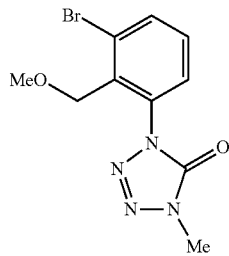 [SMILES: COCc1c(Br)cccc1-n1nnn(C)c1=O]

$^1$H-NMR (CDCl$_3$) δ(ppm): 3.23 (3H, s), 3.72 (3H, s), 4.67 (2H, s), 7.33 (1H, t, J=7.8 Hz), 7.38 (1H, dd, J=1.2, 8.1 Hz), 7.76 (1H, dd, J=1.5, 7.8 Hz).

Reference Production Example 13

A mixture of 36.2 g of 1-[2-(methoxymethyl)-3-bromophenyl]-4-methyl-1,4-dihydrotetrazol-5-one mentioned in Reference Production Example 12, 23.2 g of methylboronic acid, 66.7 g of cesium fluoride, 10.6 g of [1,1'-bis(diphenylphosphino)ferrocene]palladium(II) dichloride dichloromethane adduct, and 500 ml of 1,4-dioxane was stirred at 90° C. for 5.5 hours. After cooling, the reaction mixture was filtered and the filtrate was concentrated under reduced pressure. The residue thus obtained was subjected to silica gel column chromatography to obtain 132 g of 1-[2-(methoxymethyl)-3-methylphenyl]-4-methyl-1,4-dihydrotetrazol-5-one.

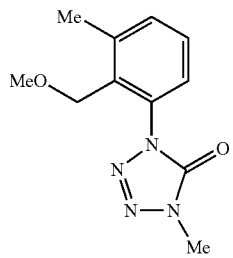 [SMILES: COCc1c(C)cccc1-n1nnn(C)c1=O]

$^1$H-NMR (CDCl$_3$) δ(ppm): 2.48 (3H, s), 3.23 (3H, s), 3.72 (3H, s), 4.42 (2H, s), 7.21 (1H, t, J=5.1 Hz), 7.35 (2H, d, J=4.8 Hz).

Reference Production Example 14

A mixture of 132 g of 1-[2-(methoxymethyl)-3-methylphenyl]-4-methyl-1,4-dihydrotetrazol-5-one mentioned in Reference Production Example 13, 50 mL of acetic acid, and 50 mL of a 25% hydrogen bromide-acetic acid solution was stirred at 65° C. for 1 hour. To the reaction mixture, a saturated saline solution was added and the mixture was extracted with ethyl acetate. The organic layer was washed with a saturated sodium bicarbonate solution, dried over anhydrous sodium sulfate, and then concentrated under reduced pressure to obtain 27.9 g of 1-[2-(bromomethyl)-3-methylphenyl]-4-methyl-1,4-dihydrotetrazol-5-one.

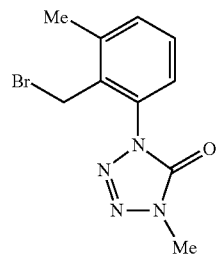

$^1$H-NMR (CDCl$_3$) δ(ppm): 2.51 (3H, s), 3.75 (3H, s), 4.51 (2H, s), 7.22-7.24 (1H, m), 7.36-7.39 (2H, m).

Reference Production Example 15

A mixture of 30.1 g of 1-[2-(methoxymethyl)-3-bromophenyl]-4-methyl-1,4-dihydrotetrazol-5-one mentioned in Reference Production Example 12, 12.9 g of cyclopropylboronic acid, 46.2 g of cesium fluoride, 8.2 g of [1,1'-bis(diphenylphosphino)ferrocene]palladium(II) dichloride dichloromethane adduct, and 680 ml of 1,4-dioxane was stirred at 90° C. for 4 hours. After cooling, the reaction mixture was filtered and the filtrate was concentrated under reduced pressure. The residue thus obtained was subjected to silica gel column chromatography to obtain 26.0 g of 1-[2-(methoxymethyl)-3-cyclopropylphenyl]-4-methyl-1,4-dihydrotetrazol-5-one.

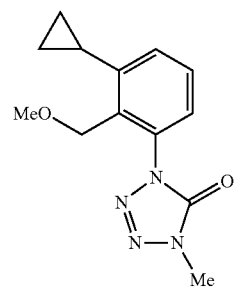 [SMILES: COCc1c(C2CC2)cccc1-n1nnn(C)c1=O]

$^1$H-NMR (CDCl$_3$) δ(ppm): 7.36 (1H, t, J=8.0 Hz), 7.20 (2H, d, J=8.0 Hz), 4.64 (2H, s), 3.72 (3H, s), 3.24 (3H, s), 2.20-2.13 (1H, m), 1.04-1.00 (2H, m), 0.76-0.72 (2H, m).

Reference Production Example 16

A mixture of 26.0 g of 1-[2-(methoxymethyl)-3-cyclopropylphenyl]-4-methyl-1,4-dihydrotetrazol-5-one mentioned in Reference Production Example 15, 40 mL of acetic acid, and 40 mL of a 25% hydrogen bromide-acetic acid solution was stirred at 65° C. for 2 hours. To the reaction mixture, a saturated saline solution was added and the mixture was extracted with ethyl acetate. The organic layer was washed with a saturated sodium bicarbonate solution, dried over anhydrous sodium sulfate, and then concentrated under reduced pressure to obtain 30.8 g of 1-[2-(bromomethyl)-3-cyclopropylphenyl]-4-methyl-1,4-dihydrotetrazol-5-one.

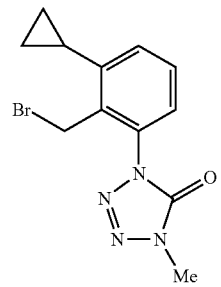 [SMILES: Cn1nnn(-c2cccc(C3CC3)c2CBr)c1=O]

¹H-NMR (CDCl₃) δ(ppm): 7.38 (1H, t, J=7.8 Hz), 7.26-7.22 (2H, m), 4.77 (2H, s), 3.75 (3H, s), 2.16-2.09 (1H, m), 1.10-1.06 (2H, m), 0.82-0.78 (2H, m).

Reference Production Example 17

A mixture of 2.83 g of 1-[2-(bromomethyl)-3-methylphenyl]-4-methyl-1,4-dihydrotetrazol-5-one mentioned in Reference Production Example 14, 1.36 g of 3-hydroxyacetophenone, 2.76 g of potassium carbonate, and 40 mL of acetonitrile was stirred with heating under reflux for 4 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 2.95 g of 1-{2-[(3-acetylphenoxy)methyl]-3-methylphenyl}-4-methyl-1,4-dihydrotetrazol-5-one.

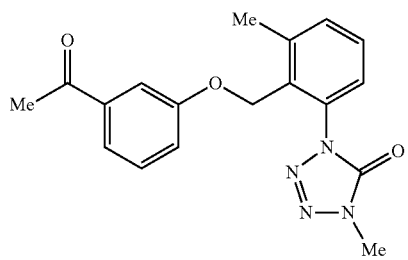 [SMILES: CC(=O)c1cccc(OCc2c(C)cccc2-n2nnn(C)c2=O)c1]

¹H-NMR (CDCl₃) δ: 7.56-7.54 (1H, m), 7.46-7.40 (3H, m), 7.36 (1H, t, J=8.0 Hz), 7.29 (1H, dd, J=6.9, 2.7 Hz), 7.07 (1H, dd, J=8.0, 2.7 Hz), 5.08 (2H, s), 3.63 (3H, s), 2.58 (3H, s), 2.50 (3H, s).

Reference Production Example 18

A mixture of 2.83 g of 1-[2-(bromomethyl)-3-methylphenyl]-4-methyl-1,4-dihydrotetrazol-5-one mentioned in Reference Production Example 14, 1.50 g of 3-hydroxy-4-methylacetophenone, 2.76 g of potassium carbonate, and 40 mL of acetonitrile was stirred with heating under reflux for 4 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 2.93 g of 1-{2-[(5-acetyl-2-methylphenoxy)methyl]-3-methylphenyl}-4-methyl-1,4-dihydrotetrazol-5-one.

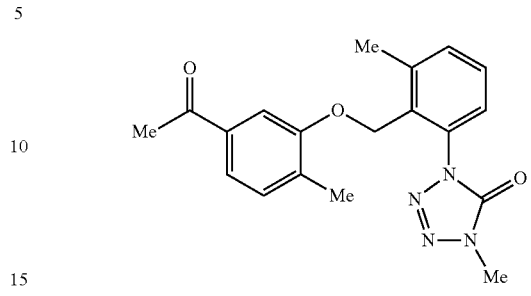

¹H-NMR (CDCl₃) δ: 7.46 (1H, dd, J=7.8, 1.3 Hz), 7.44-7.40 (3H, m), 7.29-7.26 (1H, m), 7.18 (1H, d, J=7.8 Hz), 5.09 (2H, s), 3.64 (3H, s), 2.58 (3H, s), 2.51 (3H, s), 2.14 (3H, s).

Reference Production Example 19

A mixture of 0.54 g of 1-{2-[(3-acetylphenoxy)methyl]-3-methylphenyl}-4-methyl-1,4-dihydrotetrazol-5-one mentioned in Reference Production Example 17, 0.10 g of hydroxylamine hydrochloride, 1.5 ml of pyridine, and 6 mL of ethanol was stirred with heating under reflux for 4 hours. After concentration under reduced pressure, the residue thus obtained was filtered, washed with methyl tert-butyl ketone and hexane to obtain 0.40 g of 1-[2-{3-[1-(hydroxyimino)ethyl]phenoxy}methyl]-3-methylphenyl]-4-methyl-1,4-dihydrotetrazol-5-one.

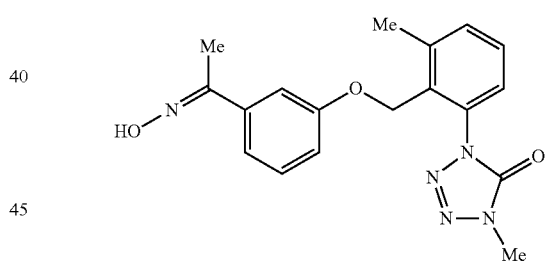

¹H-NMR (CDCl₃) δ: 7.91 (1H, t, J=6.6 Hz), 7.44-7.39 (2H, m), 7.31-7.24 (1H, m), 7.23-7.19 (1H, m), 7.19-7.14 (1H, m), 6.92-6.86 (1H, m), 5.04 (2H, s), 3.62 (3H, s), 2.49 (3H, s), 2.25 (3H, s).

Reference Production Example 20

A mixture of 1.06 g of 1-{2-[(5-acetyl-2-methylphenoxy)methyl]-3-methylphenyl}-4-methyl-1,4-dihydrotetrazol-5-one mentioned in Reference Production Example 18, 0.21 g of hydroxylamine hydrochloride, 3 ml of pyridine, and 12 mL of ethanol was stirred with heating under reflux for 4 hours. After concentration under reduced pressure, the residue thus obtained was filtered, washed with methyl tert-butyl ketone and hexane to obtain 1.05 g of 1-[2-({5-[1-(hydroxyimino)ethyl]-2-methylphenoxy}methyl)-3-methylphenyl]-4-methyl-1,4-dihydrotetrazol-5-one.

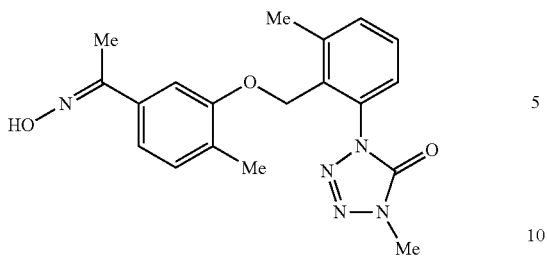

¹H-NMR (CDCl₃) δ: 7.62 (1H, s), 7.45-7.38 (2H, m), 7.30-7.26 (1H, m), 7.17 (1H, brs), 7.13-7.05 (2H, m), 5.07 (2H, s), 3.63 (3H, s), 2.50 (3H, s), 2.25 (3H, s), 2.10 (3H, s).

Reference Production Example 21

A mixture of 8.97 g of 1-[2-(bromomethyl)-3-methoxyphenyl]-4-methyl-1,4-dihydrotetrazol-5-one mentioned in Reference Production Example 7, 33.0 g of resorcinol, 8.29 g of potassium carbonate, and 120 mL of acetonitrile was stirred with heating under reflux for 4 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 9.69 g of 1-{2-[(3-hydroxyphenoxy)methyl]-3-methoxyphenyl}-4-methyl-1,4-dihydrotetrazol-5-one.

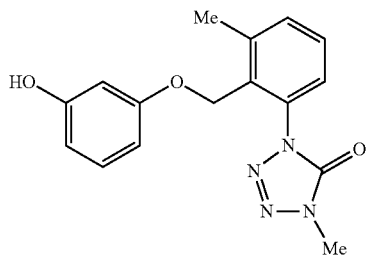

¹H-NMR (CDCl₃) δ: 7.47 (1H, t, J=8.2 Hz), 7.11-7.05 (3H, m), 6.42-6.39 (2H, m), 6.33-6.30 (1H, m), 5.67 (1H, br s), 5.19 (2H, s), 3.92 (3H, s), 3.60 (3H, s).

Reference Production Example 22

A mixture of 5.0 g of 1-[2-(bromomethyl)-3-methylphenyl]-4-methyl-1,4-dihydrotetrazol-5-one mentioned in Reference Production Example 14, 5.5 g of resorcinol, 6.9 g of potassium carbonate, and 100 mL of acetonitrile was stirred with heating under reflux for 4 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 4.0 g of 1-{2-[(3-hydroxyphenoxy)methyl]-3-methylphenyl}-4-methyl-1,4-dihydrotetrazol-5-one 1-{2-[(3-hydroxyphenoxy)methyl]-3-methylphenyl}-4-methyl-1,4-dihydrotetrazol-5-one.

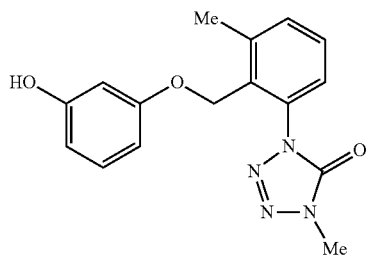 [SMILES: Cc1cccc(-n2nnn(C)c2=O)c1COc1cccc(O)c1]

¹H-NMR (CDCl₃) δ: 7.43-7.37 (2H, m), 7.27-7.24 (1H, m), 7.10 (1H, t, J=8.2 Hz), 6.46-6.41 (2H, m), 6.31 (1H, t, J=2.3 Hz), 5.16 (1H, br s), 5.00 (2H, s), 3.65 (3H, s), 2.49 (3H, s).

Reference Production Example 23

To a mixture of 6.09 g of 3-methoxybenzoic acid, 0.1 mL of N,N-dimethylformamide, and 80 mL of tetrahydrofuran, 5.56 g of oxalyl chloride was added, followed by stirring at room temperature for 2 hours. The reaction solution was concentrated under reduced pressure, and 4.68 g of N,O-dimethylhydroxylamine hydrochloride, 12.4 g of N,N-diisopropylethylamine, and 80 mL of chloroform were added to the residue thus obtained, followed by stirring at room temperature for 4 hours. The reaction solution was concentrated under reduced pressure and the residue thus obtained was subjected to silica gel column chromatography to obtain 7.55 g of N,3-dimethoxy-N-methylbenzamide.

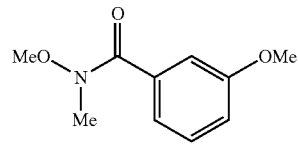 [SMILES: COc1cccc(C(=O)N(C)OC)c1]

¹H-NMR (CDCl₃) δ: 7.32 (1H, t, J=7.9 Hz), 7.26-7.23 (1H, m), 7.21-7.19 (1H, m), 7.02-6.98 (1H, m), 3.84 (3H, s), 3.58 (3H, s), 3.36 (3H, s).

Reference Production Example 24

To a mixture of 1.95 g of N,3-dimethoxy-N-methylbenzamide mentioned in Reference Production Example 23 and 20 mL of tetrahydrofuran, 15.8 mL of ethylmagnesium bromide (13% tetrahydrofuran solvent) was added at 0° C., followed by stirring at room temperature for 2 hours. To the reaction solution, water was added and the mixture was extracted with ethyl acetate. The organic layer was washed with water and a saturated saline solution, dried over anhydrous magnesium sulfate, and then concentrated under reduced pressure to obtain 1.73 g of 1-(3-methoxyphenyl)propan-1-one.

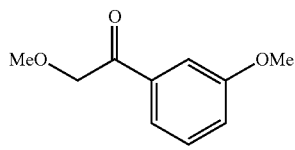 [SMILES: COCC(=O)c1cccc(OC)c1]

¹H-NMR (CDCl₃) δ: 7.57-7.53 (1H, m), 7.51-7.49 (1H, m), 7.37 (1H, t, J=7.9 Hz), 7.12-7.08 (1H, m), 3.86 (3H, s), 3.00 (2H, q, J=7.3 Hz), 1.22 (3H, t, J=7.3 Hz).

Reference Production Example 25

A mixture of 1.64 g of 1-(3-methoxyphenyl)propan-1-one mentioned in Reference Production Example 24, 10 mL of acetic acid, and 10 mL of 48% hydrobromic acid was stirred with heating at 100° C. for 6 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.73 g of 1-(3-hydroxyphenyl)propan-1-one.

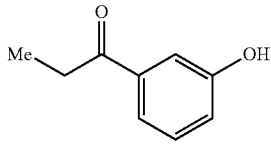

¹H-NMR (CDCl₃) δ: 7.55-7.52 (2H, m), 7.34 (1H, t, J=7.9 Hz), 7.10-7.05 (1H, m), 5.90 (1H, br s), 3.00 (2H, q, J=7.3 Hz), 1.23 (3H, t, J=7.3 Hz).

Reference Production Example 26

To a mixture of 1.95 g of N,3-dimethoxy-N-methylbenzamide mentioned in Reference Production Example 23 and 20 mL of tetrahydrofuran, 30 mL of cyclopropylmagnesium bromide (8% tetrahydrofuran solvent) was added at 0° C., followed by stirring at room temperature for 2 hours. To the reaction solution, water was added and the mixture was extracted with ethyl acetate. The organic layer was washed with water and a saturated saline solution, dried over anhydrous magnesium sulfate, and then concentrated under reduced pressure to obtain 2.08 g of cyclopropyl(3-methoxyphenyl)methanone.

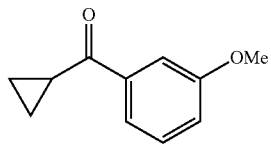 [SMILES: COc1cccc(C(=O)C2CC2)c1]

¹H-NMR (CDCl₃) δ: 7.63 (1H, d, J=7.8 Hz), 7.53-7.51 (1H, m), 7.39 (1H, t, J=8.0 Hz), 7.14-7.10 (1H, m), 3.87 (3H, s), 2.71-2.62 (1H, m), 1.27-1.22 (2H, m), 1.07-1.02 (2H, m).

Reference Production Example 27

A mixture of 5.66 g of 1-[2-(bromomethyl)-3-methylphenyl]-4-methyl-1,4-dihydrotetrazol-5-one mentioned in Reference Production Example 14, 3.46 g of 3-bromophenol, 5.53 g of potassium carbonate, and 80 mL of acetonitrile was stirred with heating under reflux for 4 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 7.02 g of 1-{2-[(3-bromophenoxy)methyl]-3-methylphenyl}-4-methyl-1,4-dihydrotetrazol-5-one.

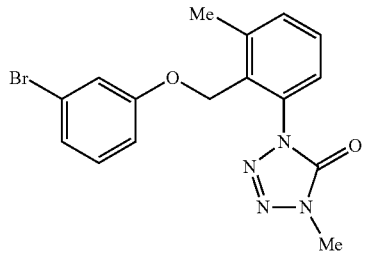 [SMILES: Cc1cccc(-n2nnn(C)c2=O)c1COc1cccc(Br)c1]

¹H-NMR (CDCl₃) δ: 7.45-7.39 (2H, m), 7.30-7.25 (1H, m), 7.16-7.07 (2H, m), 7.05-7.02 (1H, m), 6.82-6.78 (1H, m), 5.00 (2H, s), 3.64 (3H, s), 2.49 (3H, s).

Reference Production Example 28

A mixture of 0.88 g of 1-(3-hydroxyphenyl)propan-1-one mentioned in Reference Production Example 25, 0.49 g of O-methylhydroxylamine hydrochloride, 0.3 mL of 35% hydrochloric acid, and 12 mL of ethanol was stirred at room temperature for 2 hours. To the reaction solution, an aqueous saturated sodium hydrogen carbonate solution was added and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.03 g of 3-[1-(methoxyimino)propyl]phenol.

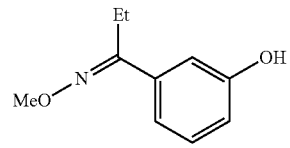 [SMILES: CCC(=NOC)c1cccc(O)c1]

¹H-NMR (CDCl₃) δ: 7.26-7.22 (1H, m), 7.20-7.16 (1H, m), 7.15-7.13 (1H, m), 6.86-6.82 (1H, m), 4.86 (1H, br s), 3.98 (3H, s), 2.72 (2H, q, J=7.6 Hz), 1.13 (3H, t, J=7.6 Hz).

Reference Production Example 29

To a mixture of 1.95 g of 3,N-dimethoxy-N-methylbenzamide mentioned in Reference Production Example 23 and 10 mL of tetrahydrofuran, 10 mL of butylmagnesium chloride (23% tetrahydrofuran solvent) was added at 0° C., followed by stirring at room temperature for 2 hours. To the reaction solution, water was added and the mixture was extracted with ethyl acetate. The organic layer was washed with water and a saturated saline solution, dried over anhydrous magnesium sulfate, and then concentrated under reduced pressure to obtain 2.21 g of 1-(3-methoxyphenyl)pentan-1-one.

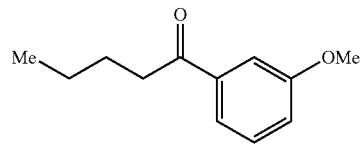 [SMILES: CCCCC(=O)c1cccc(OC)c1]

$^1$H-NMR (CDCl$_3$) δ: 7.57-7.51 (1H, m), 7.50-7.46 (1H, m), 7.37-7.33 (1H, m), 7.13-7.07 (1H, m), 3.85 (3H, s), 2.94 (2H, t, J=7.3 Hz), 1.76-1.66 (2H, m), 1.46-1.35 (2H, m), 0.94 (3H, t, J=7.2 Hz).

Reference Production Example 30

A mixture of 1.92 g of 1-(3-methoxyphenyl)pentan-1-one mentioned in Reference Production Example 29, 10 mL of acetic acid, and 10 mL of 48% hydrobromic acid was stirred with heating at 100° C. for 6 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.71 g of 1-(3-hydroxyphenyl)pentan-1-one.

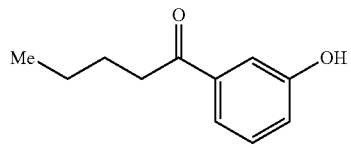

$^1$H-NMR (CDCl$_3$) δ: 7.61-7.60 (1H, m), 7.54-7.50 (1H, m), 7.34 (1H, t, J=7.9 Hz), 7.13-7.08 (1H, m), 2.96 (2H, t, J=7.4 Hz), 1.76-1.67 (2H, m), 1.45-1.35 (2H, m), 0.94 (3H, t, J=7.3 Hz).

Reference Production Example 31

A mixture of 1.76 g of cyclopropyl(3-methoxyphenyl)methanone mentioned in Reference Production Example 26, 10 mL of acetic acid, and 10 mL of 48% hydrobromic acid was stirred with heating at 100° C. for 6 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography. To the solid thus obtained, 0.28 g of 1-[2-(bromomethyl)-3-methylphenyl]-4-methyl-1,4-dihydrotetrazol-5-one mentioned in Reference Production Example 14, 0.28 g of potassium carbonate, and 4 mL of acetonitrile was added, followed by stirring with heating at 80° C. under reflux for 4 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.14 g of 1-{2-[(3-cyclopropanecarbonylphenoxy)methyl]-3-methylphenyl}-4-methyl-1,4-dihydrotetrazol-5-one.

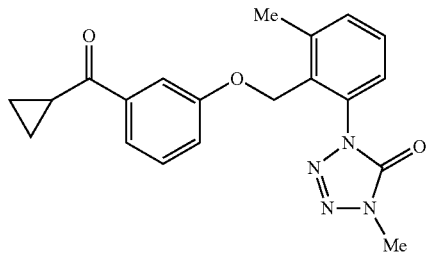 [SMILES: Cc1cccc(-n2nnn(C)c2=O)c1COc1cccc(C(=O)C2CC2)c1]

$^1$H-NMR (CDCl$_3$) δ: 7.64 (1H, d, J=7.6 Hz), 7.50-7.48 (1H, m), 7.46-7.35 (3H, m), 7.29 (1H, dd, J=7.0, 2.2 Hz), 7.09-7.05 (1H, m), 5.08 (2H, s), 3.63 (3H, s), 2.66-2.62 (1H, m), 2.50 (3H, s), 1.27-1.22 (2H, m), 1.08-1.02 (2H, m).

Reference Production Example 32

A mixture of 1.66 g of 1-(3-hydroxyphenyl)pentan-1-one mentioned in Reference Production Example 30, 0.84 g of O-methylhydroxylamine hydrochloride, 4 mL of pyridine, and 20 mL of ethanol was stirred with heating at 80° C. under reflux for 4 hours. To the reaction solution, an aqueous saturated sodium hydrogen carbonate solution was added and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.03 g of 3-[1-(methoxyimino)butyl]phenol.

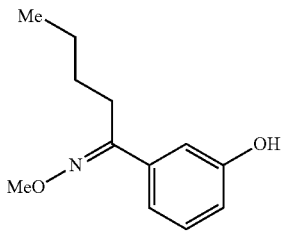 [SMILES: CCCCC(=NOC)c1cccc(O)c1]

$^1$H-NMR (CDCl$_3$) δ: 7.36-7.31 (1H, m), 7.24 (1H, t, J=7.9 Hz), 7.19-7.12 (1H, m), 6.87-6.82 (1H, m), 3.97 (3H, s), 2.70 (2H, t, J=7.8 Hz), 1.53-1.45 (2H, m), 1.41-1.33 (2H, m), 0.91 (3H, t, J=7.2 Hz).

Reference Production Example 33

Under ice cooling, a mixture of 7.00 g of 1-[2-(bromomethyl)-3-methylphenyl]-4-methyl-1,4-dihydrotetrazol-5-one mentioned in Reference Production Example 14, 9.90 g of calcium carbonate, 80 ml of 1,4-dioxane, and 80 ml of water was stirred with heating under reflux for 7 hours. After cooling, water was added to the reaction solution and the mixture was extracted with ethyl acetate. The organic layer was washed with water and a saturated saline solution, dried over anhydrous magnesium sulfate, and then concentrated under reduced pressure to obtain 4.68 g of 1-[2-(hydroxymethyl)-3-methylphenyl]-4-methyl-1,4-dihydrotetrazol-5-one.

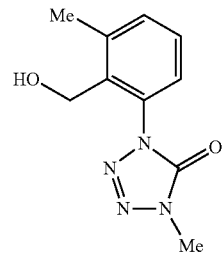

$^1$H-NMR (CDCl$_3$) δ(ppm): 7.39-7.34 (2H, m), 7.23-7.18 (1H, m), 4.48 (2H, d, J=7.1 Hz), 3.75 (3H, s), 2.56 (3H, s).

Reference Production Example 34

To a mixture of 4.68 g of 1-[2-(hydroxymethyl)-3-methylphenyl]-4-methyl-1,4-dihydrotetrazol-5-one mentioned in Reference Production Example 33 and 100 mL of tetrahydrofuran, 1.02 g of 55% sodium hydride was added under ice cooling, followed by stirring for 30 minutes. Under ice cooling, 5.03 g of 2,6-dibromopyridine was added to the reaction mixture. The temperature of the mixture was raised to room temperature, followed by stirring for 13 hours. To the reaction mixture, water was added and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 6.99 g of 1-{2-[(6-bromopyridin-2-yloxy)methyl]-3-methylphenyl}-4-methyl-1,4-dihydrotetrazol-5-one.

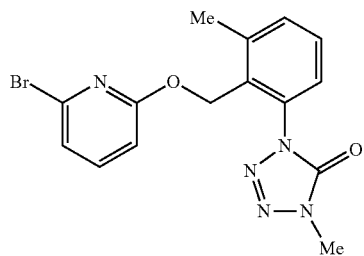 [SMILES: Cc1cccc(-n2nnn(C)c2=O)c1COc1cccc(Br)n1]

¹H-NMR (CDCl₃) δ(ppm): 7.41-7.35 (3H, m), 7.25-7.23 (1H, m), 7.03 (1H, d, J=7.3 Hz), 6.59 (1H, d, J=8.2 Hz), 5.39 (2H, s), 3.69 (3H, s), 2.56 (3H, s).

Reference Production Example 35

A mixture of 1.36 g of 3-acetylphenol, 0.84 g of O-methylhydroxylamine hydrochloride, 0.5 mL of 35% hydrochloric acid, and 40 mL of ethanol was stirred at room temperature for 2 hours. To the reaction solution, an aqueous saturated sodium hydrogen carbonate solution was added and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 2.10 g of 3-[1-(methoxyimino)ethyl]phenol.

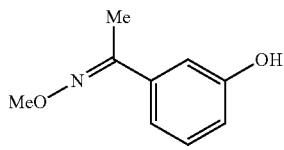

¹H-NMR (CDCl₃) δ: 7.23 (1H, t, J=7.7 Hz), 7.19-7.13 (2H, m), 6.84-6.82 (1H, m), 5.33 (1H, br s), 3.99 (3H, s), 2.20 (3H, s).

Reference Production Example 36

A mixture of 1.35 g of 2-chloro-6-acetylpyridine, 0.84 g of O-methylhydroxylamine hydrochloride, 0.5 mL of 35% hydrochloric acid, and 40 mL of ethanol was stirred at room temperature for 2 hours. To the reaction solution, an aqueous saturated sodium hydrogen carbonate solution was added and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.69 g of 6-[1-(methoxyimino)ethyl]-2-chloropyridine.

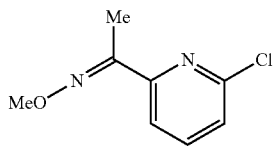 [SMILES: CON=C(C)c1cccc(Cl)n1]

¹H-NMR (CDCl₃) δ: 7.85 (1H, d, J=7.7 Hz), 7.62 (1H, t, J=7.7 Hz), 7.28 (1H, d, J=7.7 Hz), 4.03 (3H, s), 2.29 (3H, s).

Reference Production Example 37

A mixture of 1.50 g of 5-acetyl-2-methylphenol, 0.84 g of O-methylhydroxylamine hydrochloride, 0.5 mL of 35% hydrochloric acid, and 40 mL of ethanol was stirred at room temperature for 2 hours. To the reaction solution, an aqueous saturated sodium hydrogen carbonate solution was added and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.98 g of 3-[1-(methoxyimino)ethyl]-6-methylphenol.

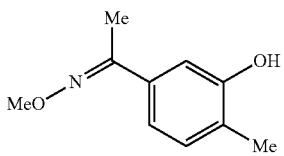 [SMILES: CON=C(C)c1ccc(C)c(O)c1]

¹H-NMR (CDCl₃) δ: 7.12-7.06 (3H, m), 5.25 (1H, br s), 3.98 (3H, s), 2.24 (3H, s), 2.18 (3H, s).

Reference Production Example 38

A mixture of 5.66 g of 1-[2-(bromomethyl)-3-methylphenyl]-4-methyl-1,4-dihydrotetrazol-5-one mentioned in Reference Production Example 14, 3.04 g of methyl 3-hydroxybenzoate, 5.53 g of potassium carbonate, and 80 mL of acetonitrile was stirred with heating under reflux for 4 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 7.08 g of 1-(2-{[3-(methoxycarbonyl)phenoxy]methyl}-3-methylphenyl)-4-methyl-1,4-dihydrotetrazol-5-one.

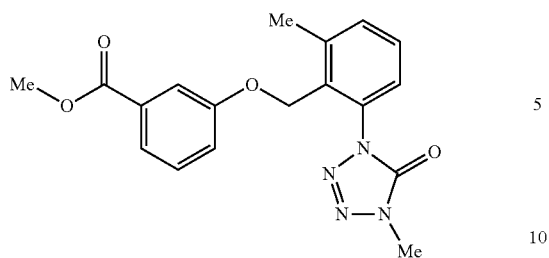

¹H-NMR (CDCl₃) δ: 7.68-7.65 (1H, m), 7.56-7.54 (1H, m), 7.47-7.40 (2H, m), 7.34 (1H, t, J=8.0 Hz), 7.30 (1H, dd, J=7.3, 2.1 Hz), 7.09-7.05 (1H, m), 5.08 (2H, s), 3.93 (3H, s), 3.64 (3H, s), 2.51 (3H, s).

Reference Production Example 39

To a mixture of 4.11 g of 1-(2-{[3-(methoxycarbonyl)phenoxy]methyl}-3-methylphenyl)-4-methyl-1,4-dihydrotetrazol-5-one mentioned in Reference Production Example 38 and 46 mL of tetrahydrofuran, 0.76 g of lithium borohydride was added, followed by stirring at 60° C. for 8 hours. To the reaction solution, an aqueous saturated sodium hydrogen carbonate solution was added and the mixture was extracted with chloroform. The organic layer was washed with water and a saturated saline solution, dried over anhydrous magnesium sulfate. The residue thus obtained was subjected to silica gel column chromatography to obtain 3.12 g of 1-(2-{[3-(hydroxymethyl)phenoxy]methyl}-3-methylphenyl)-4-methyl-1,4-dihydrotetrazol-5-one.

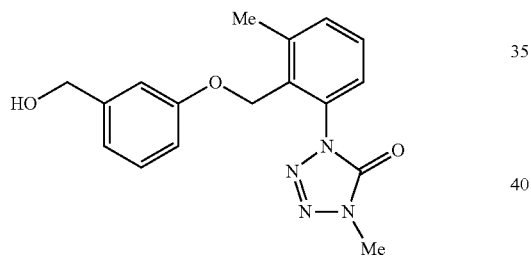

¹H-NMR (CDCl₃) δ: 7.42-7.36 (2H, m), 7.26-7.19 (2H, m), 6.92 (1H, d, J=7.6 Hz), 6.85-6.82 (1H, m), 6.78 (1H, dd, J=8.1, 2.4 Hz), 5.03 (2H, s), 4.61 (2H, d, J=3.7 Hz), 3.60 (3H, s), 2.48 (3H, s).

In accordance with the process mentioned above, it is possible to obtain compounds Q1A-001 to Q11I-436.

The compounds Q1A-001 to Q11I-436 (hereinafter referred to as the present compound A) represent aromatic compounds shown below [wherein Y represents any one of the following substituent numbers 1 to 436].

(Q1A)
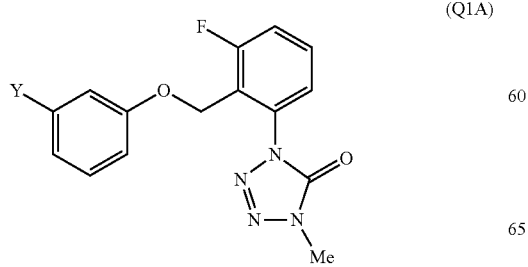

(Q1B)
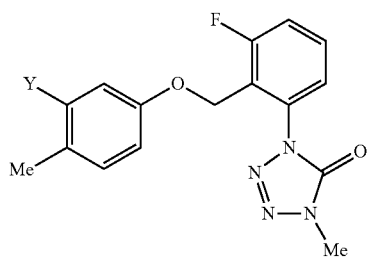

(Q1C)
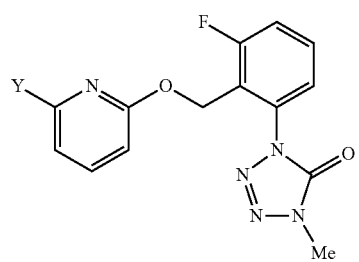

(Q1D)
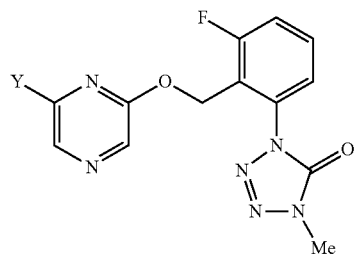

(Q1E)
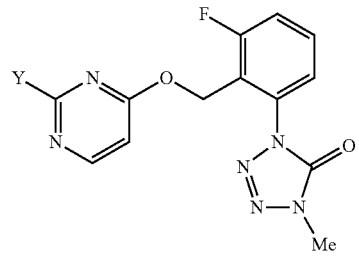

(Q1F)
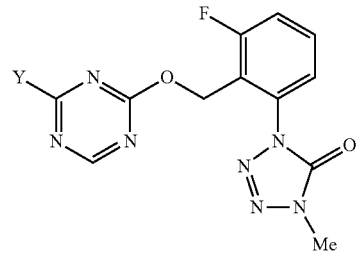

(Q1G)
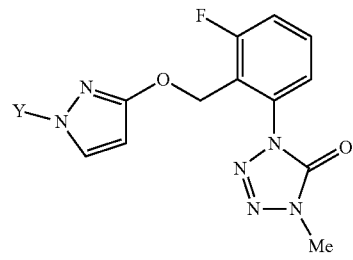

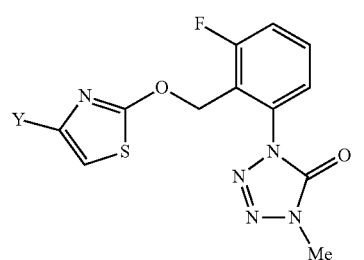 (Q1H)
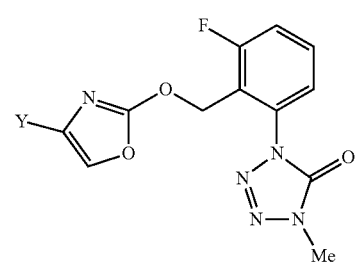 (Q1I)
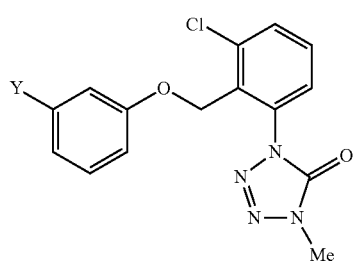 (Q2A)
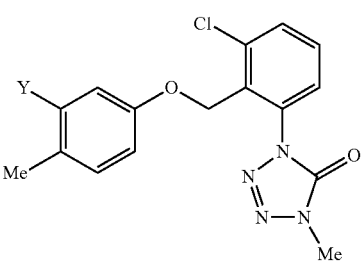 (Q2B)
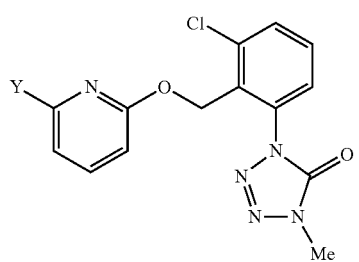 (Q2C)
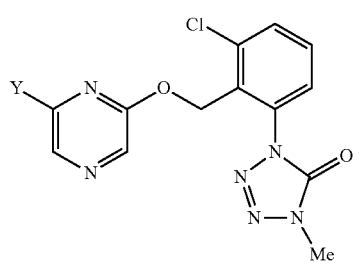 (Q2D)
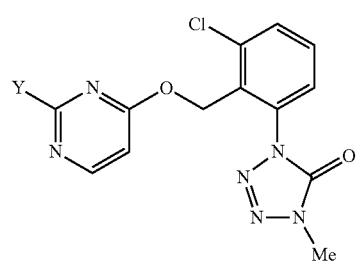 (Q2E)
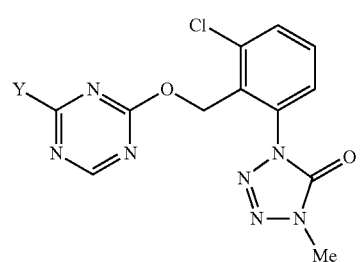 (Q2F)
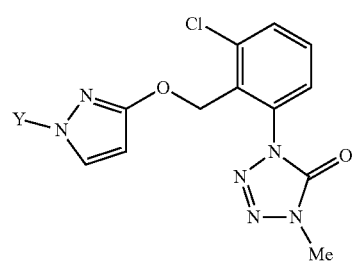 (Q2G)
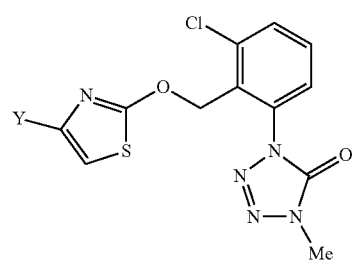 (Q2H)
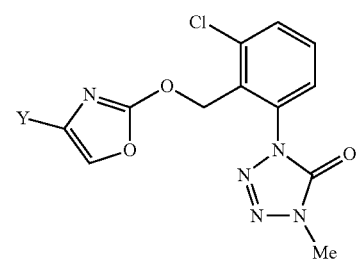 (Q2I)
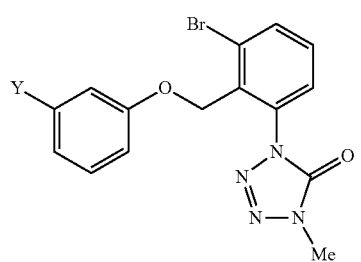 (Q3A)

-continued
(Q3B)
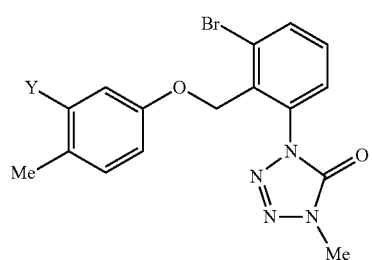
(Q3C)
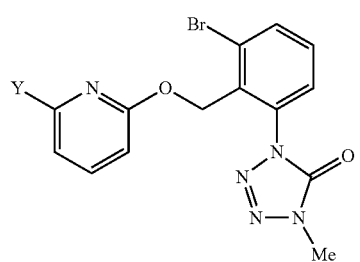
(Q3D)
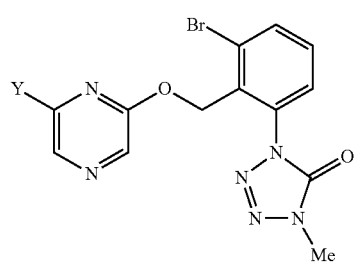
(Q3E)
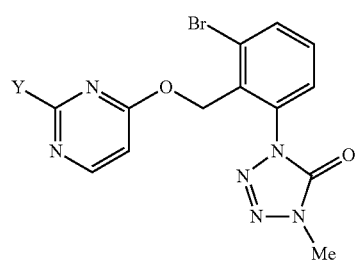
(Q3F)
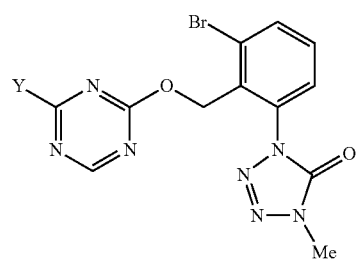
(Q3G)
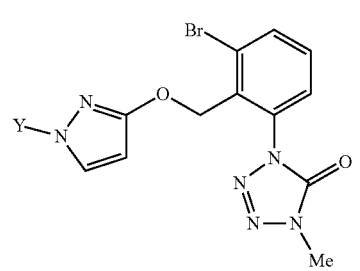
-continued
(Q3H)
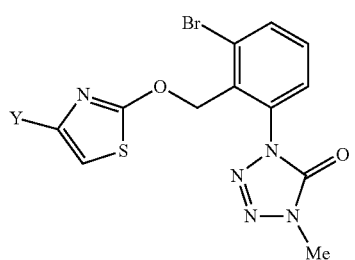
(Q3I)
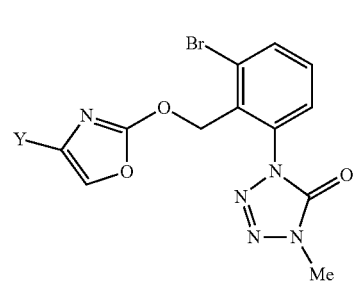
(Q4A)
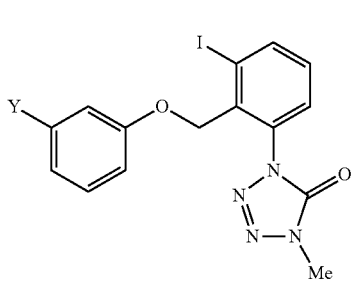
(Q4B)
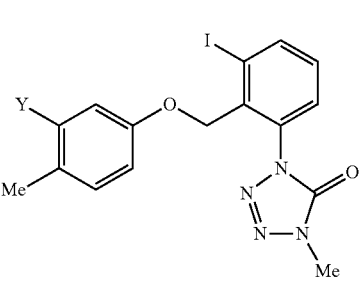
(Q4C)
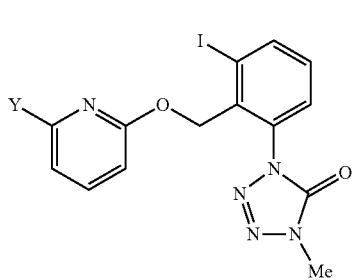
(Q4D)
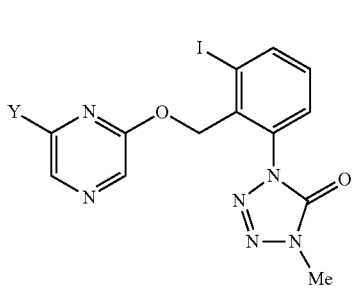

-continued
(Q4E)
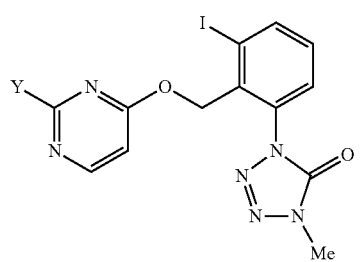
(Q4F)
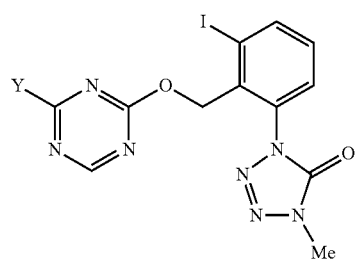
(Q4G)
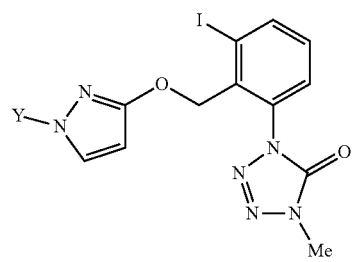
(Q4H)
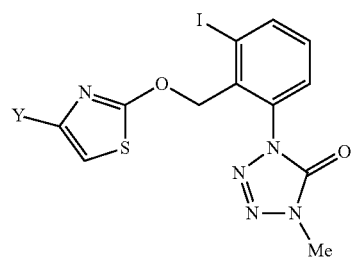
(Q4I)
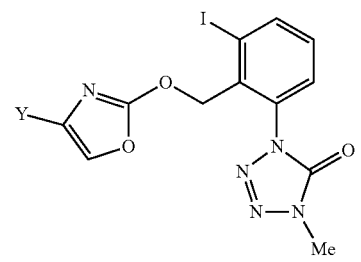
(Q5A)
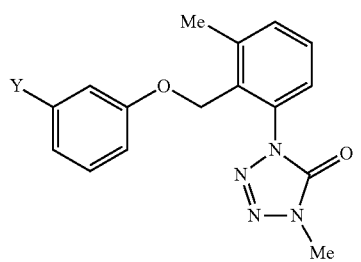
-continued
(Q5B)
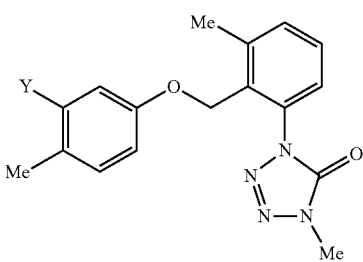
(Q5C)
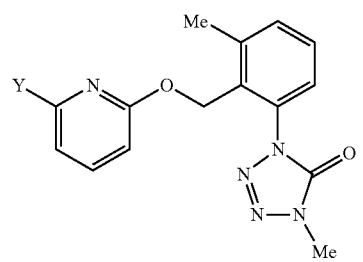
(Q5D)
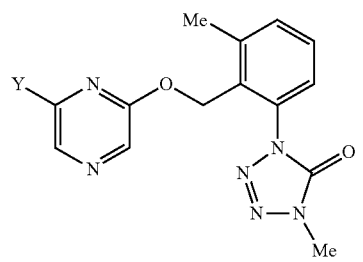
(Q5E)
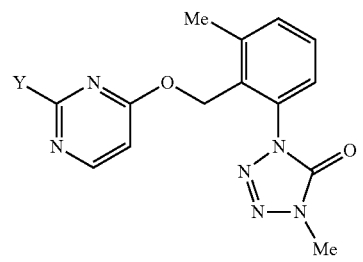
(Q5F)
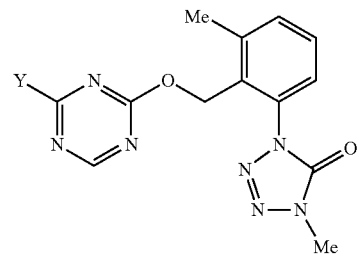
(Q5G)
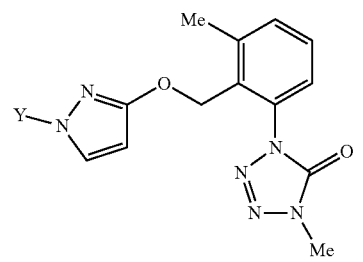

-continued
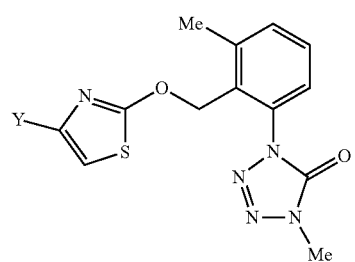 (Q5H)
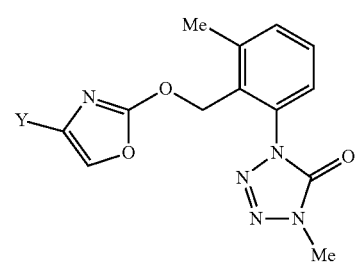 (Q5I)
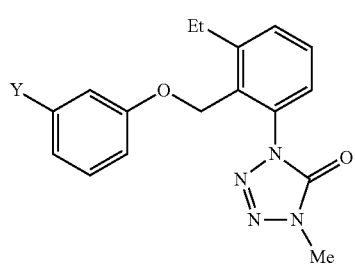 (Q6A)
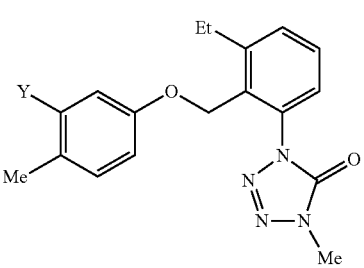 (Q6B)
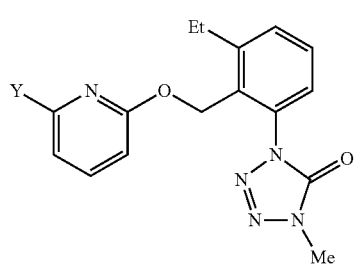 (Q6C)
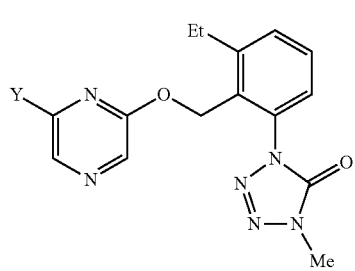 (Q6D)
-continued
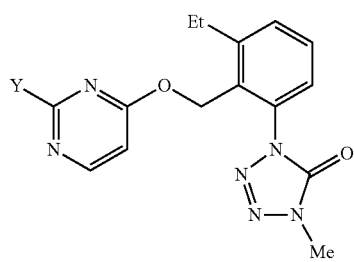 (Q6E)
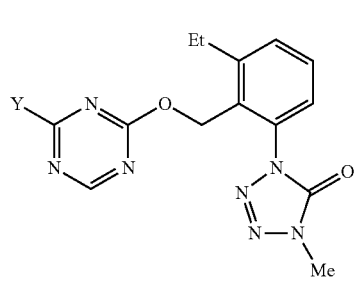 (Q6F)
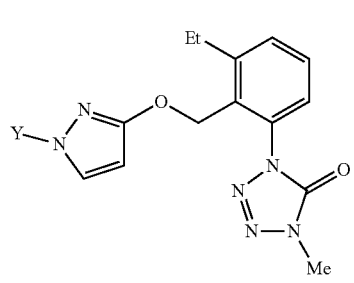 (Q6G)
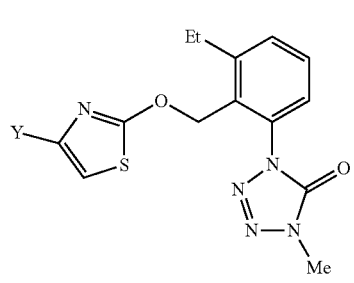 (Q6H)
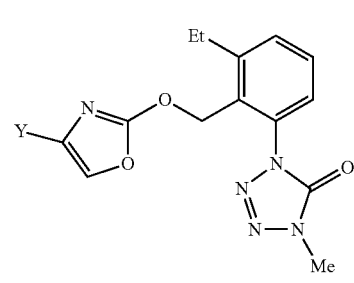 (Q6I)
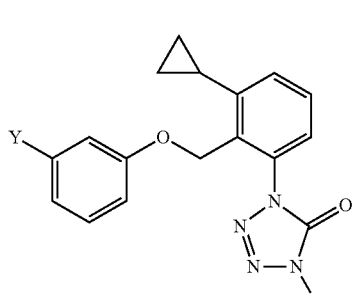 (Q7A)

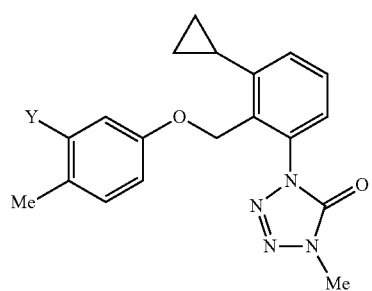
(Q7B)
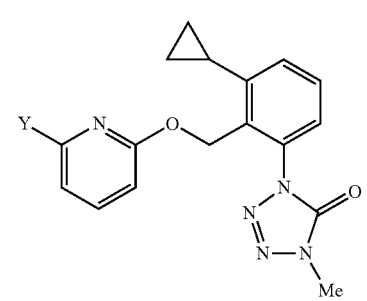
(Q7C)
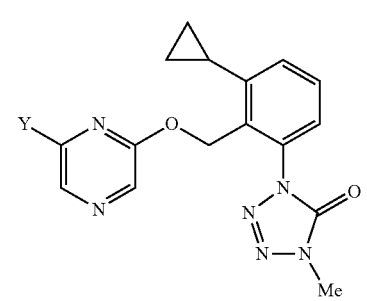
(Q7D)
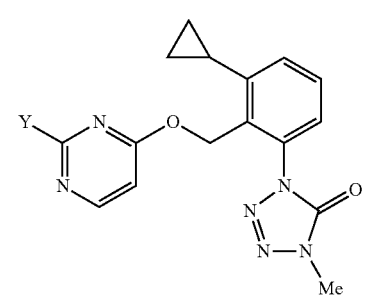
(Q7E)
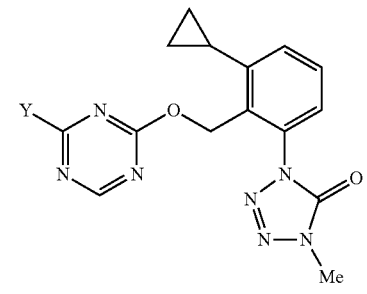
(Q7F)
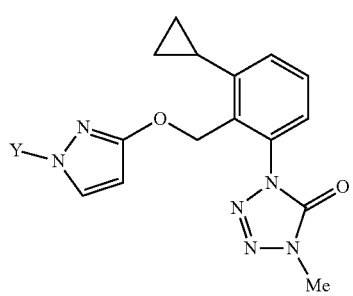
(Q7G)
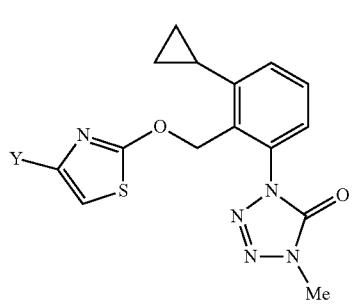
(Q7H)
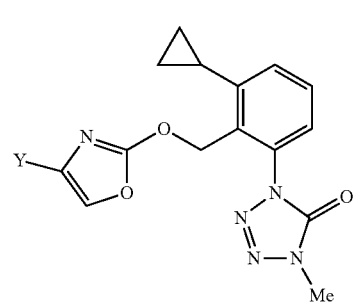
(Q7I)
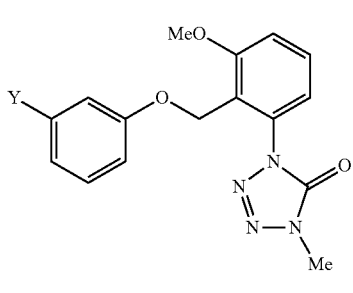
(Q8A)
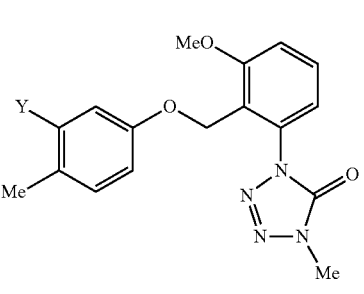
(Q8B)

111  -continued
(Q8C)
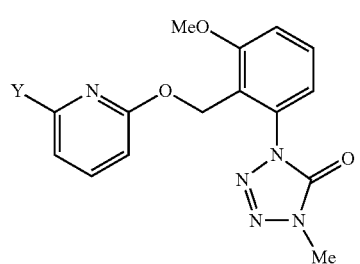
(Q8D)
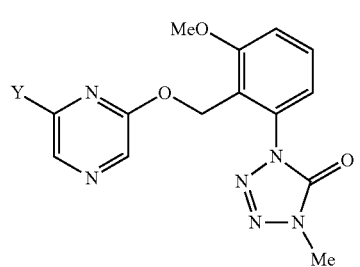
(Q8E)
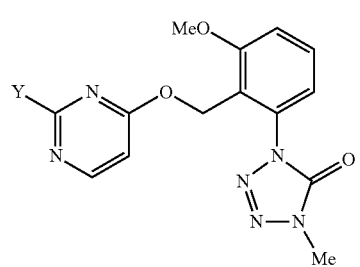
(Q8F)
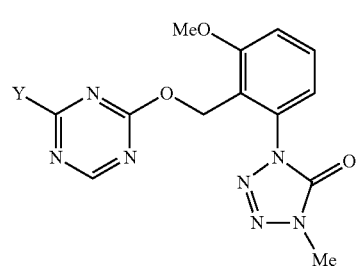
(Q8G)
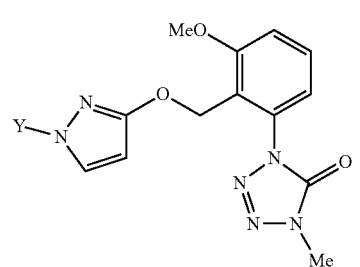
(Q8H)
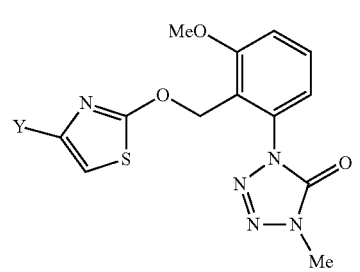
112  -continued
(Q8I)
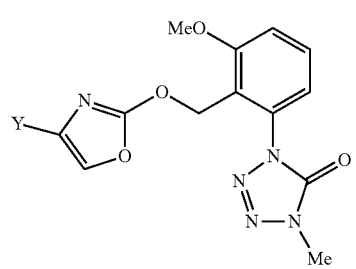
(Q9A)
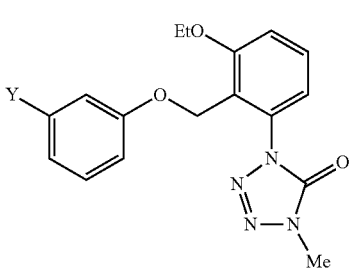
(Q9B)
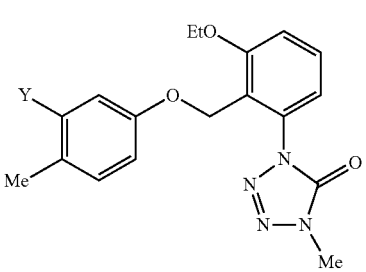
(Q9C)
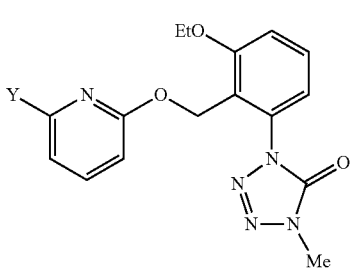
(Q9D)
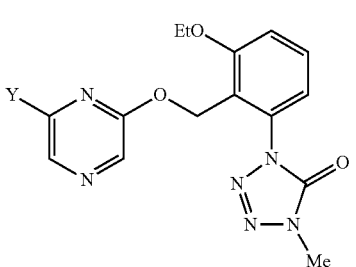
(Q9E)
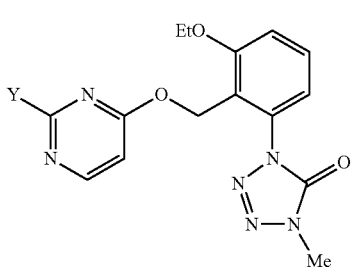

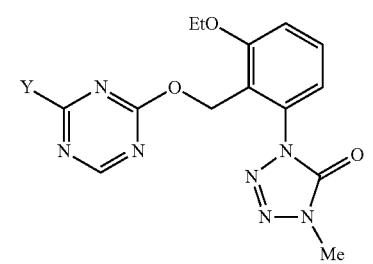 (Q9F)
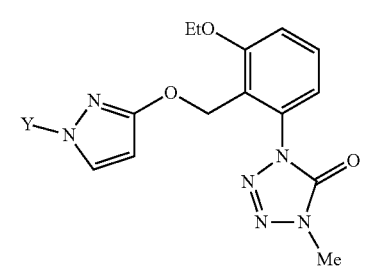 (Q9G)
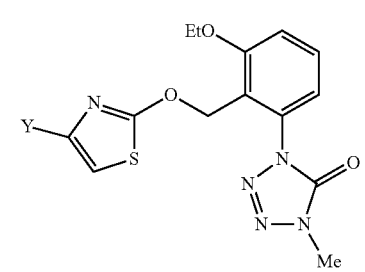 (Q9H)
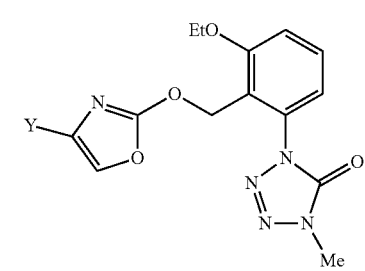 (Q9I)
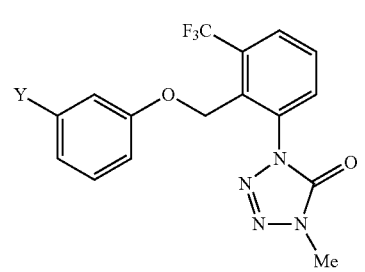 (Q10A)
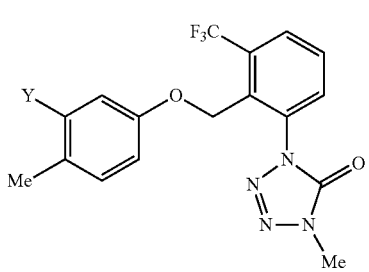 (Q10B)
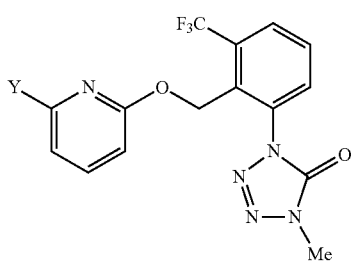 (Q10C)
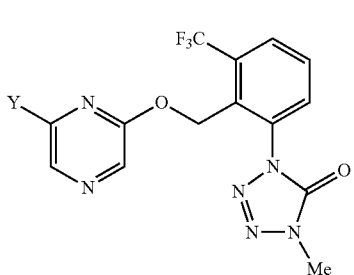 (Q10D)
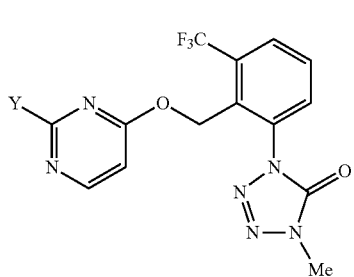 (Q10E)
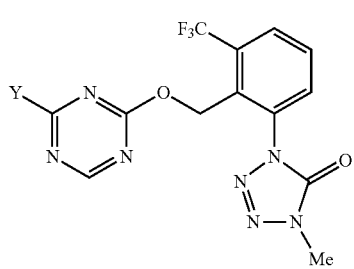 (Q10F)
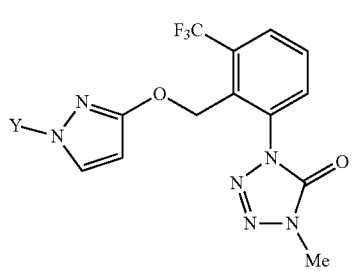 (Q10G)
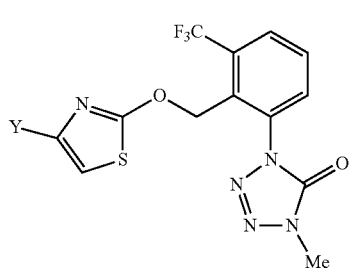 (Q10H)

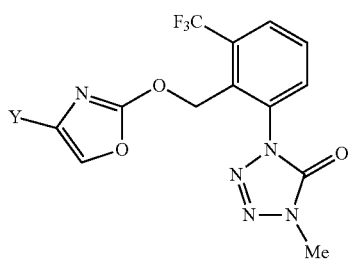
(Q10I)

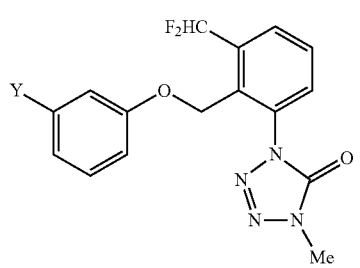
(Q11A)

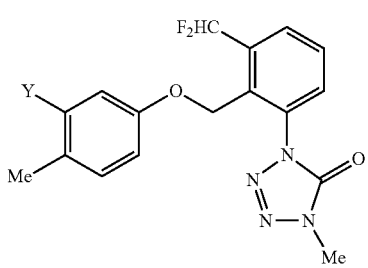
(Q11B)

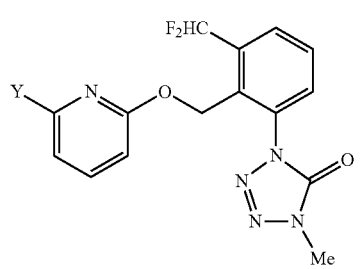
(Q11C)

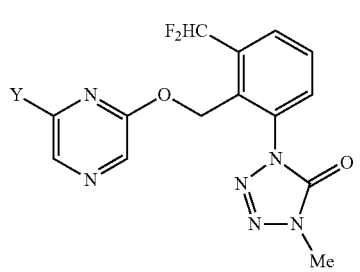
(Q11D)

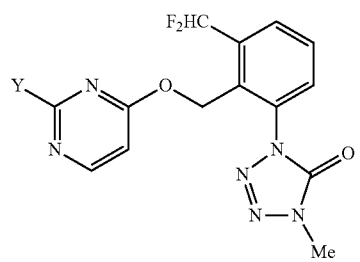
(Q11E)

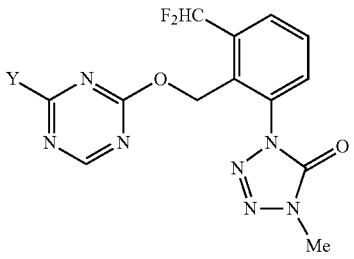
(Q11F)

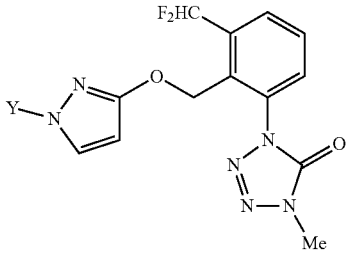
(Q11G)

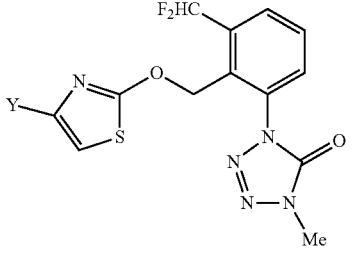
(Q11H)

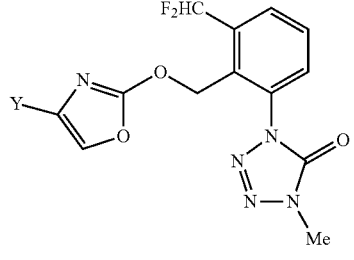
(Q11I)

[substituent number; Y]
[1; phenoxy group], [2; 2-methylphenoxy group], [3; 3-methylphenoxy group], [4; 4-methylphenoxy group], [5; 2-ethylphenoxy group], [6; 3-ethylphenoxy group], [7; 4-ethylphenoxy group], [8; 2-fluorophenoxy group], [9; 3-fluorophenoxy group], [10; 4-fluorophenoxy group], [11; 2-chlorophenoxy group], [12; 3-chlorophenoxy group], [13; 4-chlorophenoxy group], [14; 2-bromophenoxy group], [15; 3-bromophenoxy group], [16; 4-bromophenoxy group], [17; 2-iodophenoxy group], [18; 3-iodophenoxy group], [19; 4-iodophenoxy group], [20; 2-cyanophenoxy group], [21; 3-cyanophenoxy group], [22; 4-cyanophenoxy group], [23; 2-methoxyphenoxy group], [24; 3-methoxyphenoxy group], [25; 4-methoxyphenoxy group], [26; 2-ethoxyphenoxy group], [27; 3-ethoxyphenoxy group], [28; 4-ethoxyphenoxy group], [29; 2-trifluoromethylphenoxy group], [30; 3-trifluoromethylphenoxy group], [31; 4-trifluoromethylphenoxy group], [32; 2-difluoromethylphenoxy group], [33; 3-difluoromethylphenoxy group], [34; 4-difluoromethylphenoxy group], [35; 2-trifluoromethoxyphenoxy group], [36; 3-trifluoromethoxyphenoxy group], [37; 4-trifluoromethoxyphenoxy group], [38; 2-cyclopropylphenoxy group], [39; 3-cyclopropylphenoxy group], [40; 4-cyclopropylphenoxy group], [41; 2-methylthiophenoxy group], [42; 3-methylthiophenoxy group], [43; 4-methylthiophenoxy group], [44; 2-ethylthiophenoxy group], [45; 3-ethylthiophenoxy group], [46; 4-ethylthiophenoxy group], [47; 2,3-difluorophenoxy group], [48; 2,4-difluorophenoxy group], [49; 2,5-difluorophenoxy group], [50; 2,6-difluorophenoxy group], [51; 3,4-difluorophenoxy group], [52; 3,5-difluorophenoxy group], [53; 2-chloro-4-fluorophenoxy group], [54; 2-fluoro-4-methoxyphenoxy group], [55; 2-cyano-4-methoxyphenoxy group], [56; 2-methoxy-4-chlorophenoxy group], [57; phenylthio group], [58; 2-methylphenylthio group], [59; 3-methylphenylthio group], [60; 4-methylphenylthio group], [61; 2-ethylphenylthio group], [62; 3-ethylphenylthio group], [63; 4-ethylphenylthio group], [64; 2-fluorophenylthio group], [65; 3-fluorophenylthio group], [66; 4-fluorophenylthio group], [67; 2-chlorophenylthio group], [68; 3-chlorophenylthio group], [69; 4-chlorophenylthio group], [70; 2-bromophenylthio group], [71; 3-bromophenylthio group], [72; 4-bromophenylthio group], [73; 2-iodophenylthio group], [74; 3-iodophenylthio group], [75; 4-iodophenylthio group], [76; 2-cyanophenylthio group], [77; 3-cyanophenylthio group], [78; 4-cyanophenylthio group], [79; 2-methoxyphenylthio group], [80; 3-methoxyphenylthio group], [81; 4-methoxyphenylthio group], [82; 2-ethoxyphenylthio group], [83; 3-ethoxyphenylthio group], [84; 4-ethoxyphenylthio group], [85; 2-trifluoromethylphenylthio group], [86; 3-trifluoromethylphenylthio group], [87; 4-trifluoromethylphenylthio group], [88; 2-difluoromethylphenylthio group], [89; 3-difluoromethylphenylthio group], [90; 4-difluoromethylphenylthio group], [91; 2-trifluoromethoxyphenylthio group], [92; 3-trifluoromethoxyphenylthio group], [93; 4-trifluoromethoxyphenylthio group], [94; 2-cyclopropylphenylthio group], [95; 3-cyclopropylphenylthio group], [96; 4-cyclopropylphenylthio group], [97; 2-methylthiophenylthio group], [98; 3-methylthiophenylthio group], [99; 4-methylthiophenylthio group], [100; 2-ethylthiophenylthio group],
[101; 3-ethylthiophenylthio group], [102; 4-ethylthiophenylthio group], [103; 2,3-difluorophenylthio group], [104; 2,4-difluorophenylthio group], [105; 2,5-difluorophenylthio group], [106; 2,6-difluorophenylthio group], [107; 3,4-difluorophenylthio group], [108; 3,5-difluorophenylthio group], [109; 2-chloro-4-fluorophenylthio group], [110; 2-fluoro-4-methoxyphenylthio group], [111; 2-cyano-4-methoxyphenylthio group], [112; 2-methoxy-4-chlorophenylthio group], [113; benzyloxy group], [114; 2-methylbenzyloxy group], [115; 3-methylbenzyloxy group], [116; 4-methylbenzyloxy group], [117; 2-ethylbenzyloxy group], [118; 3-ethylbenzyloxy group], [119; 4-ethylbenzyloxy group], [120; 2-fluorobenzyloxy group], [121; 3-fluorobenzyloxy group], [122; 4-fluorobenzyloxy group], [123; 2-chlorobenzyloxy group], [124; 3-chlorobenzyloxy group], [125; 4-chlorobenzyloxy group], [126; 2-bromobenzyloxy group], [127; 3-bromobenzyloxy group], [128; 4-bromobenzyloxy group], [129; 2-iodobenzyloxy group], [130; 3-iodobenzyloxy group], [131; 4-iodobenzyloxy group], [132; 2-cyanobenzyloxy group], [133; 3-cyanobenzyloxy group], [134; 4-cyanobenzyloxy group], [135; 2-methoxybenzyloxy group], [136; 3-methoxybenzyloxy group], [137; 4-methoxybenzyloxy group], [138; 2-ethoxybenzyloxy group], [139; 3-ethoxybenzyloxy group], [140; 4-ethoxybenzyloxy group], [141; 2-trifluoromethylbenzyloxy group], [142; 3-trifluoromethylbenzyloxy group], [143; 4-trifluoromethylbenzyloxy group], [144; 2-difluoromethylbenzyloxy group], [145; 3-difluoromethylbenzyloxy group], [146; 4-difluoromethylbenzyloxy group], [147; 2-trifluoromethoxybenzyloxy group], [148; 3-trifluoromethoxybenzyloxy group], [149; 4-trifluoromethoxybenzyloxy group], [150; 2-cyclopropylbenzyloxy group], [151; 3-cyclopropylbenzyloxy group], [152; 4-cyclopropylbenzyloxy group], [153; 2-methylthiobenzyloxy group], [154; 3-methylthiobenzyloxy group], [155; 4-methylthiobenzyloxy group], [156; 2-ethylthiobenzyloxy group], [157; 3-ethylthiobenzyloxy group], [158; 4-ethylthiobenzyloxy group], [159; 2,3-difluorobenzyloxy group], [160; 2,4-difluorobenzyloxy group], [161; 2,5-difluorobenzyloxy group], [162; 2,6-difluorobenzyloxy group], [163; 3,4-difluorobenzyloxy group], [164; 3,5-difluorobenzyloxy group], [165; 2-chloro-4-fluorobenzyloxy group], [166; 2-fluoro-4-methoxybenzyloxy group], [167; 2-cyano-4-methoxybenzyloxy group], [168; 2-methoxy-4-chlorobenzyloxy group], [169; pyridin-2-ylmethoxy group], [170; pyridine-3-ylmethoxy group], [171; pyridine-4-ylmethoxy group], [172; 5-methoxypyridin-2-ylmethoxy group], [173; 5-chloropyridin-2-ylmethoxy group], [174; 2-methoxypyridine-3-ylmethoxy group], [175; 2-methoxy-6-trifluoromethylpyridine-3-ylmethoxy group], [176; 2-methoxy-6-fluoropyridine-3-ylmethoxy group], [177; 2-phenylethyl group], [178; 2-(2-methylphenyl)ethyl group], [179; 2-(3-methylphenyl)ethyl group], [180; 2-(4-methylphenyl)ethyl group], [181; 2-(2-ethylphenyl)ethyl group], [182; 2-(3-ethylphenyl)ethyl group], [183; 2-(4-ethylphenyl)ethyl group], [184; 2-(2-fluorophenyl)ethyl group], [185; 2-(3-fluorophenyl)ethyl group], [186; 2-(4-fluorophenyl)ethyl group], [187; 2-(2-chlorophenyl)ethyl group], [188; 2-(3-chlorophenyl)ethyl group], [189; 2-(4-chlorophenyl)ethyl group], [190; 2-(2-cyanophenyl)ethyl group], [191; 2-(3-cyanophenyl)ethyl group], [192; 2-(4-cyanophenyl)ethyl group], [193; 1-(methoxyimino)ethyl group], [194; 1-(ethoxyimino)ethyl group], [195; 1-[(propoxy)imino]ethyl group], [196; 1-[(isopropoxy)imino]ethyl group], [197; 1-(tert-butoxyimino)ethyl group], [198; 1-(allyloxyimino)ethyl group], [199; 1-(propargylimino)ethyl group], [200; 1-(phenoxyimino)ethyl group], [201; 1-(benzyloxyimino)ethyl group], [202; 1-[(2-methylbenzyloxy)imino]ethyl group], [203; 1-[(3-methylbenzyloxy)imino]ethyl group], [204; 1-[(4-methylbenzyloxy)imino]ethyl group], [205; 1-[(2-fluorobenzyloxy)imino]ethyl group], [206; 1-[(3-fluorobenzyloxy)imino]ethyl group], [207; 1-[(4-fluorobenzyloxy)imino]ethyl group], [208; 1-[(2-chlorobenzyloxy)imino]ethyl group], [209; 1-[(3-chlorobenzyloxy)imino]ethyl group], [210; 1-[(4-chlorobenzyloxy)imino]ethyl group], [211; 1-[(2-methoxybenzyloxy)imino]ethyl group], [212; 1-[(3-methoxybenzyloxy)imino]ethyl group], [213; 1-[(4-methoxybenzyloxy)imino]ethyl group], [214; 1-[(2-cyanobenzyloxy)imino]ethyl group], [215; 1-[(3-cyanobenzyloxy)imino]ethyl group], [216; 1-[(4-cyanobenzyloxy)imino]ethyl group], [217; 1-[(2-trifluoromethylbenzyloxy)imino]ethyl group], [218; 1-[(3-trifluoromethylbenzyloxy)imino]ethyl group], [219; 1-[(4-trifluoromethylbenzyloxy)imino]ethyl group], [220; 1-(methoxyimino)propyl group], [221; 1-(ethoxyimino)propyl group], [222; 1-[(propoxy)imino]propyl group], [223; 1-[(isopropoxy)imino]propyl group], [224; 1-(tert-butoxy)iminopropyl group], [225; 1-(allyloxyimino)propyl group], [226; 1-(propargyloxyimino)propyl group], [227; 1-(phenoxyimino)propyl group], [228; 1-(benzyloxyimino)propyl group], [229; 1-[(2-methylbenzyloxy)imino]propyl group], [230; 1-[(3-methylbenzyloxy)imino]propyl group], [231; 1-[(4-methylbenzyloxy)imino]propyl group], [232; 1-[(2-fluorobenzyloxy)imino]propyl group], [233; 1-[(3-fluorobenzyloxy)imino]propyl group], [234; 1-[(4-fluorobenzyloxy)imino]propyl group], [235; 1-[(2-chlorobenzyloxy)imino]propyl group], [236; 1-[(3-chlorobenzyloxy)imino]propyl group], [237; 1-[(4-chlorobenzyloxy)

imino]propyl group], [238; 1-[(2-methoxybenzyloxy)imino]propyl group], [239; 1-[(3-methoxybenzyloxy)imino]propyl group], [240; 1-[(4-methoxybenzyloxy)imino]propyl group], [241; 1-[(2-cyanobenzyloxy)imino]propyl group], [242; 1-[(3-cyanobenzyloxy)imino]propyl group], [243; 1-[(4-cyanobenzyloxy)imino]propyl group], [244; 1-[(2-trifluoromethylbenzyloxy)imino]propyl group], [245; 1-[(3-trifluoromethylbenzyloxy)imino]propyl group], [246; 1-[(4-trifluoromethylbenzyloxy)imino]propyl group], [247; 1-(methoxyimino)butyl group], [248; 1-(ethoxyimino)butyl group], [249; 1-[(1-propyloxy)imino]butyl group], [250; 1-[(2-propyloxy)imino]butyl group], [251; 1-(tert-butoxyimino)butyl group], [252; 1-(allyloxyimino)butyl group], [253; 1-(propargyloxyimino)butyl group], [254; 1-(phenoxyimino)butyl group], [255; 1-(benzyloxyimino)butyl group], [256; 1-[(2-methylbenzyloxy)imino]butyl group], [257; 1-[(3-methylbenzyloxy)imino]butyl group], [258; 1-[(4-methylbenzyloxy)imino]butyl group], [259; 1-[(2-fluorobenzyloxy)imino]butyl group], [260; 1-[(3-fluorobenzyloxy)imino]butyl group], [261; 1-[(4-fluorobenzyloxy)imino]butyl group], [262; 1-[(2-chlorobenzyloxy)imino]butyl group], [263; 1-[(3-chlorobenzyloxy)imino]butyl group], [264; 1-[(4-chlorobenzyloxy)imino]butyl group], [265; 1-[(2-methoxybenzyloxy)imino]butyl group], [266; 1-[(3-methoxybenzyloxy)imino]butyl group], [267; 1-[(4-methoxybenzyloxy)imino]butyl group], [268; 1-[(2-cyanobenzyloxy)imino]butyl group], [269; 1-[(3-cyanobenzyloxy)imino]butyl group], [270; 1-[(4-cyanobenzyloxy)imino]butyl group], [271; 1-[(2-trifluoromethylbenzyloxy)imino]butyl group], [272; 1-[(3-trifluoromethylbenzyloxy)imino]butyl group], [273; 1-[(4-trifluoromethylbenzyloxy)imino]butyl group], [274; 1-(methoxyimino)pentyl group], [275; 1-(ethoxyimino)pentyl group], [276; 1-[(propoxy)imino]pentyl group], [277; 1-[(isopropoxy)imino]pentyl group], [278; 1-(tert-butoxyimino)pentyl group], [279; 1-(allyloxyimino)pentyl group], [280; 1-(propargyloxyimino)pentyl group], [281; 1-(phenoxyimino)pentyl group], [282; 1-(benzyloxyimino)pentyl group], [283; 1-[(2-methylbenzyloxy)imino]pentyl group], [284; 1-[(3-methylbenzyloxy)imino]pentyl group], [285; 1-[(4-methylbenzyloxy)imino]pentyl group], [286; 1-[(2-fluorobenzyloxy)imino]pentyl group], [287; 1-[(3-fluorobenzyloxy)imino]pentyl group], [288; 1-[(4-fluorobenzyloxy)imino]pentyl group], [289; 1-[(2-chlorobenzyloxy)imino]pentyl group], [290; 1-[(3-chlorobenzyloxy)imino]pentyl group], [291; 1-[(4-chlorobenzyloxy)imino]pentyl group], [292; 1-[(2-methoxybenzyloxy)imino]pentyl group], [293; 1-[(3-methoxybenzyloxy)imino]pentyl group], [294; 1-[(4-methoxybenzyloxy)imino]pentyl group], [295; 1-[(2-cyanobenzyloxy)imino]pentyl group], [296; 1-[(3-cyanobenzyloxy)imino]pentyl group], [297; 1-[(4-cyanobenzyloxy)imino]pentyl group], [298; 1-[(2-trifluoromethylbenzyloxy)imino]pentyl group], [299; 1-[(3-trifluoromethylbenzyloxy)imino]pentyl group], [300; 1-[(4-trifluoromethylbenzyloxy)imino]pentyl group],
[301; (methoxyimino)methyl group], [302; (ethoxyimino)methyl group], [303; [pro]poxy)imino]methyl group], [304; [isopro]poxy)imino]methyl group], [305; (tert-butoxyimino)methyl group], [306; (allylimino)methyl group], [307; (propargylimino)methyl group], [308; (phenoxyimino)methyl group], [309; (benzyloxyimino)methyl group], [310; [(2-methylbenzyloxy)imino]methyl group], [311; [(3-methylbenzyloxy)imino]methyl group], [312; [(4-methylbenzyloxy)imino]methyl group], [313; [(2-fluorobenzyloxy)imino]methyl group], [314; [(3-fluorobenzyloxy)imino]methyl group], [315; [(4-fluorobenzyloxy)imino]methyl group], [316; [(2-chlorobenzyloxy)imino]methyl group], [317; [(3-chlorobenzyloxy)imino]methyl group], [318; [(4-chlorobenzyloxy)imino]methyl group], [319; [(2-methoxybenzyloxy)imino]methyl group], [320; [(3-methoxybenzyloxy)imino]methyl group], [321; [(4-methoxybenzyloxy)imino]methyl group], [322; [(2-cyanobenzyloxy)imino]methyl group], [323; [(3-cyanobenzyloxy)imino]methyl group], [324; [(4-cyanobenzyloxy)imino]methyl group], [325; [(2-trifluoromethylbenzyloxy)imino]methyl group], [326; [(3-trifluoromethylbenzyloxy)imino]methyl group], [327; [(4-trifluoromethylbenzyloxy)imino]methyl group], [328; [(methoxyimino)cyclopropyl]methyl group], [329; (ethoxyimino) (cyclopropyl)methyl group], [330; [(1-propyloxy)imino](cyclopropyl)methyl group], [331; [(2-propyloxy)imino](cyclopropyl)methyl group], [332; [(tert-butoxy)imino](cyclopropyl)methyl group], [333; [(allyloxy)imino](cyclopropyl)methyl group], [334; [(propargyloxy)imino]cyclopropyl)methyl group], [335; (phenoxyimino)(cyclopropyl)methyl group], [336; (benzyloxyimino) (cyclopropyl)methyl group], [337; [(2-methylbenzyloxy)imino](cyclopropyl)methyl group], [338; [(3-methylbenzyloxy)imino](cyclopropyl)methyl group], [339; [(4-methylbenzyloxy)imino](cyclopropyl)methyl group], [340; [(2-fluorobenzyloxy)imino](cyclopropyl)methyl group], [341; [(3-fluorobenzyloxy)imino](cyclopropyl)methyl group], [342; [(4-fluorobenzyloxy)imino](cyclopropyl)methyl group], [343; [(2-chlorobenzyloxy)imino](cyclopropyl)methyl group], [344; [(3-chlorobenzyloxy)imino](cyclopropyl)methyl group], [345; [(4-chlorobenzyloxy)imino](cyclopropyl)methyl group], [346; [(2-methoxybenzyloxy)imino](cyclopropyl)methyl group], [347; [(3-methoxybenzyloxy)imino](cyclopropyl)methyl group], [348; [(4-methoxybenzyloxy)imino]; (cyclopropyl)methyl group], [349; [(2-cyanobenzyloxy)imino](cyclopropyl)methyl group], [350; [(3-cyanobenzyloxy)imino](cyclopropyl)methyl group], [351; [(4-cyanobenzyloxy)imino]; (cyclopropyl)methyl group], [352; [(2-trifluoromethylbenzyloxy)imino](cyclopropyl)methyl group], [353; [(3-trifluoromethylbenzyloxy)imino](cyclopropyl)methyl group], [354; [(4-trifluoromethylbenzyloxy)imino](cyclopropyl)methyl group], [355; (methoxyimino) (phenyl)methyl group], [356; (ethoxyimino) (phenyl)methyl group], [357; [(1-propyloxy)imino](phenyl)methyl group], [358; [(2-propyloxy)imino](phenyl)methyl group], [359; (tert-butoxyimino) (phenyl)methyl group], [360; (allyloxyimino) (phenyl)methyl group], [361; (propargyloxyimino) (phenyl)methyl group], [362; (phenoxyimino) (phenyl)methyl group], [363; (benzyloxyimino) (phenyl)methyl group], [364; [(2-methylbenzyloxy)imino](phenyl)methyl group], [365; [(3-methylbenzyloxy)imino](phenyl)methyl group], [366; [(4-methylbenzyloxy)imino](phenyl)methyl group], [367; [(2-fluorobenzyloxy)imino](phenyl)methyl group], [368; [(3-fluorobenzyloxy)imino](phenyl)methyl group], [369; [(4-fluorobenzyloxy)imino](phenyl)methyl group], [370; [(2-chlorobenzyloxy)imino](phenyl)methyl group], [371; [(3-chlorobenzyloxy)imino](phenyl)methyl group], [372; [(4-chlorobenzyloxy)imino](phenyl)methyl group], [373; [(2-methoxybenzyloxy)imino](phenyl)methyl group], [374; [(3-methoxybenzyloxy)imino](phenyl)methyl group], [375; [(4-methoxybenzyloxy)imino](phenyl)methyl group], [376; [(2-cyanobenzyloxy)imino](phenyl)methyl group], [377; [(3-cyanobenzyloxy)imino](phenyl)methyl group], [378; [(4-cyanobenzyloxy)imino](phenyl)methyl group], [379; [(2-trifluoromethylbenzyloxy)imino](phenyl)methyl group], [380; [(3-trifluoromethylbenzyloxy)imino](phenyl)methyl group], [381; [(4-trifluoromethylbenzyloxy)imino](phenyl)methyl group], [382; 2-pyridyloxy group],

[383; 3-pyridyloxy group], [384; 4-pyridyloxy group], [385; 2-pyrazolyloxy group], [386; 2-benzoxazolyloxy group], [387; 2-benzothiazolyloxy group], [388; 2-quinolyloxy group], [389; 2-pyrimidinyloxy group], [390; 2-pyrazinyloxy group], [391; (2-pyridyl)methoxy group], [392; (3-pyridyl)methoxy group], [393; (4-pyridyl)methoxy group], [394; anilino group], [395; N-methylanilino group], [396; N-ethylanilino group], [397; 2-fluoroanilino group], [398; 3-fluoroanilino group], [399; 4-fluoroanilino group], [400; 2-chloroanilino group], [401; 3-chloroanilino group], [402; 4-chloroanilino group], [403; 2-methylanilino group], [404; 3-methylanilino group], [405; 4-methylanilino group], [406; 2-ethylanilino group], [407; 3-ethylanilino group], [408; 4-ethylanilino group], [409; 2,3-difluoroanilino group], [410; 2,4-difluoroanilino group], [411; 2,5-difluoroanilino group], [412; 2,6-difluoroanilino group], [413; 3,4-difluoroanilino group], [414; 2-cyanoanilino group], [415; 3-cyanoanilino group], [416; 4-cyanoanilino group], [417; 2-fluoro-N-methylanilino group], [418; 3-fluoro-N-methylanilino group], [419; 4-fluoro-N-methylanilino group], [420; 2-chloro-N-methylanilino group], [421; 3-chloro-N-methylanilino group], [422; 4-chloro-N-methylanilino group], [423; 2-methyl-N-methylanilino group], [424; 3-methyl-N-methylanilino group], [425; 4-methyl-N-methylanilino group], [426; 2-ethyl-N-methylanilino group], [427; 3-ethyl-N-methylanilino group], [428; 4-ethyl-N-methylanilino group], [429; 2,3-difluoro-N-methylanilino group], [430; 2,4-difluoro-N-methylanilino group], [431; 2,5-difluoro-N-methylanilino group], [432; 2,6-difluoro-N-methylanilino group], [433; 3,4-difluoro-N-methylanilino group], [434; 2-cyano-N-methylanilino group], [435; 3-cyano-N-methylanilino group], [436; 4-cyano-N-methylanilino group]

Formulation Examples will be shown below. Parts are by weight.

Formulation Example 1

Fifty parts (50 parts) of any one of the present compounds A, 3 parts of calcium ligninsulfonate, 2 parts of laurylmagnesium sulfate, and 45 parts of synthetic hydrated silicon oxide are thoroughly ground and mixed to obtain each formulation.

Formulation Example 2

Twenty parts (20 parts) of any one of the present compounds A and 1.5 parts of sorbitan trioleate are mixed with 28.5 parts of an aqueous solution containing 2 parts of polyvinyl alcohol, and the mixture was finely ground by a wet grinding method. Then, 40 parts of an aqueous solution containing 0.05 part of xanthan gum and 0.1 part of aluminum magnesium silicate is added thereto and 10 parts of propylene glycol is further added, followed by stirring and mixing to obtain each formulation.

Formulation Example 3

Two parts (2 parts) of any one of the present compounds A, 88 parts of kaolin clay, and 10 parts of talc are thoroughly ground and mixed to obtain each formulation.

Formulation Example 4

Five parts (5 parts) of any one of the present compounds A, 14 parts of polyoxyethylene styryl phenyl ether, 6 parts of calcium dodecylbenzenesulfonate, and 75 parts of xylene are thoroughly ground and mixed to obtain each formulation.

Formulation Example 5

Two parts (2 parts) of any one of the present compounds A, 1 part of synthetic hydrated silicon oxide, 2 parts of calcium ligninsulfonate, 30 parts of bentonite, and 65 parts of kaolin clay are thoroughly ground and mixed. After the addition of water, the mixture is thoroughly kneaded and further granulated and dried to obtain each formulation.

Formulation Example 6

Ten parts (10 parts) of any one of the present compounds A, 35 parts of white carbon containing 50 parts of a polyoxyethylene alkyl ether sulfate ammonium salt, and 55 parts of water were finely ground by a wet grinding method to obtain each formulation.

The following Test Examples will show that the present compounds are useful for controlling plant diseases.

The control effect was evaluated by visually observing the area of lesion on each of test plants at the time of investigation, and comparing the area of lesion on a plant treated with the present compound with that on an untreated plant.

Test Example 1

Each of plastic pots was filled with soil and rice (cultivar: NIHONBARE) was sowed and grown in a greenhouse for 20 days. Then, each water dilution prepared by adjusting so as to contain a predetermined concentration (500 ppm) of any one compound of the present compounds 7, 13, 40, and 44 was sprayed over stems and leaves so that it sufficiently adhered to the surface of the leaves of the rice. After spraying, the plant was air-dried and placed for 6 days at 24° C. in the daytime and 20° C. at night under high humidity condition, while being in contact with the rice seedling (cultivar: NIHONBARE) infected by the rice blast fungus (*Magnaporthe grisea*), and then the area of lesion was investigated. As a result, the lesion areas on the plant treated with the present compound 7, 13, 40, or 44 were 30% or less with respect to the lesion area on the non-treated plant.

Test Example 2

Each of plastic pots was filled with soil and wheat (cultivar: SHIROGANE) was sowed and grown in a greenhouse for 9 days. Then, each water dilution prepared by adjusting so as to contain a predetermined concentration (500 ppm) of any one compound of the present compounds 13, 21, 22, 37, and 43 was sprayed over stems and leaves of the wheat so that it sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was placed at 23° C. for one day under dark and high humidity condition, and cultivated under illumination at 20° C. for 8 days, and then the area of lesion was investigated. As a result, it has been found that the area of lesion on the plant treated with the present compound 13, 21, 22, 37, or 43 was 30% or less of that on an untreated plant.

Test Example 3

Each of plastic pots was filled with soil and barley (cultivar: NISHINOHOSHI) was sowed and grown in a greenhouse for 7 days. Then, each water dilution prepared by adjusting so as to contain a predetermined concentration (500 ppm) of any one compound of the present compounds 1, 2, 3, 4, 5, 6, 7, 8, 9, 10, 11, 12, 13, 14, 15, 16, 18, 19, 20, 21, 22, 23, 24, 25, 26, 27, 28, 29, 32, 33, 34, 35, 36, 37, 38, 39, 40, 41, 42, 43, and 44 was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was placed for 3 days in a greenhouse at 23° C. in the daytime and 20° C. at night under high humidity condition and cultivated in a greenhouse for 7 days, and then the area of lesion was investigated. As a result, the area of lesion on the plant treated with the present compound 1, 2, 3, 4, 5, 6, 7, 8, 9, 10, 11, 12, 13, 14, 15, 16, 18, 19, 20, 21, 22, 23, 24, 25, 26, 27, 28, 29, 32, 33, 34, 35, 36, 37, 38, 39, 40, 41, 42, 43, or 44 was 30% or less of that on an untreated plant.

Test Example 4

Each of plastic pots was filled with soil and kidney bean (cultivar: NAGAUZURA SAIYTOU) was sowed and grown in a greenhouse for 8 days. Then, each water dilution prepared by adjusting so as to contain a predetermined concentration (500 ppm) of any one compound of the present compounds 4, 5, 6, 7, 8, 9, 10, 11, 12, 13, 15, and 16 was sprayed over stems and leaves of the kidney bean so that it sufficiently adhered to the surface of the leaves of the kidney bean. After spraying, the plant was air-dried and a PDA medium containing hyphae of the kidney bean stem rot fungus (*Sclerotinia sclerotiorum*) was placed on the leaves of the kidney bean. After the inoculation, all kidney beans were placed under high humidity condition only at night. Four days after the inoculation, the area of lesion was investigated. As a result, the area of lesion on the plant treated with the present compound 4, 5, 6, 7, 8, 9, 10, 11, 12, 13, 15, or 16 was 30% or less of that on an untreated plant.

Test Example 5

Each of plastic pots was filled with soil and wheat (cultivar: APOGEE) was sowed and grown in a greenhouse for 10 days. Then, each water dilution prepared by adjusting so as to contain a predetermined concentration (500 ppm) of any one compound of the present compounds 1, 2, 4, 5, 6, 7, 8, 9, 11, 12, 13, 14, 15, 16, 18, 19, 20, 21, 22, 23, 24, 25, 26, 27, 28, 29, 33, 36, 37, 39, 40, 41, 42, 43, and 44 was sprayed over stems and leaves of the wheat so that it sufficiently adhered to the surface of the leaves of the wheat. After spraying, the plant was air-dried. After 4 days, an aqueous suspension containing spores of wheat leaf blotch fungus (*Septoria tritici*) was sprayed to inoculate the spores. After completion of the inoculation, the plant was placed at 18° C. under high humidity condition for 3 days and left to stand under illumination for 14 to 18 days, and then the area of lesion was investigated. As a result, the area of lesion on the plant treated with the present compound 1, 2, 4, 5, 6, 7, 8, 9, 11, 12, 13, 14, 15, 16, 18, 19, 20, 21, 22, 23, 24, 25, 26, 27, 28, 29, 33, 36, 37, 39, 40, 41, 42, 43, or 44 was 30% or less of that on an untreated plant.

Test Example 6

Each of plastic pots was filled with soil and cucumber (cultivar: SAGAMI HANJIRO) was sowed and grown in a greenhouse for 12 days. Then, each water dilution prepared by adjusting so as to contain a predetermined concentration (500 ppm) of any one compound of the present compounds 1, 2, 4, 5, 6, 7, 8, 9, 11, 12, 13, 14, 15, 16, 18, 19, 20, 21, 22, 23, 24, 25, 26, 27, 28, 29, 33, 36, 37, 39, 40, 43, and 44 was sprayed over stems and leaves of the cucumber so that it sufficiently adhered to the surface of the leaves of the cucumber. After spraying, the plant was air-dried and then inoculated by sprinkling with spores of cucumber powdery mildew fungus (*Sphaerotheca fuliginea*). After the inoculation, the plant was cultivated in a greenhouse at 24° C. in the daytime and 20° C. at night for 8 days, and then the area of lesion was investigated. As a result, the area of lesion on the plant treated with the present compound 1, 2, 4, 5, 6, 7, 8, 9, 11, 12, 13, 14, 15, 16, 18, 19, 20, 21, 22, 23, 24, 25, 26, 27, 28, 29, 33, 36, 37, 39, 40, 43, or 44 was 30% or less of that on an untreated plant.

Test Example 7

Each of plastic pots was filled with soil and soybean (cultivar: KUROSENGOKU) was sowed and grown in a greenhouse for 13 days. Then, each water dilution prepared by adjusting so as to contain a predetermined concentration (200 ppm) of the present compound 44 was sprayed over stems and leaves of the soybean so that it sufficiently adhered to the surface of the leaves of the soybean. After spraying, the plant was air-dried. After 2 days, an aqueous suspension containing spores of soybean rust fungus (*Phakopsora pachyrhizi*) was sprayed to inoculate the spores. After completion of the inoculation, the plant was placed for 3 days in a greenhouse at 23° C. in the daytime and 20° C. at night under high humidity condition and cultivated in a greenhouse for 14 days, and then the area of lesion was investigated. As a result, it has been found that the area of lesion on the plant treated with the present compound 44 was 30% or less of that on an untreated plant.

Test Example 8

Each of plastic pots was filled with soil and barley (cultivar: NISHINOHOSHI) was sowed and grown in a greenhouse for 7 days. Then, each water dilution containing a surfactant prepared by adjusting so as to contain a predetermined concentration (200 ppm) of any one compound of the present compounds 1, 2, 4, 5, 6, 7, 8, 9, 11, 12, 13, 14, 15, 16, 18, 19, 20, 21, 22, 23, 24, 25, 26, 27, 28, 29, 33, 36, 37, 39, 40, 41, 42, 43, 44, and 46 was sprayed over stems and leaves of the barley so that it sufficiently adhered to the surface of the leaves of the barley. After spraying, the plant was air-dried. After 2 days, an aqueous suspension containing spores of barley scald fungus (*Rhynchosporium secalis*) was sprayed to inoculate the spores. After completion of the inoculation, the plant was placed for 3 days in a greenhouse at 23° C. in the daytime and 20° C. at night under high humidity condition and cultivated in a greenhouse for 7 days, and then the area of lesion was investigated. As a result, it has been found that the area of lesion on the plant treated with of the present compound 1, 2, 4, 5, 6, 7, 8, 9, 11, 12, 13, 14, 15, 16, 18, 19, 20, 21, 22, 23, 24, 25, 26, 27, 28, 29, 33, 36, 37, 39, 40, 41, 42, 43, 44, or 46 was 30% or less of that on an untreated plant.

Test Example 9

Each of plastic pots was filled with soil and cucumber (cultivar: SAGAMI HANJIRO) was sowed and grown in a greenhouse for 19 days. Then, each water dilution prepared by adjusting so as to contain a predetermined concentration (200 ppm) of any one compound of the present compounds 7, 8, 9, 11, 12, 14, 16, 17, 18, 19, 21, 22, 23, 24, 25, 28, and 46 was sprayed over stems and leaves of the cucumber so that it sufficiently adhered to the surface of the leaves of the cucumber. After spraying, the plant was air-dried and then, after 1 day, an aqueous suspension containing spores of cucumber target leaf spot fungus (*Corynespora cassiicola*) was sprayed to inoculate the spores. After the inoculation, the plant was cultivated in a greenhouse at 24° C. in the daytime and 20° C. at night for 7 days under high humidity condition, and then the area of lesion was investigated. As a result, the area of lesion on the plant treated with the present compound 7, 8, 9, 11, 12, 14, 16, 17, 18, 19, 21, 22, 23, 24, 25, 28, or 46 was 30% or less of that on an untreated plant.

Test Example 10

Each of plastic pots was filled with soil and cucumber (cultivar: SAGAMI HANJIRO) was sowed and grown in a greenhouse for 19 days. Then, each water dilution prepared by adjusting so as to contain a predetermined concentration (200 ppm) of any one compound of the present compounds 7, 12, 14, 16, 17, 19, 21, 22, 23, 24, 25, and 28 was sprayed over stems and leaves of the cucumber so that it sufficiently adhered to the surface of the leaves of the cucumber. After spraying, the plant was air-dried and then, after 1 day, an aqueous suspension containing spores of cucumber anthracnose fungus (*Colletotrichum lagenarium*) was sprayed to inoculate the spores. After the inoculation, the plant was left to stand at 23° C. for one day under high humidity condition, and then cultivated in a greenhouse at 24° C. in the daytime and 20° C. at night for 6 days, and then the area of lesion was investigated. As a result, the area of lesion on the plant treated with the present compound 7, 12, 14, 16, 17, 19, 21, 22, 23, 24, 25, or 28 was 30% or less of that on an untreated plant.

The present compound has control activity against pests and is useful as an active ingredient of a pest control agent.

The invention claimed is:
1. A tetrazolinone compound represented by formula (1):

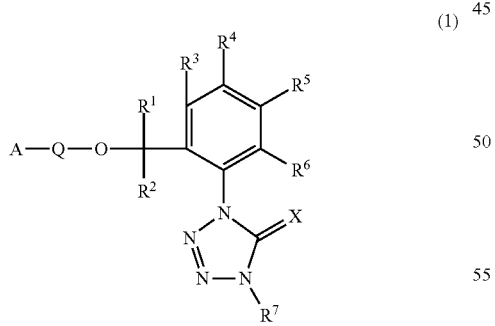

wherein
$R^1$ and $R^2$ each independently represents a hydrogen atom, a halogen atom, or a C1-C3 alkyl group;
$R^3$ represents a C1-C6 alkyl group optionally substituted with one or more halogen atoms, a C1-C6 alkoxy group optionally substituted with one or more halogen atoms, a C3-C6 cycloalkyl group optionally substituted with one or more halogen atoms, a halogen atom, a C2-C6 alkenyl group optionally substituted with one or more halogen atoms, a cyano group, a C1-C6 alkylthio group optionally substituted with one or more halogen atoms, a C2-C6 alkynyl group optionally substituted with one or more halogen atoms, a nitro group, an aminocarbonyl group optionally substituted with one or more C1-C6 alkyl groups, a C3-C6 cycloalkyloxy group optionally substituted with one or more halogen atoms, a C3-C6 cycloalkylthio group optionally substituted with one or more halogen atoms, a C3-C6 alkenyloxy group optionally substituted with one or more halogen atoms, a C3-C6 alkynyloxy group optionally substituted with one or more halogen atoms, a C3-C6 alkenylthio group optionally substituted with one or more halogen atoms, a C3-C6 alkynylthio group optionally substituted with one or more halogen atoms, a C2-C6 alkoxycarbonyl group, a hydroxy group, a sulfanyl group, a C1-C8 alkylamino group optionally substituted with one or more halogen atoms, a pentafluorosulfanyl group, a C3-C9 trialkylsilyl group, a C1-C6 alkylsulfonyl group optionally substituted with one or more halogen atoms, a C1-C6 alkylsulfinyl group optionally substituted with one or more halogen atoms, a C2-C6 alkylcarbonyl group, a C2-C5 alkoxyalkyl group, or a C2-C5 alkylthioalkyl group;
$R^4$, $R^5$ and, $R^6$ each independently represents a hydrogen atom, a halogen atom, a C1-C3 alkyl group optionally substituted with one or more halogen atoms, or a C1-C3 alkoxy group optionally substituted with one or more halogen atoms;
$R^7$ represents a C1-C3 alkyl group optionally substituted with one or more halogen atoms;
Q represents a divalent group selected from Group $P^4$,
A represents a C6-C16 aryloxy group optionally substituted with one or more atoms or groups selected from Group $P^2$, a C6-C16 arylthio group optionally substituted with one or more atoms or groups selected from Group $P^2$, $R^{15}O-N=C(R^{16})-$, $R^{13}R^{14}N-N=C(R^{16})-$, $R^{13}R^{14}N-CH=N-$, a C7-C18 aralkyl group optionally substituted with one or more atoms or groups selected from Group $P^2$, a C7-C18 aralkyloxy group optionally substituted with one or more atoms or groups selected from Group $P^2$, a C7-C16 aryloxyalkyl group optionally substituted with one or more atoms or groups selected from Group $P^2$, a C7-C16 arylcarbonyl group optionally substituted with one or more atoms or groups selected from Group $P^2$, an anilino group optionally substituted with one or more atoms or groups selected from Group $P^2$, a C2-C9 heteroaryloxy group optionally substituted with one or more atoms or groups selected from Group $P^2$, wherein the heteroaryl moiety in the heteroaryloxy group represents a 5-membered ring, a 6-membered ring, a fused ring of a 5-membered ring and a 5-membered ring, a fused ring of a 5-membered ring and a 6-membered ring, or a fused ring of a 6-membered ring and a 6-membered ring, a C3-C6 cycloalkyloxy group, or a C4-C10 cycloalkylalkoxy group;
$R^{13}$ and $R^{14}$ are the same or different and represent a C1-C3 alkyl group optionally substituted with one or more halogen atoms;
$R^{15}$ represents a C1-C6 alkyl group optionally substituted with one or more halogen atoms, a C2-C6 alkenyl group optionally substituted with one or more halogen atoms, a C2-C6 alkynyl group optionally substituted with one or more halogen atoms, a C3-C6 cycloalkyl group optionally substituted with one or more halogen atoms, a C7-C18 aralkyl group optionally substituted with one or more atoms or groups selected from Group P¹, or a phenyl group optionally substituted with one or more atoms or groups selected from Group P¹;

R¹⁶ represents a C1-C6 alkyl group optionally substituted with one or more halogen atoms, a hydrogen atom, a C3-C6 cycloalkyl group optionally substituted with one or more halogen atoms, or a phenyl group optionally substituted with one or more halogen atoms;

X represents an oxygen atom or a sulfur atom:

Group P¹: Group consisting of a halogen atom, a cyano group, a C1-C4 alkyl group optionally substituted with one or more halogen atoms, a C3-C6 cycloalkyl group optionally substituted with one or more halogen atoms, a C1-C4 alkoxy group optionally substituted with one or more halogen atoms, and a C1-C4 alkylthio group optionally substituted with one or more halogen atoms;

Group P²: Group consisting of a C1-C6 alkyl group optionally substituted with one or more halogen atoms, a halogen atom, a cyano group, a hydroxy group, a C3-C6 cycloalkyl group optionally substituted with one or more halogen atoms, a C1-C6 alkoxy group optionally substituted with one or more halogen atoms, a C1-C6 alkylthio group optionally substituted with one or more halogen atoms, a C2-C6 alkenyl group optionally substituted with one or more halogen atoms, a C2-C6 alkynyl group optionally substituted with one or more halogen atoms, a C1-C8 alkylamino group optionally substituted with one or more halogen atoms, a C1-C6 alkylsulfinyl group optionally substituted with one or more halogen atoms, a C1-C6 alkylsulfonyl group optionally substituted with one or more halogen atoms, a pentafluorosulfanyl group, a C2-C6 alkoxycarbonyl group, a C2-C6 alkylcarbonyl group, a C2-C6 alkylcarbonyloxy group, a C2-C6 alkylcarbonylamino group, an aminocarbonyl group optionally substituted with one or more C1-C6 alkyl groups, and a C3-C9 trialkylsilyl group; and Group P⁴: Group consisting of a group Q1 and a group Q2:

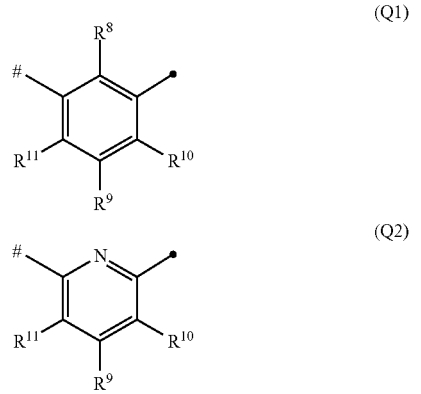

wherein R⁸, R⁹, R¹⁰ and R¹¹ each independently represents a hydrogen atom, a halogen atom, or a C1-C4 alkyl group optionally substituted with one or more halogen atoms, the symbol # represents a binding site for A, and the symbol ● represents a binding site for an oxygen atom.

2. The tetrazolinone compound according to claim 1, wherein R¹, R², R⁴, R⁵, and R⁶ are hydrogen atoms;

R³ is a C1-C4 alkyl group optionally substituted with one or more halogen atoms, a halogen atom, a C1-C4 alkoxy group optionally substituted with one or more halogen atoms, or a C3-C5 cycloalkyl group optionally substituted with one or more halogen atoms; and Q is the following group Q1:

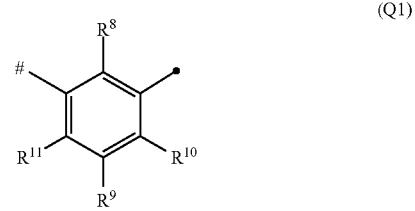

wherein R⁸, R⁹, R¹⁰, R¹¹, the symbol #, and the symbol ● are the same as defined above.

3. The tetrazolinone compound according to claim 1, wherein A is the following group S1':

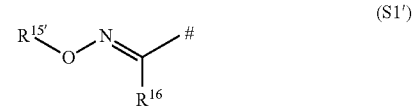

wherein R¹⁵' represents a C1-C6 alkyl group optionally substituted with one or more halogen atoms, a C2-C6 alkenyl group optionally substituted with one or more halogen atoms, a C2-C6 alkynyl group optionally substituted with one or more halogen atoms, a benzyl group optionally substituted with one or more atoms or groups selected from Group P³, or a phenyl group optionally substituted with one or more atoms or groups selected from Group P³, and R¹⁶ and # are the same as defined above:

Group P³: Group consisting of a halogen atom, a cyano group, a C1-C3 alkyl group optionally substituted with one or more halogen atoms, a C1-C3 alkoxy group optionally substituted with one or more halogen atoms, a C3-C4 cycloalkyl group optionally substituted with one or more halogen atoms, and a C1-C3 alkylthio group optionally substituted with one or more halogen atoms.

4. The tetrazolinone compound according to claim 1, wherein A is a C7-C18 aralkyloxy group optionally substituted with one or more atoms or groups selected from Group P³.

5. The tetrazolinone compound according to claim 1, wherein R⁸, R⁹, and R¹¹ are hydrogen atoms, and R¹⁰ is a C1-C4 alkyl group optionally substituted with one or more halogen atoms.

6. The tetrazolinone compound according to claim 1, wherein R¹, R², R⁴, R⁵, and R⁶ are hydrogen atoms;

R³ is a C1-C4 alkyl group optionally substituted with one or more halogen atoms; and Q is the following group Q2':

wherein the symbol # represents a binding site for A, and the symbol ● represents a binding site for an oxygen atom.

7. The tetrazolinone compound according to claim 1, wherein A is a group S1″:

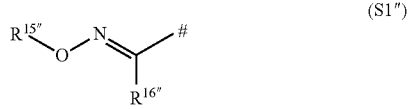

wherein $R^{15″}$ represents a C1-C6 alkyl group optionally substituted with one or more halogen atoms, a C2-C6 alkenyl group optionally substituted with one or more halogen atoms, a C2-C6 alkynyl group optionally substituted with one or more halogen atoms, a benzyl group optionally substituted with one or more atoms or groups selected from Group $P^5$, or a phenyl group optionally substituted with one or more halogen atoms, $R^{16″}$ represents a C1-C6 alkyl group optionally substituted with one or more halogen atoms, or a phenyl group optionally substituted with one or more halogen atoms, and # is the same as defined above:

Group $P^5$: Group consisting of a C1-C3 alkyl group optionally substituted with one or more halogen atoms.

8. The tetrazolinone compound according to claim 1, wherein A is a C7-C18 aralkyloxy group optionally substituted with one or more atoms or groups selected from Group $P^1$, and Group $P^1$ consists of a C1-C3 alkyl group optionally substituted with one or more halogen atoms, a halogen atom, and a C1-C3 alkoxy group optionally substituted with one or more halogen atoms.

9. A pest control agent comprising the tetrazolinone compound according to claim 1.

10. A method for controlling pests, which comprises treating plants or soil with an effective amount of the tetrazolinone compound according to claim 1.

* * * * *

UNITED STATES PATENT AND TRADEMARK OFFICE
CERTIFICATE OF CORRECTION

PATENT NO. : 9,635,857 B2
APPLICATION NO. : 15/029015
DATED : May 2, 2017
INVENTOR(S) : Shioda et al.

It is certified that error appears in the above-identified patent and that said Letters Patent is hereby corrected as shown below:

In the Claims

In Claim 4, at Column 128, Lines 49-50, change "selected from Group $P^3$." to read as follows:
--selected from the following Group $P^3$:
Group $P^3$: Group consisting of a halogen atom, a cyano group, a C1-C3 alkyl group optionally substituted with one or more halogen atoms, a C1-C3 alkoxy group optionally substituted with one or more halogen atoms, a C3-C4 cycloalkyl group optionally substituted with one or more halogen atoms, and a C1-C3 alkylthio group optionally substituted with one or more halogen atoms.--

Signed and Sealed this
Fourteenth Day of August, 2018

Andrei Iancu
*Director of the United States Patent and Trademark Office*